US011604180B2

(12) United States Patent
Meyers et al.

(10) Patent No.: US 11,604,180 B2
(45) Date of Patent: Mar. 14, 2023

(54) VOLTAGE DIFFERENTIAL REDUCTION METHODS USED WHILE RETRIEVING A MOBILE PLATFORM FROM A TANK CONTAINING A HAZARDOUS, NON-CONDUCTIVE SUBSTANCE

(71) Applicant: TANKBOTS, INC., Houston, TX (US)

(72) Inventors: John W. Meyers, Houston, TX (US); Joseph A. Daily, Dillon, MT (US); Robert T. Effinger, IV, Missouri City, TX (US); Donald A. Pontrelli, Glendale, CA (US); David L. Cheuvront, Houston, TX (US); James Todd Lovelace, Jacksonville, FL (US); Ronald Gillory, Houston, TX (US); David John Cassimatis, Garland, TX (US)

(73) Assignee: TANKBOTS, INC., Houston, TX (US)

( * ) Notice: Subject to any disclaimer, the term of this patent is extended or adjusted under 35 U.S.C. 154(b) by 201 days.

(21) Appl. No.: 17/112,302

(22) Filed: Dec. 4, 2020

(65) Prior Publication Data

US 2021/0116419 A1 Apr. 22, 2021

Related U.S. Application Data

(63) Continuation of application No. 16/766,642, filed as application No. PCT/US2018/065888 on Dec. 15, 2018, now Pat. No. 11,415,566.

(30) Foreign Application Priority Data

Dec. 15, 2017 (WO) ................ PCT/US2017/066758

(51) Int. Cl.
*G01N 33/18* (2006.01)
*G01N 29/22* (2006.01)
(Continued)

(52) U.S. Cl.
CPC ...... *G01N 33/1886* (2013.01); *G01M 5/0033* (2013.01); *G01M 5/0066* (2013.01);
(Continued)

(58) Field of Classification Search
CPC ............. G01N 29/225; G01N 35/0099; G01N 21/9515; G01N 21/954; G01N 29/265;
(Continued)

(56) References Cited

U.S. PATENT DOCUMENTS 2,316,835 A 4/1943 Blood
2,743,035 A 4/1956 Fogarty
(Continued)

FOREIGN PATENT DOCUMENTS

CN 205686495 U 11/2016
EP 1197139 A1 4/2002
(Continued)

OTHER PUBLICATIONS

Int'l Search Report & Written Opinion in PCT/US2018/65888, dated Aug. 5, 2018.
(Continued)

*Primary Examiner* — Benjamin R Schmitt
(74) *Attorney, Agent, or Firm* — Crowe & Dunlevy, P.C.

(57) ABSTRACT

A method of retrieving a mobile platform from a tank at least partially filled with a non-conductive, energetic substance includes configuring the mobile platform to include at least a retrieval system including a buoyant body, an electrically conductive member, and a tether. The tether electrically isolates the buoyant body from the enclosure. The method further includes the steps of releasing the buoyant body to convey the tether toward a surface of the non-conductive, liquid energetic substance; conveying an electrically conductive cable to the electrically conductive member using the tether; electrically connecting a voltage neutralizing end
(Continued)

US 11,604,180 B2

Page 2 of the electrically conductive cable to a voltage differential neutralizing body in a spark inhibiting ambient condition; electrically connecting a mobile platform end of the electrically conductive cable to the electrically conductive member of the mobile platform while the electrically conductive member is below the surface of the non-conductive, liquid energetic substance.

10 Claims, 23 Drawing Sheets

(51) Int. Cl.
| | |
|---|---|
| G05D 1/00 | (2006.01) |
| G01M 5/00 | (2006.01) |
| G01N 35/00 | (2006.01) |
| G01N 21/95 | (2006.01) |
| G01N 21/954 | (2006.01) |
| G01N 29/265 | (2006.01) |
| G01S 13/89 | (2006.01) |
| G01S 17/89 | (2020.01) |

(52) U.S. Cl.
CPC ........ *G01M 5/0075* (2013.01); *G01M 5/0091* (2013.01); *G01N 29/225* (2013.01); *G01N 35/0099* (2013.01); *G05D 1/0094* (2013.01); *G01N 21/954* (2013.01); *G01N 21/9515* (2013.01); *G01N 29/265* (2013.01); *G01N 2021/9518* (2013.01); *G01N 2021/9544* (2013.01); *G01N 2291/044* (2013.01); *G01N 2291/2636* (2013.01); *G01N 2291/2695* (2013.01); *G01S 13/89* (2013.01); *G01S 17/89* (2013.01); *G05D 2201/0207* (2013.01)

(58) Field of Classification Search
CPC ....... G01N 33/1886; G01N 2021/9518; G01N 2021/9544; G01N 2291/044; G01N 2291/2636; G01M 5/0033; G01M 5/0066; G01M 5/0075; G01M 5/0091
See application file for complete search history.

(56) References Cited

U.S. PATENT DOCUMENTS

| | | | |
|---|---|---|---|
| 2,801,768 | A | 8/1957 | Immel |
| 2,835,722 | A | 5/1958 | Appleton |
| 3,016,431 | A | 1/1962 | Steigerwald |
| 3,111,863 | A | 11/1963 | Filz |
| 3,362,573 | A | 1/1968 | Wales, Jr. |
| 3,497,638 | A | 2/1970 | Cohen |
| 3,536,158 | A | 10/1970 | Blair |
| 3,607,604 | A | 9/1971 | Nava |
| 3,700,359 | A | 10/1972 | Vanderjagt |
| 3,927,249 | A | 12/1975 | Pearse |
| 3,974,933 | A | 8/1976 | Toth et al. |
| 4,180,177 | A | 12/1979 | Alcock et al. |
| 4,216,349 | A | 8/1980 | Wium |
| 4,328,901 | A | 5/1982 | Gunderman et al. |
| 4,460,826 | A | 7/1984 | Pryor |
| 4,467,136 | A | 8/1984 | Wium |
| 4,557,697 | A * | 12/1985 | Kontar .................. B63C 11/48 441/32 |
| 4,620,061 | A | 10/1986 | Appleton |
| 4,664,281 | A | 5/1987 | Falk et al. |
| 4,668,146 | A | 5/1987 | Ageta |
| 4,676,574 | A | 6/1987 | Grosso et al. |
| 4,706,001 | A | 11/1987 | Nakashima et al. |
| 4,732,526 | A | 3/1988 | Nakashima et al. |
| 4,760,001 | A | 7/1988 | Nann et al. |
| 4,814,651 | A | 3/1989 | Elris et al. |
| 4,961,111 | A | 10/1990 | Herlitz et al. |
| 4,984,449 | A | 1/1991 | Caldwell et al. |
| 4,984,745 | A | 1/1991 | Akeel et al. |
| 4,985,653 | A | 1/1991 | Takagi et al. |
| 5,059,075 | A | 10/1991 | Kelly |
| 5,146,105 | A | 9/1992 | Obata et al. |
| 5,192,194 | A | 3/1993 | Birdwell |
| 5,205,174 | A | 4/1993 | Silverman et al. |
| 5,473,953 | A | 12/1995 | Appel |
| 5,534,664 | A | 7/1996 | Fearing, Jr. et al. |
| 5,627,800 | A | 5/1997 | Kotler et al. |
| 5,819,863 | A | 10/1998 | Zollinger et al. |
| 5,821,695 | A | 10/1998 | Vilanilam et al. |
| 5,833,782 | A | 11/1998 | Crane et al. |
| 5,947,051 | A | 9/1999 | Geiger |
| 6,040,543 | A | 3/2000 | Mina et al. |
| 6,104,970 | A | 8/2000 | Schmidt, Jr. et al. |
| 6,452,163 | B1 | 9/2002 | Frederick et al. |
| 6,477,913 | B1 | 11/2002 | Akeel et al. |
| 6,522,039 | B1 | 2/2003 | Baltz et al. |
| 6,574,652 | B2 | 6/2003 | Burkhard |
| 6,612,168 | B2 | 9/2003 | Barr et al. |
| 6,641,667 | B2 | 11/2003 | Ochiai et al. |
| 7,296,350 | B2 | 11/2007 | Sexton et al. |
| 7,448,597 | B2 | 11/2008 | Jacobson et al. |
| 7,723,614 | B2 | 5/2010 | Zamfes et al. |
| 7,971,497 | B2 | 7/2011 | Gershtein |
| 8,122,780 | B1 | 2/2012 | Zollinger et al. |
| 8,227,692 | B2 | 7/2012 | Dahlgren et al. |
| 9,228,932 | B1 | 1/2016 | Maresca, Jr. et al. |
| 9,519,289 | B2 | 12/2016 | Munich et al. |
| 2002/0043280 | A1 | 4/2002 | Ochiai et al. |
| 2004/0045379 | A1 | 3/2004 | Silverman et al. |
| 2005/0285464 | A1 | 12/2005 | Orders et al. |
| 2006/0010995 | A1 | 1/2006 | Silverman et al. |
| 2006/0066155 | A1 | 3/2006 | Matin et al. |
| 2006/0250025 | A1 | 11/2006 | Kitagawa et al. |
| 2006/0261192 | A1 | 11/2006 | Haas et al. |
| 2006/0278069 | A1 | 12/2006 | Ryan et al. |
| 2007/0156286 | A1 | 7/2007 | Yamauchi |
| 2007/0204675 | A1 | 9/2007 | Herzog et al. |
| 2008/0148876 | A1 | 6/2008 | Hock et al. |
| 2008/0223630 | A1 | 9/2008 | Couture et al. |
| 2008/0255704 | A1 | 10/2008 | Braut |
| 2008/0287050 | A1 | 11/2008 | Krogedal et al. |
| 2008/0294288 | A1 | 11/2008 | Yamauchi |
| 2009/0059492 | A1 | 3/2009 | Glover |
| 2009/0284381 | A1 | 11/2009 | Manahan |
| 2010/0109459 | A1 | 5/2010 | Takahashi |
| 2010/0180672 | A1 | 7/2010 | Zollinger |
| 2010/0242830 | A1 | 9/2010 | Manahan |
| 2010/0307225 | A1 | 12/2010 | Yoshida |
| 2010/0321485 | A1 | 12/2010 | Pool |
| 2011/0154934 | A1 | 6/2011 | Skourup et al. |
| 2011/0169486 | A1 | 7/2011 | Light et al. |
| 2011/0208357 | A1 | 8/2011 | Yamauchi |
| 2012/0125128 | A1 | 5/2012 | Gershtein et al. |
| 2012/0128128 | A1 | 5/2012 | Fewster |
| 2012/0145075 | A1 | 6/2012 | Takahashi |
| 2013/0011234 | A1 | 1/2013 | Pretlove et al. |
| 2014/0137903 | A1 | 5/2014 | Chen et al. |
| 2015/0122288 | A1 | 5/2015 | Eriksson et al. |
| 2015/0148955 | A1 | 5/2015 | Chin et al. |
| 2015/0369751 | A1 | 12/2015 | Cheim et al. |
| 2017/0248554 | A1 | 8/2017 | Fedosovsky et al. |
| 2017/0356639 | A1 | 12/2017 | Taylor et al. |
| 2018/0079475 | A1* | 3/2018 | Trigui .................. G01B 17/02 |
| 2018/0088592 | A1 | 3/2018 | Gildner et al. |

FOREIGN PATENT DOCUMENTS

| | | |
|---|---|---|
| EP | 2069112 A1 | 6/2009 |
| EP | 2184140 A1 | 5/2010 |
| EP | 2418926 A2 | 2/2012 |
| EP | 2762279 A1 | 8/2014 |
| JP | 10238699 A | 9/1998 |
| JP | 2007147506 A | 6/2007 |
| JP | 2014111668 A | 6/2014 |
| WO | 2000055594 A2 | 9/2000 |
| WO | 2004018327 A2 | 3/2004 |

(56) References Cited

FOREIGN PATENT DOCUMENTS

| WO | 2010103426 A1 | 9/2010 |
|---|---|---|
| WO | 2011084143 A1 | 7/2011 |
| WO | 2012145745 A1 | 10/2012 |
| WO | 2016073244 A1 | 5/2016 |
| WO | 2016085717 A1 | 6/2016 |
| WO | 2017003758 A1 | 1/2017 |
| WO | 2019035856 A1 | 2/2019 |

OTHER PUBLICATIONS

Int'l Search Report & Written Opinion in PCT/US17/66758, dated Aug. 30, 2018.
Int'l Search Report & Written Opinion in PCT/US19/18788, dated Oct. 25, 2019.
Hagen Schemptf et al, "Neptune: Above-Ground Storage Tank Inspection Robot System", IEEE Robotics & Automation Magazine, vol. 2, No. 2, Jun. 1, 1995, pp. 8-15, ISSN: 1070-9932, IEEE Service Center, Piscataway, NJ, US.
Comments to Written Opinion in PCT/US19/18788, submitted Feb. 10, 2020.
Int'l Preliminary Examination Report on Patentability in PCT/US19/18788, dated Jun. 8, 2020.
PetRobot, webpage priintout, can be found at petrobotproject.eu/robotic-inspection-technology, 3 pp. (Jun. 18, 2020).
MantaRobotics webpage printout, located at Mantarobotics.com/anatomy-of-a-robotic-tank-inspection, 2 pp. (Jun. 18, 2020).
SOLEX webpage printout, located at www.solexrobotics.com/solex7.html, 3 pp. (Jun. 18, 2020).
Online Tank Services, webpage printout, located online at A. HAK Industrial Services, 7 pp. (Jun. 18, 2020).
Energy Services, online Storage Tank Floor Inspection, webpage printout, located at www.diakont.com/energy_services/online_storage_inspection.html, 3 pp. (Jun. 18, 2020).
Int'l Search Report & Written Opinion in PCT/US2020/037475 dated Mar. 2, 2021.

\* cited by examiner

VOLTAGE DIFFERENTIAL REDUCTION METHODS USED WHILE RETRIEVING A MOBILE PLATFORM FROM A TANK CONTAINING A HAZARDOUS, NON-CONDUCTIVE SUBSTANCE

TECHNICAL FIELD

Generally, this disclosure relates to devices and related methods for handling a mobile platform in a tank containing hazardous substances that may be non-conductive.

BACKGROUND

Otherwise routine tasks may become exceedingly difficult if the ambient conditions pose a potential hazard to humans and/or the machinery required to perform those tasks. One such task is inspecting the structural integrity of tanks used to contain flammable substances such as liquid or gaseous hydrocarbons. Tank inspections typically include measuring the wall thicknesses at multiple locations of the tank structure. An out-of-norm thickness indicates the presence of corrosion, or some other type of damage, which left unchecked could create leak paths for the resident fluids. Unfortunately, inspections of walls making up a bottom or floor of a tank must be conducted from the interior of the tank in order to accurately assess the condition of these walls.

A common approach to performing tank inspections is to use human work crews who enter the tank interior and scan the floors of tanks using magnetic and ultrasonic sensors. The tank must first be emptied of liquid contents and purged of all flammable substances to a sufficiently low concentration so that any sparks caused by equipment used by the work crews do not cause an explosion. The preliminary step of purging the tank is time consuming. Moreover, the tank must be decommissioned and taken out of service during the entire inspection process. Thus, manual tank inspections can be costly and disruptive to the ongoing operations of tank owners.

A recently developed method to inspect tanks proposed by PETROBOT utilizes a remotely operated inspection device that can scan the bottom of tanks. A flexible umbilical physically and operationally connects the inspection device to a control unit, which is positioned outside of the tank. An inert gas, such as nitrogen, is pumped via the umbilical into the inspection device before and while the inspection device is in the tank. The inert gas, which displaces the oxygen inside the inspection device, is believed to minimize the likelihood of a spark igniting the flammable substance. The umbilical is also used for bi-directional communication. Data collected by the inspection device can be transmitted via the umbilical to the external control unit. A human operator at the external control unit transmits control signals via the umbilical to steer the inspection device. In addition to gas and signals, electrical power is conveyed by the umbilical. This system may eliminate the need for human work crews inside the tank.

However, remotely operated inspection devices such as the PETROBOT device appear to be labor intensive to operate due to, for example, human control of steering during inspection operations. Moreover, the need for an opening to accommodate the umbilical during operation presumably exposes the outside environment to the hazardous materials inside the tank. Thus, the need remains to more efficiently and safely conduct inspections of tanks used to contain flammable material.

In some aspects, the present disclosure addresses these and other drawbacks of systems and methods for performing tank inspections in an environment having flammable or combustible substances. However, inspections of wall thicknesses of a tank containing a flammable substance is only illustrative of the general problem of performing tasks in an environment that may be harmful to humans and/or machinery. For example, toxic materials, while not necessarily flammable, may pose difficulties when conducting manufacturing or processing operations. Therefore, in further aspects, the present disclosure addresses the need to more efficiently and safely perform one or more tasks in a hazardous environment.

Some ambient conditions may include energetic substances that may also be non-conductive. The non-conductivity of an environment in which machinery is to be used may pose additional considerations in handing and operating such machinery. For example, the non-conductive environment may not allow an electrical charge that accumulates on machinery during operation to dissipate prior to retrieval. This accumulated electrical charge may cause a spark if the machinery is sufficiently close to a body with which it has a voltage differential. Such a spark may ignite an energetic substance, if present.

In aspects, the present disclosure addresses these and other drawbacks of systems and methods that utilize machinery in an environment having energetic substances that may be non-conductive. In some aspects, the present disclosure addresses such drawbacks by controlling electrical charge accumulation on such machinery. In some aspects, the present disclosure addresses such drawbacks by reducing an accumulated electrical charge on such machinery prior to or during retrieval.

Tanks are sometimes specifically designed to restrict access into an interior in which substances are stored in order to provide a sealed or isolated environment of such substances. For example, a tank may include a relatively small hatch, which is easily sealed, to allow personnel to access the tank interior. Personnel may encounter difficulties in reaching locations that are not in the immediate vicinity of that hatch.

In some aspects, the present disclosure addresses the drawbacks of systems and methods for deploying and retrieving equipment used in containers, such as tanks, that have limited access to interior locations in such containers. In some aspects, the present disclosure addresses the drawbacks of systems and methods for handling and retrieving machinery having an accumulated electrical charge due to use in containers that store non-conductive substances.

SUMMARY

The present disclosure, in part, relates to methods and related systems for handling a mobile platform in a tank containing non-conductive hazardous substances. By "non-conductive" or "electrically non-conductive," it is meant an electrical conductivity less than 1,000 picosiemens per meter (pS/m). By way of comparison, common drinking water is more than one thousand times as conductive as a substance defined as non-conductive in this disclosure.

In still further aspects, the present disclosure provides methods for retrieving a mobile platform from a tank containing non-conductive hazardous substances. An illustrative method of retrieving a mobile platform from a tank having a hatch and at least partially filled with a non-conductive, energetic substance may include the step of: configuring the mobile platform to include at least: an enclosure, at least one control unit positioned inside the enclosure, at least one propulsion system positioned at least partially inside the enclosure, at least one power supply positioned inside the enclosure, and at least one retrieval system disposed at least partially on the enclosure and including at least: at least one buoyant body, at least one primary tether connected to the at least one buoyant body and to the enclosure; at least one secondary tether connected to the at least one buoyant body and to the enclosure.

The method may further include the steps of: predetermining a buoyant body retrieval zone within the tank, wherein the buoyant body retrieval zone is below the hatch; lowering the mobile platform into the tank using a deployment carrier; submerging the enclosure in a non-conductive, liquid energetic substance; moving the mobile platform using the propulsion system to perform at least one task in the tank; releasing the at least one buoyant body and the at least one primary tether from the enclosure; positioning the released at least one buoyant body within the buoyant body retrieval zone by using the at least one primary tether; accessing the at least one buoyant body through the hatch; retrieving the at least one primary tether by using the at least one buoyant body; using the at least one primary tether to release the at least one secondary tether; and inserting a retrieval member through the hatch to retrieve at least one of: (i) the at least one buoyant body, (ii) the at least one primary tether, and (iii) the at least one secondary tether.

In further aspects, the present disclosure provides methods for neutralizing charge accumulation on a mobile platform in a tank containing non-conductive hazardous substances. An illustrative method of retrieving a mobile platform from a tank at least partially filled with a non-conductive, energetic substance may include the steps of: configuring the mobile platform to include at least: an enclosure, at least one control unit positioned inside the enclosure, at least one propulsion system positioned at least partially inside the enclosure, at least one power supply positioned inside the enclosure, at least one retrieval system disposed at least partially on the enclosure, the at least one retrieval system including at least one buoyant body, an electrically conductive member, and at least one tether, the at least one tether having a portion that is not conductive, the at least one tether electrically isolating the at least one buoyant body from the enclosure; lowering the mobile platform into the tank using a deployment carrier; submerging the enclosure in a non-conductive, liquid energetic substance; and moving the mobile platform using the propulsion system to perform at least one task in the tank.

The method may further include the steps of releasing the buoyant body to convey the at least one tether toward a surface of the non-conductive, liquid energetic substance; conveying an electrically conductive cable to the electrically conductive member of the mobile platform using the at least one tether; electrically connecting a voltage neutralizing end of the electrically conductive cable to a voltage differential neutralizing body in a spark inhibiting ambient condition; electrically connecting a mobile platform end of the electrically conductive cable to the electrically conductive member of the mobile platform while the electrically conductive member is below the surface of the non-conductive, liquid energetic substance; and retrieving the mobile platform from inside to outside of the tank.

In aspects, the present disclosure provides methods for controlling charge accumulation on a mobile platform in a tank containing non-conductive hazardous substances. An illustrative method of operating a mobile platform in a tank at least partially filled with a non-conductive, energetic substance may include the steps of: configuring the mobile platform to include at least: an enclosure, at least one control unit positioned in the enclosure, at least one propulsion system at least partially positioned in the enclosure, at least one electrical power supply positioned in the enclosure, wherein a power supplied from the at least one electrical power supply to at least one electrical power consumer associated with the mobile platform adds an electrical charge to the mobile platform), at least one retrieval system disposed at least partially on the enclosure and including at least one buoyant body, and at least one charge accumulation control system disposed at least partially on the enclosure, the at least one charge accumulation control system being configured to control an accumulation of the electrical charge on the mobile platform by one of: (i) reducing the supplied power and preventing an increase in the supplied power later while the mobile platform is inside the tank, and (ii) disengaging the at least one electrical power consumer from the supplied power and preventing a reengagement of the supplied power with the at least one electrical power consumer later while the mobile platform is inside the tank; lowering the mobile platform into the tank using a deployment carrier; submerging the enclosure in a non-conductive, liquid energetic substance; and moving the mobile platform using the propulsion system to perform at least one task in the tank.

The method may further include the steps: controlling the electrical charge accumulation on the mobile platform using the at least one charge accumulation control system and indicating an activation state of the charge accumulation control system by releasing at least one buoyant body from the enclosure, the activation state being one of: (i) prior activation of the charge accumulation control system, and (ii) activation of the charge accumulation control system after a predetermined time delay; and retrieving the mobile platform from inside to outside of the tank.

The above-recited example of features of the disclosure have been summarized rather broadly in order that the detailed description thereof that follows may be better understood, and in order that the contributions to the art may be appreciated. There are, of course, additional features of the disclosure that will be described hereinafter and which will form the subject of the claims appended hereto.

BRIEF DESCRIPTION OF THE DRAWINGS

For detailed understanding of the present disclosure, references should be made to the following detailed description of the disclosure, taken in conjunction with the accompanying drawings, in which like elements have been given like numerals and wherein.

DETAILED DESCRIPTION

The present disclosure provides devices, systems, and methods for performing tasks in a hazardous environment. For conciseness and clarity, the description below is principally directed to systems and related methods for inspecting a tank structure having an interior in which energetic materials such as hydrocarbon fluids are present. The present disclosure also provides devices, systems, and methods for handling mobile platforms used in a non-conductive, energetic substance. For conciseness and clarity, the description below is principally directed to systems and related methods for handling mobile platforms in a tank structure having an interior in which non-conductive, energetic substances, such as some classes of hydrocarbon liquids and gases, are present. However, it is emphasized that the present teachings can be readily applied to other industries and uses.

Figure 1:
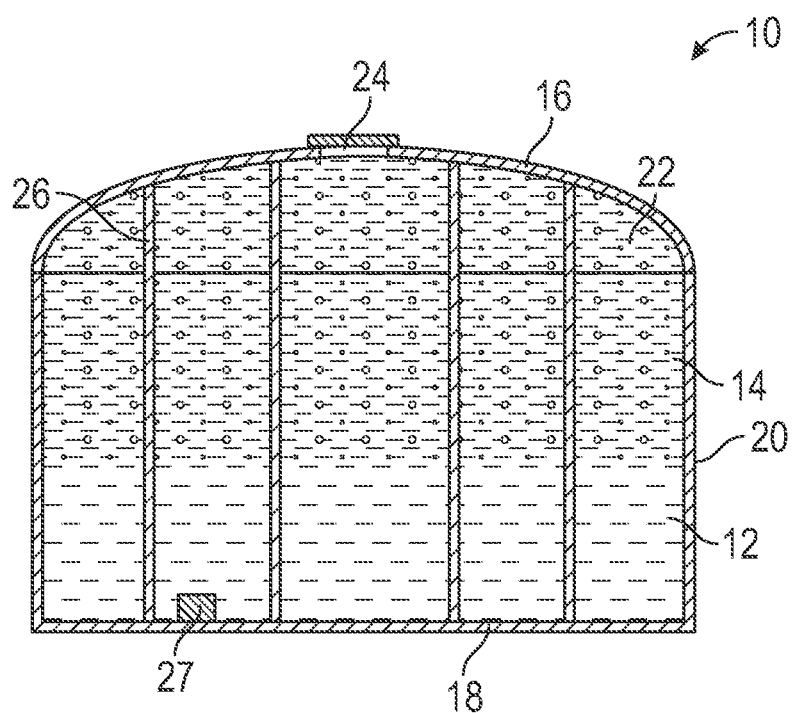
FIG. 1 sectionally illustrates a tank that may be inspected by using a mobile platform according to the present disclosure.

Referring initially to FIG. 1, a tank 10 may be used to store an energetic substance, such as hydrocarbons, in the form of a liquid body 12 and a vapor 14. The fluid-tight tank may include a domed top wall 16, a generally planar bottom wall 18, and a cylindrical vertical wall 20. An interior 22 of the tank 10 may be accessed via a hatch 24. In some tanks, pillars 26 may be used for structural support or other uses. Also, it is common for the tank 10 to also contain objects 27, which may be intentionally placed such as sumps, piping, supports, etc. or foreign material such as debris, dropped tools, chains, wires, etc. The tank 10 may be a fixed above-ground tank or an underground tank. The tank 10 may also be positioned on a vehicle or vessel such as a barge, ship, land vehicle, etc. Moreover, the tank 10 may employ different configurations; e.g., the top wall 16 may be flat and/or an interior floating roof may be used. As will be evident from the discussion below, systems and methods of the present disclosure can perform inspections of the tank 10, and other similar structures irrespective of their usage, location, or design, with greater efficiency and safety than conventional tank inspection devices and methods.

Figure 2:
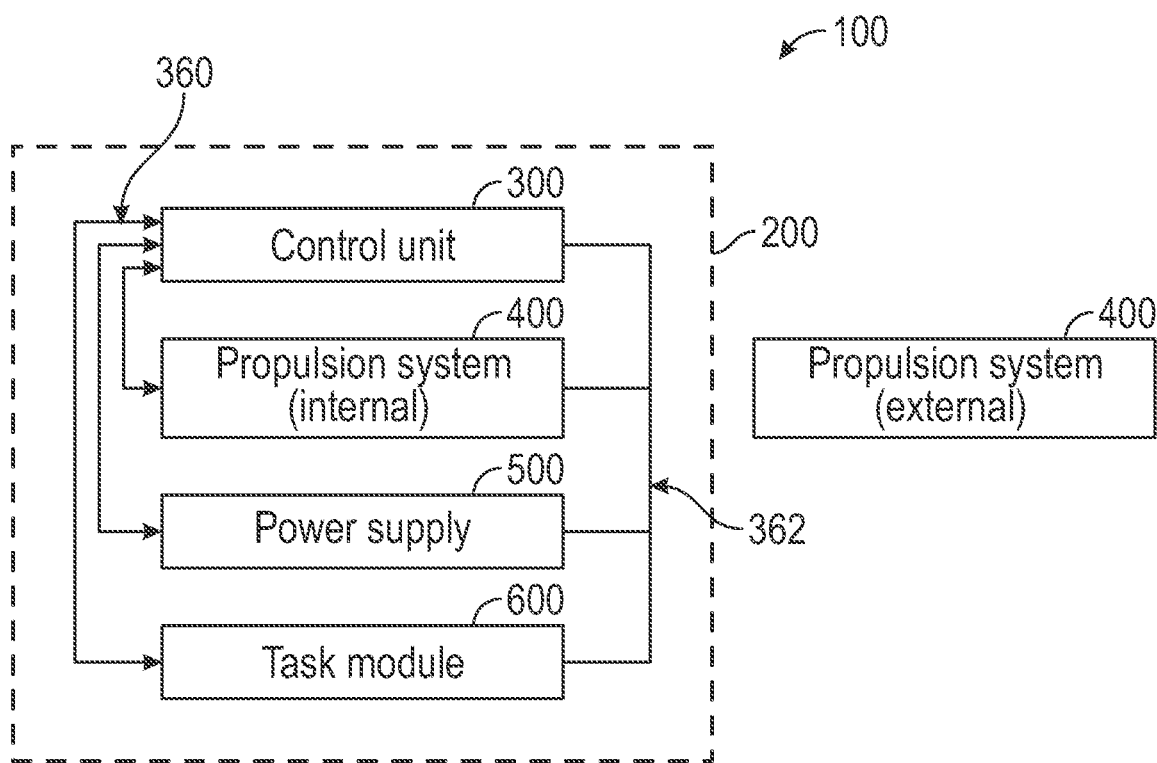
FIG. 2 is a functional block diagram of one embodiment of a mobile platform in accordance with the present disclosure.

Referring now to FIG. 2, there is shown, in functional block diagram format, a non-limiting embodiment of an intelligent mobile platform 100 for performing one or more tasks in the tank 10 of FIG. 1. The mobile platform 100 may include an enclosure 200, a control unit 300, a propulsion system 400, and a power supply 500. Optionally, a task module 600 may also be carried by the mobile platform 100. As used herein, the term "carried by" means that the object is inside, attached to, or on the mobile platform 100. Hereafter, these structures and on-board equipment will collectively be referred to as "subsystems." In some embodiments, the control unit 300 has bi-directional communication with one or more subsystems via a communication network 360. In other embodiments, communication may be in one direction to one or more subsystems. In still other embodiments, no communication is provided to or from some of the subsystems. The power supply 500 supplies power to one or more systems via a power distribution network 362, which may share circuitry with the communication network 360. The mobile platform 100 may be considered "intelligent" because the control unit 300 is configured to control the subsystems of the mobile platform 100 by using only previously programmed instructions and information acquired "real time" or "near real time" via on-board sensing instruments. That is, the mobile platform 100 can acquire information relevant to an assigned task and make decisions in furtherance of the completion of that task without human intervention. Therefore, advantageously, the mobile platform 100 may not have and may not require any umbilical, physical or otherwise, to a location external to a tank through which power or command signals are received. The subsystems of the mobile platform 100 are discussed in greater detail below.

Generally, the mobile platform 200 is configured to be inherently safe. By "inherently safe," it is meant that the mobile platform 200 is designed such that at no time during operation in the tank 10 (FIG. 1) will a spark from the mobile platform 200 come into contact with the energetic substance outside of the mobile platform 200. An element of the "inherently safe" design is that the enclosure 200 incorporates structural features that prevent a spark, or a spark from an explosion of the energetic substance 12, 14, or a spark from an explosion of another energetic substance similar to the energetic substance 12, 14, occurring inside the enclosure 200 under normal operating and standard atmospheric conditions (i.e., twenty degrees Celsius (sixty-eight degrees Fahrenheit) and 1.01325 bar) from passing to an exterior of the enclosure 200. Another energetic substance is considered to be "similar" to the energetic substance 12, 14 if such other energetic substance has a Maximum Experimental Safe Gap (MESG) in the same class as the energetic substance 12, 14 (such class specified as: i. less than or equal to 0.45 mm (17.72 mils), ii. greater than 0.45 mm (17.72 mils) and less than or equal to 0.75 mm (29.53 mils), or iii. greater than 0.75 mm (29.53 mils)) and/or has a Minimum Igniting Current Ratio (MICR) in the same class as the energetic substance 12, 14 (such class specified as: i. less than or equal to 0.4, ii. greater than 0.4 and less than or equal to 0.8, or iii. greater than 0.8).

An "intrinsically safe" component is one that cannot create a spark when used as intended for the purpose for which the component was designed. A "non-intrinsically safe" or "spark-generating" component may generate a spark when operated as intended. The interior of the enclosure 200 houses all components of a device, assembly, or subassembly that are not intrinsically safe; i.e., all "spark-generating" components. Thus, the enclosure 200 may be considered an "inherently safe" structure.

Generally, "spark-generating components" include mechanical structures that move fast enough to cause a spark and electrical components that operate at sufficiently high energy state to cause sparking. Generally, "non spark-generating components" include mechanical structures that do not move fast enough to cause a spark and electrical components that operate at sufficiently low energy state to preclude sparking. It should be noted that some subsystems may include spark-generating and non-spark-generating components. The mobile platform 100 is designed such that spark-generating components of such subsystems are positioned inside the enclosure 200. The non-spark-generating components of such subsystems may be positioned internal or external to the enclosure 200. By way of example, the propulsion system 400 has spark-generating components isolated inside the enclosure 200 and intrinsically safe external components external to the enclosure 200.

As described below, the enclosure 200 uses construction techniques and materials that ensure that sparks from a spark-generating component, or sparks from explosions caused by such sparks, do not pass to the exterior of the enclosure 200 and ignite any ambient energetic material.

Figure 3A:
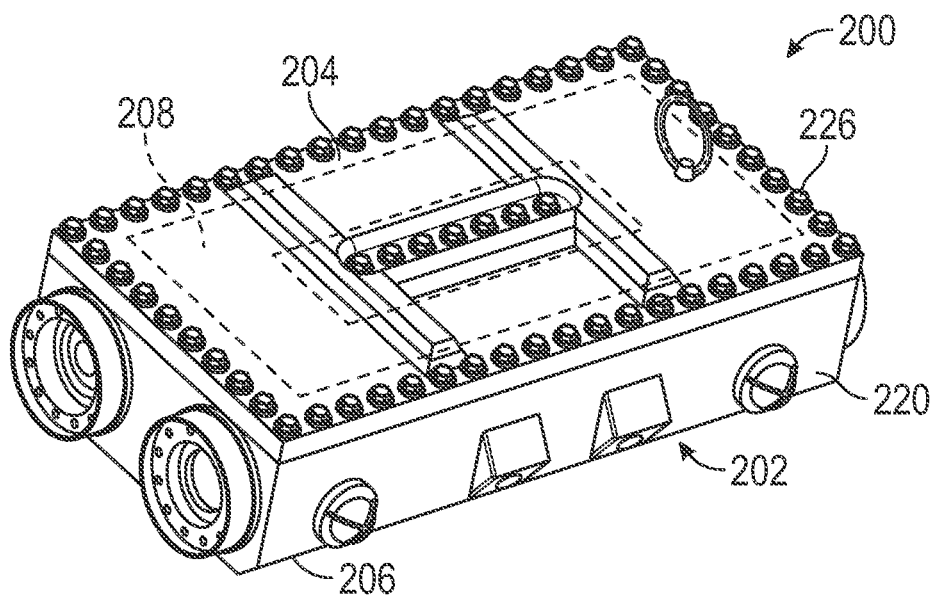
FIGS. 3A-C illustrate one embodiment of an enclosure for a mobile platform according to the present disclosure.

Referring to FIG. 3A, there is shown one enclosure 200 according to the present disclosure. While the enclosure 200 is shown as a single integral body, the enclosure 200 may have two or more separate and fully self-contained bodies. The enclosure 200 includes a shell 202 and a top lid 204. The shell 202 is defined by a side wall 220 and a bottom 206, which collectively define an interior 208. The vertical wall 220 and bottom 206 may be formed as an integral body or an assembly of individual walls. The outer shell 200 may be formed as an elongated box. However, other shapes, and combination of shapes, such as spherical, frustoconical, or cylindrical may be used. Moreover, the enclosure 200 may incorporate planar, curvilinear, and/or asymmetric geometries. Suitable materials for the enclosure 200 include metals, alloys, polymers, glass, composites, and combinations thereof. Additionally, the enclosure 200 may be liquid-tight so that the mobile platform 100 (FIG. 2) can be partially or fully submerged in the liquid body 12 (FIG. 1) inside the tank 10 (FIG. 1).

Figure 3B:
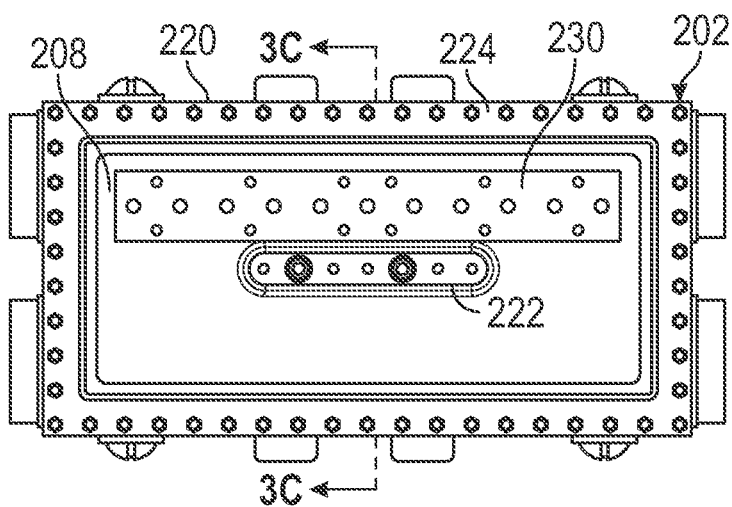

Referring to FIG. 3B, the walls 220 and internal structures of the enclosure 200 may use a range of thicknesses. The walls may be formed as plates, ribs, meshes, etc. Selected areas may be strengthened using reinforcement members such as steel rings (not shown). In some situations, it may be desirable that the enclosure 200 use features such as fillets and symmetric arrangements to manage or control stress concentrations in the enclosure 200. For example, the interior 208 is symmetrically arranged in the longitudinal and transverse axes. Depending on the application, the symmetry may be along one, two, or three axes. For purposes of the present disclosure, the symmetry does not require identical features (e.g., volumes or dimensions) on each side of an axis. Rather, the interior 208 may be considered symmetric if both sides of an axis cause a spark or related explosion to dissipate in generally the same manner (e.g., rate of propagation/dissipation, direction of movement, etc.).

The enclosure 200 may also use structures that disrupt detonation paths such as interior baffles, orthogonal corners, and shields in front of relatively weak wall sections and/or portals or other passages leading to the exterior of the enclosure 200. For example, a majority of corners of the shell 202 that define the interior 208 can have a ninety-degree angle. Other arrangements may have more than sixty percent or eighty percent of such corners having a ninety-degree angle. Additionally, one or more interior plates 222 may be positioned to divide the volume of the interior 208 to reduce the length of pathways that pressure waves can travel unobstructed across the interior 208. These interior plates 222, which may be referred to as baffles or blast shields, create circuitous paths that can dissipate shock waves.

Figure 3C:
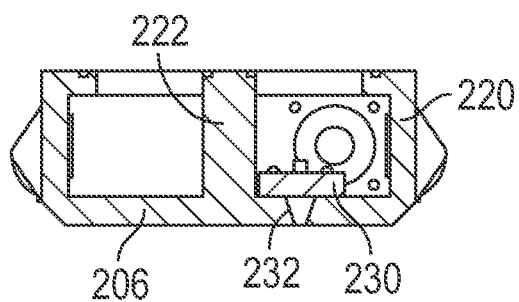

Referring to FIGS. 3A-C, in embodiments, the lid 204 may be removably affixed to a top surface 224 of the vertical wall 220 with a plurality of fastening elements 226. The fastening elements 226 may be distributed continuously along a perimeter of the lid 204 to provide a nearly uniform compressive/clamping force that secures the lid 204 to the shell 202. In some arrangements, the fastening elements 226 are spaced apart such that the interstitial length is at a defined maximum fraction of a length along which the fastening elements 226 are distributed. For example, if the defined maximum fraction is one-twentieth and the length of a perimeter along which the fastening elements 226 are distributed is one meter, then fastening elements 226 are distributed such that no fastening element 226 is more than five centimeters from one another fastening element 226. In embodiments, the maximum defined fraction may be one-half, one-quarter, one-fifth, an eighth, or a tenth of a length along which the fasteners are distributed. A fastening element 226 may be any member that connects to the shell 202 and applies a compressive force that presses the lid 204 against the shell 202. Fastening elements 226, include screws, bolts, clamps, rivets, etc.

In one embodiment, the enclosure 200 incorporates one or more of the above described structural features, and/or other known structural features, to prevent permanent structural deformation upon encountering a specified pressure for a specified time in the interior 208 of the enclosure 200. The specified pressure and duration may be based on the anticipated use for the mobile platform 100 and selected to simulate a maximum stress imposed on the enclosure 200 should an explosion occur during operation. In some applications, a "permanent structural deformation" is a plastic deformation that forms a path between the interior 208 and an exterior of the enclosure 200. The path, which may be caused by a loosening of joints or bursting of the enclosure 200, may allow a spark to be communicated to the exterior of the enclosure 200. In embodiments, the specified pressure and duration may be at least ten bars for at least ten seconds, a pressure of at least eight bars for at least eight seconds, a pressure of at least six bars for least six seconds, a pressure of three and one-half bars for at least ten seconds, or a pressure of at least four bars for at least four seconds.

In addition to pressure resistance, the enclosure 200 may incorporate further features to allow operations in particular types of tanks. Referring to FIG. 1, the mobile platform 100 may be sized for entry into and out of a tank 10 having openings and associated hatches 24 of different shapes and relatively limited sizes. The dimensions of openings and related reinforcement structures take into account fall protection, anchorage, hoisting, or personnel retrieval. Experienced engineers may size openings as appropriate for a particular application. Nevertheless, some standardized openings are used. For example, some parallelogram-shaped openings may have maximum dimensions of 36 inches (914.4 mm) by 72 inches (1,828.8 mm). Other parallelogram-shaped openings may have maximum dimensions of 36 inches (914.4 mm) by 36 inches (914.4 mm). Also, some circular openings may have a maximum diameter of 23.62 inches (600 mm), 24 inches (609.4 mm), or 36 inches (914.4 mm). Therefore, in embodiments, mobile platforms 100 of the present disclosure may be sized to pass through a parallelogram-opening having a width no larger than 36 inches (914.4 mm) and a length no larger than 72 inches (1,828.8 mm) or a width no larger than 36 inches (914.4 mm) and a length no larger than 36 inches (914.4 mm). In other embodiments, mobile platforms 100 of the present disclosure may be sized to pass through a circular opening no larger than 36 inches (914.4 mm) in diameter, a circular opening no larger than 24 inches (609.6 mm) in diameter, or a circular opening no larger than 600 mm (23.62 inches) in diameter.

Further, in embodiments, the overall weight of the mobile platform 200 may be maintained at or below a value that could impose difficulties during handling or damage the bottom wall 18 of the tank 10. In embodiments, the overall weight of the mobile platform 100 may be below 10,000 pounds (4,536 kg). In other embodiments, the overall weight of the mobile platform 100 may be below 6,000 pounds (2,722 kg).

Thus, the construction of the enclosure 200 may be bounded by pressure resistance requirements, maximum size requirements, and maximum weight. Construction techniques for making enclosures resistant to rapid increases in pressure are known in the art; e.g., U.S. Pat. No. 2,801,768, Explosion-proof Enclosure; U.S. Pat. No. 6,452,163, Armored Detector Having Explosion Proof Enclosure; U.S. Pat. No. 8,227,692, Explosion-Proof Enclosure; WO 2017003758, Improved Explosive-Proof Thermal Imaging System; and EP 2418926, Sheet Metal Explosion-Proof and Flame-Proof Enclosures. Thus, for conciseness, details of such construction features will not be discussed in further detail. It is emphasized that the above-described construction techniques are merely illustrative of known techniques for configuring the enclosure 200 to be inherently safe. Enclosures 200 encompassed by the present disclosure may incorporate some or all of the above-features or incorporate only other known construction techniques.

Additionally, the enclosure 200 may include two or more separate housing structures. These structures may have the same or similar features and house spark-generating components. For example, one or more additional separate enclosures may house lights and associated batteries to assist with camera images, sensors, tooling, etc. The additional enclosure(s) may be bolted onto the enclosure 200, attached with a tether, towed separately in a wagon type of arrangement, or otherwise physically connected.

Figure 4:
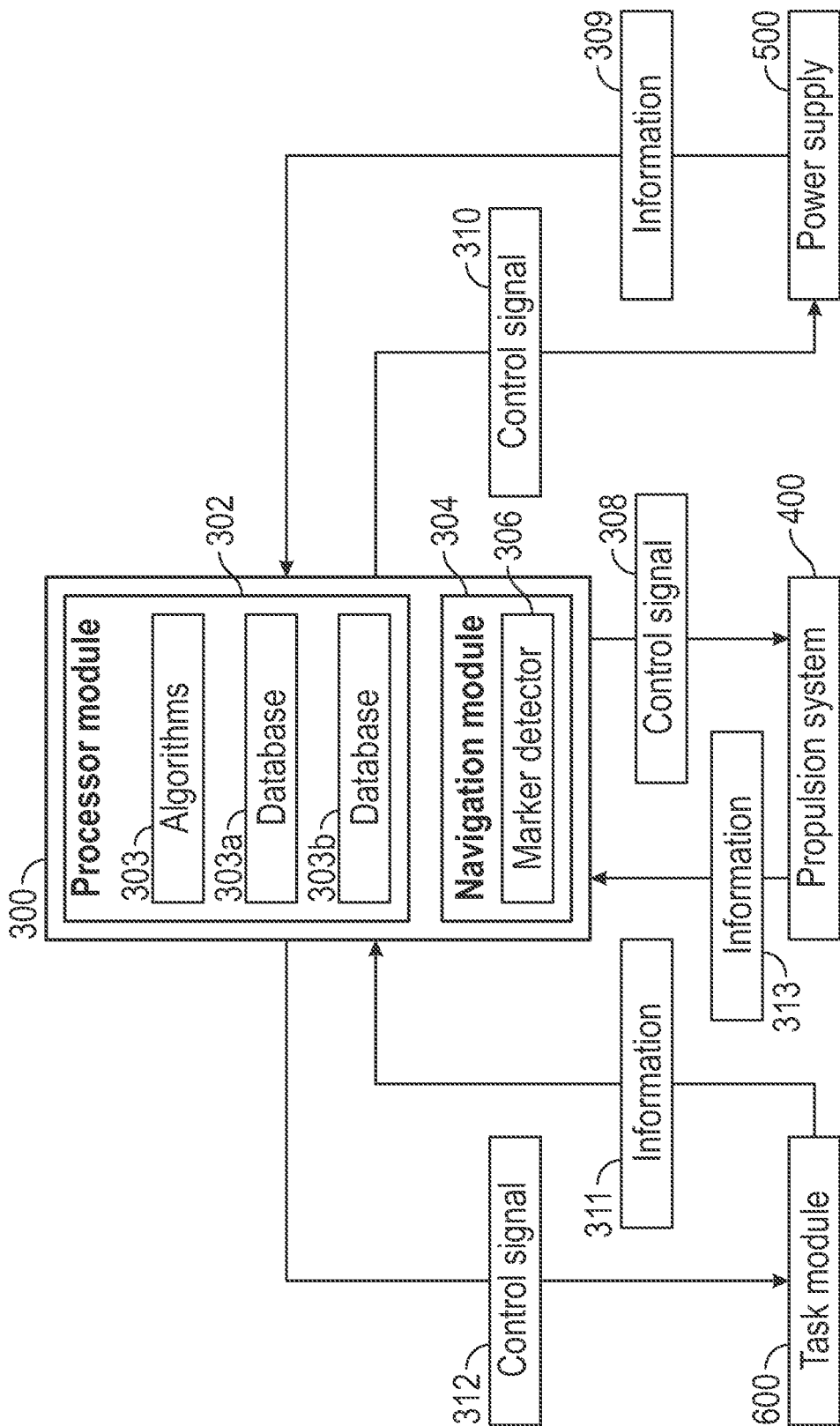
FIG. 4 is a functional block diagram of a control unit and certain related elements for a mobile platform according to one embodiment of the present disclosure.

Referring to FIG. 4, there is shown one non-limiting embodiment of an intelligent control unit 300 that is programmed to control one or more functions of the mobile platform 100 (FIG. 2). The control unit 300 may include a processor module 302 and a navigation module 304. While the control unit 300 may be discussed in the singular, it should be understood that the control unit 300 may be configured as a group of two or more discrete programmed processing devices that work independently or collectively. Moreover, these discrete processing devices may be either distributed throughout the enclosure 200, in separate enclosures, or centralized in one location.

The processor module 302 may include pre-programmed algorithms 303 for controlling some or all of the mobile platform 100. By way of example and not limitation, these algorithms 303 may be executed to issue control signals 308 for operating the propulsion system 400, control signals 310 to manage the power supply 500, and control signals 312 for operating one or more task modules 600. For example, information 309 relating to the power supply 500 may be used to manage power distribution. As used herein, an algorithm means instructions stored in a memory module that can be accessed and implemented by a processor-based machine. The processor module 302 may use conventional micro-processors, memory modules that store one or more databases, 303a,b and other known components of information processing devices.

The navigation module 304 may be configured to acquire information that may be used to determine a position of the mobile platform 100 and/or a position relative to a feature associated with a tank 10 (FIG. 1) and/or an orientation of the mobile platform 100. For brevity, the term "position" is inclusive of an orientation (e.g., heading, tilt, azimuth, etc.) and location (i.e., a point relative to an external reference frame such as a Cartesian coordinate system or a polar coordinate system). A "relative" position is a position identified by referencing a previous position. In one embodiment, the navigation module 304 may include a marker detector liquid that generates signals in response to a detected feature associated with the tank 10 (FIG. 1). The marker detector 306 may be passive or active as discussed in connection with FIGS. 5A-E below. The feature may be either structural or added to the tank 10 (FIG. 1). One non-limiting example of such a feature is a discontinuity found at the juncture of two or more steel plates from which a tank wall is formed; e.g., the bottom wall 18 shown in FIG. 1. The marker detector embodiments discussed herein below use different techniques to detect the discontinuity, which manifests itself as a change in a material property, composition, and/or dimension.

Figure 5A:
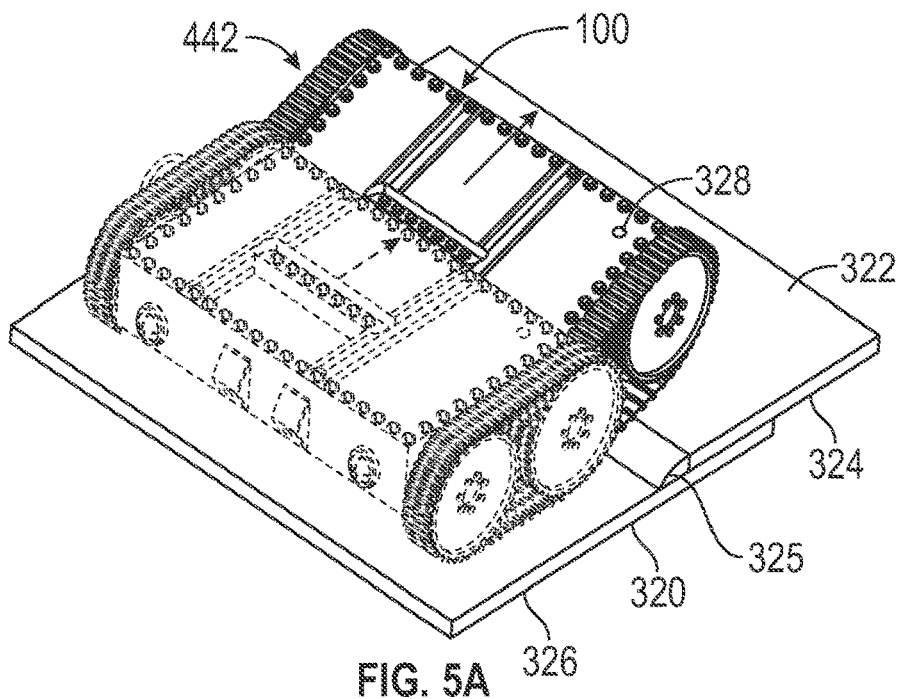
FIGS. 5A-E illustrate embodiments of a marker detector that detects markers according to the present disclosure.

Referring to FIGS. 5A-E, there are shown five non-limiting detector arrangements for detecting features such as discontinuities. FIG. 5A illustrates the mobile platform 100 during contact with a discontinuity 320 on an inner surface 322 of a tank 10 (FIG. 1). The mobile platform 100 prior to encountering the discontinuity 320 is shown in dashed lines. The discontinuity 320 may include a weld seam 325 at a juncture of two overlapping plates 324, 326. The mobile platform 100 may have a marker detector 306 (FIG. 4) that senses orientation, such as an inclinometer 328. Other orientation sensing devices may include accelerometers and gyroscopes. During contact with the discontinuity 320, the inclinometer 328 will sense a change in inclination and generate a responsive signal. The control unit 300 (FIG. 4) can process the signal to determine if the detected signals are indicative of a juncture between two plates or some other discontinuity. The FIG. 5A arrangement may be considered a passive system because no energy is emitted to detect the discontinuity 320.

Figure 5B:
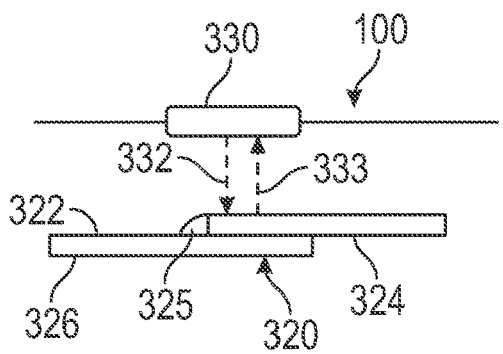

In FIG. 5B, the mobile platform 100 includes a signal emitter 330 that emits an energy wave 332 that interacts with the discontinuity 320. The returning waves 333 from the discontinuity 320 may be detected by the signal emitter 330, in the case of a transducer, or a separate detecting device. Different discontinuities 320 may each uniquely affect the emitted signal. That is, a change in material thickness or material composition may affect the emitted signal differently from variations along a surface (e.g., a protrusion, recess, cavity, etc.). The detected returning waves 333 can be processed to determine if the detected signals are indicative of a juncture between two plates or some other discontinuity. The FIG. 5B arrangement may be considered an active system because energy is emitted to detect the discontinuity 320.

Figure 5C:
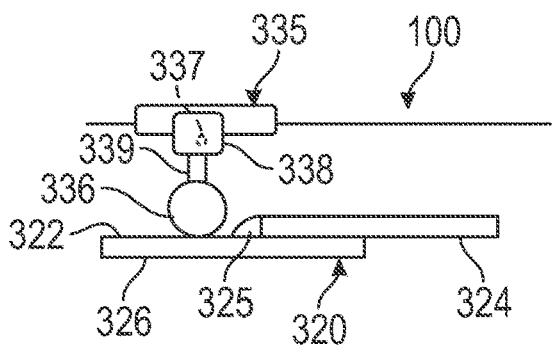

In FIG. 5C, the mobile platform 100 includes a tactile detector 335 that physically contacts the surface 322 and detects characteristics such as a change in inclination, clearance, or roughness that are indicative of the discontinuity 320. In one embodiment, the tactile sensor 335 may "feel" the contour by using a ball wheel 336 pushed down by gravity, or using a biasing member, to trace the surface 322. A sensor 337, such as a Hall sensor, inside a supporting vertical tube 338 may sense the movement up and down of a supporting shaft 339. Other tactile detectors 335 may measure a deflection, bend, or other deformation in a member (not shown) contacting the surface 322.

Figure 5D:
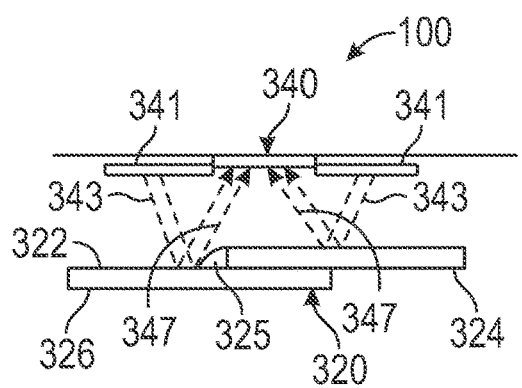

In FIG. 5D, the mobile platform 100 includes an optical detector 340 that optically scans the surface 322 and detects visual characteristics that are indicative of the discontinuity 320. In one embodiment, a light source 341, which may be positioned in one or more external enclosures (not shown), emits light 343 that illuminates the surface 322. The optical detector 340 can record the reflected light 347 for processing and analysis.

Figure 5E:
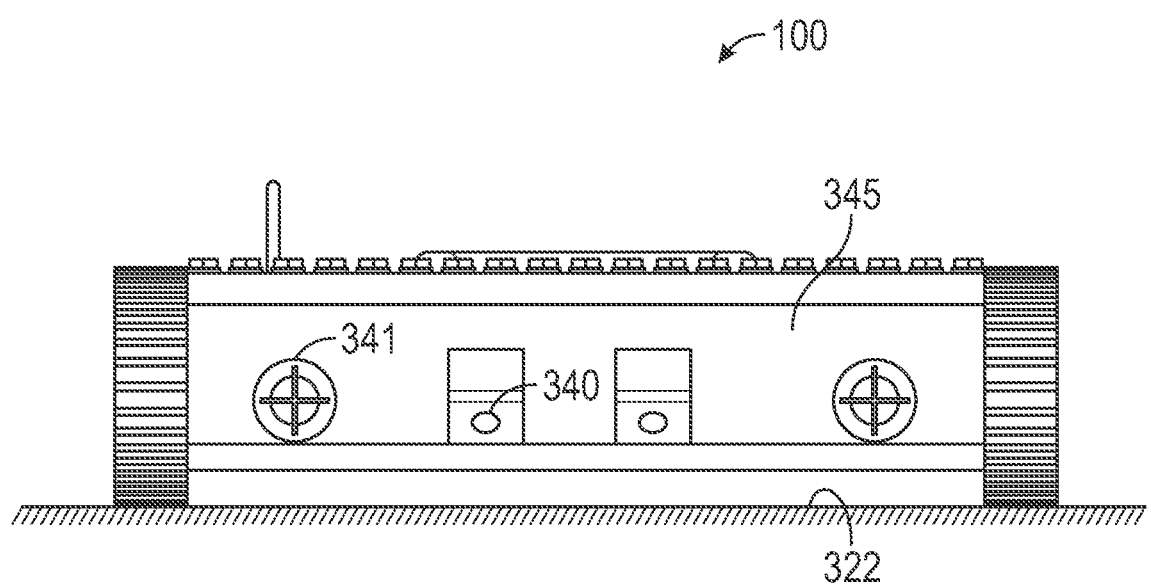

FIG. 5E illustrates another embodiment wherein the mobile platform 100 includes an optical detector 340 that optically scans the surface 322 and detects visual characteristics that are indicative of discontinuities (not shown). In this embodiment, the optical detector 340 and the light source 341 are positioned on one or more vertical faces 345 of the mobile platform 100. The vertical face 345 may be the front or the back of the mobile platform 100. It should be appreciated that any of the other sensors and detectors discussed may also be mounted on one or more vertical faces 345 or faces other than vertical (not shown). That is, the present disclosure is not limited to only downwardly directed sensing devices. Additionally, while described as configured for detecting discontinuities, the above-described sensor arrangements may be used to locate, identify, and characterize other features such as pumps, equipment, pillars, etc., for general steering, obstacle avoidance, or other purposes.

It should be noted that the discontinuity 320 may be detected by measuring any number of material or structural features; e.g., changes in wall thickness, material composition, roughness, density, color, etc. Numerous types of passive and active sensing devices may be used to detect discontinuities. Illustrative, but not exhaustive, sensing devices include: devices using reflections of electromagnetic waves such as LIDAR or other related laser-based sensor, a camera or other image sensor, a radar sensor; devices that use reflections of mechanical waves such as an ultrasonic sensor and a sonic sensor; devices that detect a change in orientation relative to the gravity vector such as inertial measurement unit (IMU), accelerometers, gyroscopes, and inclinometer; devices that detect variances in speed, voltage, current, and/or power usage within the propulsion system 400 (FIG. 2) caused by traversing a discontinuity 320; tactile devices configured to "feel" the discontinuity; and devices that detect changes in the transmission of magnetic fields such as a magnetic flux leakage sensor and an eddy current sensor.

Thus, it should be appreciated that the marker detector 306 may be an orientation sensor such as the inclinometer 328, a signal emitter 330 that emits an energy wave 332, a tactile detector 335 that contacts a surface 322, and/or an optical detector 340 that optically scans a surface 322. However, the marker detector 306 may be any device that is configured to detect the presence of an active and/or passive marker.

Figure 6A:
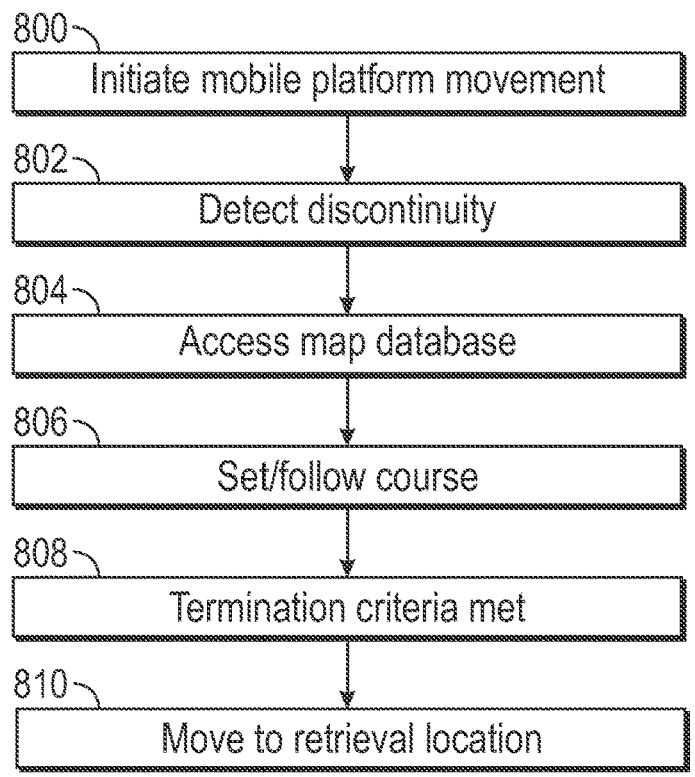
FIG. 6A is a flow chart depicting an illustrative method for controlling the mobile platform according to one embodiment of the present disclosure.
Figure 6B:
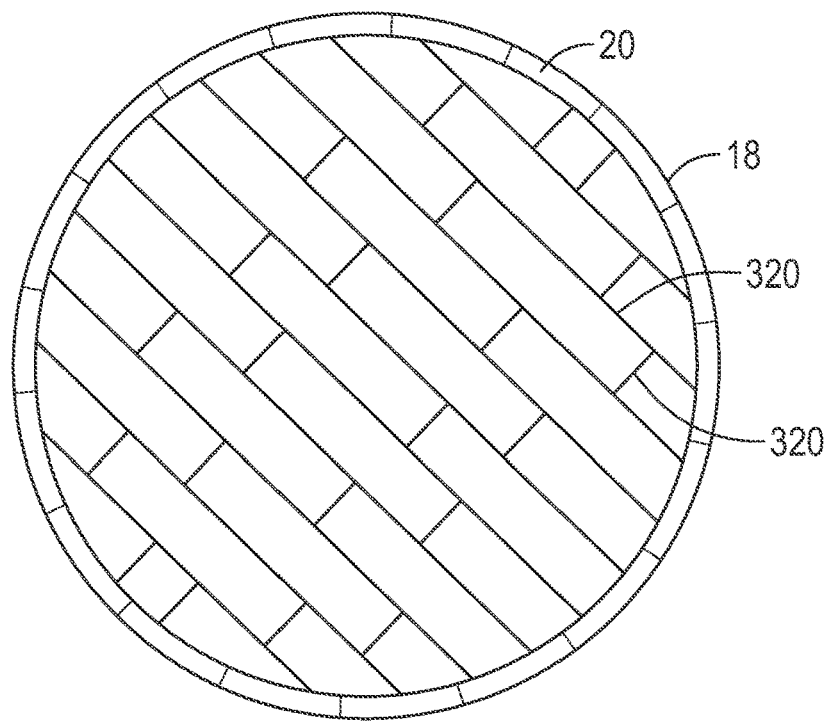
FIG. 6B illustrates a bottom wall of a tank having discontinuities detected by a mobile platform in accordance with one embodiment of the present disclosure.

FIGS. 6A, B illustrate a method by which the control unit 300 may intelligently traverse an interior of a tank 10 using the navigation module 304 that detects discontinuities 320, which are shown in FIG. 6B. FIG. 6B is a top view of a tank bottom wall 18 that includes discontinuities 320 in the form of weld structures. Some discontinuities 320 follow a grid-like pattern, such as weld lines formed by intersecting perpendicular lines. Other discontinuities 320 do not conform to a particular order or geometric pattern, such as the weld lines next to the wall 20.

Referring now to FIGS. 1, 2, 4 and 6A, the control unit 300 may include one or more navigation algorithms that use the discontinuities 320 to steer the mobile unit 100 in accordance with the FIG. 6A method. Step 800 begins after the mobile platform 100 has been positioned in the tank 10. The control unit 300 may initiate operations by executing a navigation algorithm that issues control signals 308 to the propulsion system 400. The propulsion system 400 may transmit information 313 to the control unit 300 that relates to system operations (e.g., confirmation of commands, system status, operating set points, etc.). The navigation algorithm may move the mobile platform 100 randomly or according to a preset initial course.

At step 802, the marker detector 306 passively or actively scans the interior of the tank 10 for discontinuities 320. If the marker detector 306 is a component of the task module 600, the control unit 312 may transmit control signals 312 to the control the task module 600 and the task module 600 may transmit information 311 representative of the detected discontinuities 320. The discontinuities 320 may be structural or augmented and be present in any of the walls of the tank 10 or other structures of the tank, such as the pillars 26 or equipment (e.g., sump). As signals are received, the control unit 300 may analyze these signals to determine if a discontinuity for steering the mobile platform 100 has been detected. At step 804, if such a discontinuity has been found, the control unit 300 accesses a map, which is a digital database (e.g., database 303a (FIG. 4)). In some arrangements, data in the map database is referenced to estimate a position or orientation of the mobile platform 100. In other arrangements, the control unit 300 creates the map or updates the map, if pre-existing, to record the position or relative position of the detected discontinuity and/or the position/relative position of the mobile platform 100. In this instance, the relative position may include an element of the position such as a distance traveled from another feature, a heading taken from another feature, and/or an orientation relative to another feature.

At step 806, the control unit 300 may set a course based on one or more detected markers, which may be passive markers such as discontinuities. The course may be in parallel with, perpendicular to, or another heading relative to the detected discontinuity or a feature identified by the detected discontinuities, such as a corner. While following the set course, the mobile platform 100 may perform one or more of the assigned tasks using the task module 600, such as scanning the tank bottom wall 18 for corrosion or other forms of damage. Also, one or more databases (e.g., 303b (FIG. 4)) may be continually updated with the positions, relative positions, and/or orientations of the detected discontinuities. The control unit 300 may repeat steps 802 to 806 as desired. Optionally, the control unit 300 may utilize information in the map, e.g., the location of previously detected discontinuities, along with the information relating to the currently detected discontinuity to determine a heading. A similar methodology may be used when detecting one or more active markers.

At step 808, the control unit 300 may determine that one or more preset termination criteria have been met. The termination criteria may be based on completion of the assigned task(s). Termination criteria may also be based on a time duration (e.g., a maximum of thirty-six hours in the tank 10), battery life (e.g., battery drained to ten percent of capacity), system health, operating condition, or another preset parameter. Upon determining that the termination criteria have been satisfied, the control unit 300 may initiate a power down of the mobile platform 100. Optionally, at step 810, the control unit 300 may instruct the mobile platform 100 to move to a predetermined retrieval location.

It should be appreciated the FIG. 6A method allows the mobile platform 100 to traverse the interior of the tank 10 without any "real time" or "near real time" human input. That is, human interaction with the mobile platform 100 may end after the mobile platform 100 is released inside the tank 10. Thus, the mobile platform 100 may be considered intelligent in that information relating to the environment is autonomously collected and processed in order to methodically traverse the interior of the tank 10. It should be understood that the described steps do not necessarily have to occur in the order described. For example, step 802 may occur before, simultaneously with, or after step 800. It is also emphasized that the FIG. 6A method is only one of numerous control schemes that may be used to imbue the mobile platform 100 with intelligent control. Other control schemes are discussed in detail later.

Figure 7:
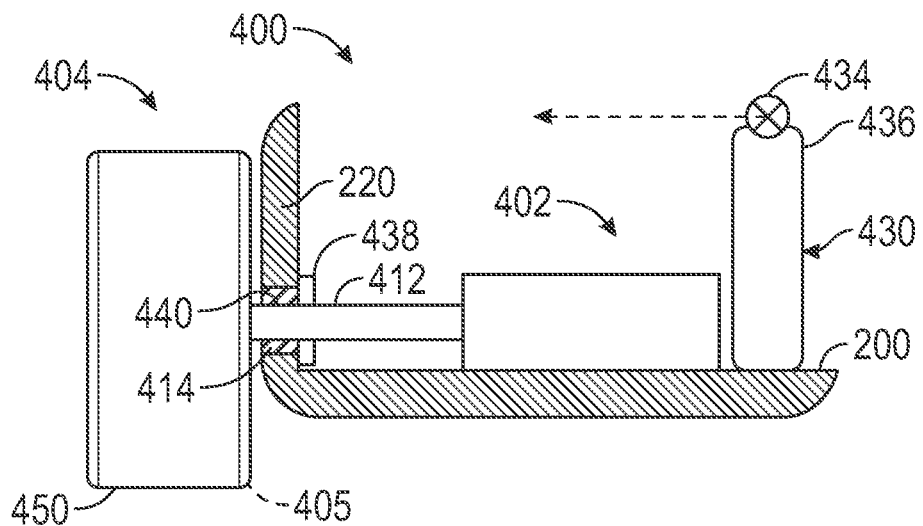
FIG. 7 schematically illustrates a propulsion system according to one embodiment of the present disclosure that uses a pressurized interior.

Referring to FIG. 7, there is shown one non-limiting embodiment of a propulsion system 400 according to the present disclosure. The propulsion system 400 may be configured to provide the mobile platform 100 with multiple degrees of freedom of movement. That is, the mobile platform 100 can change positions in the tank 10 (FIG. 1) by at least two or more of types of movement. These movements include linear movements such as surge (forward/backward), heave (up/down), and sway (left/right) and rotation movements about an axis such as pitch (lateral axis), yaw (normal axis), and roll (longitudinal axis). The propulsion system 400 may include an electrically powered internal rotary power device 402 and an external drive assembly 404. The rotary power device 402 may include a suitable motor. A drive shaft 412 extends through the enclosure wall 220 via an opening 440 and physically connects the internal rotary power device 402 to the external drive assembly 404. A seal 414 disposed in the enclosure wall 220 surrounds the drive shaft 412. The seal 414 may independently provide adequate sealing protection against tank fluids leaking into the enclosure interior 208 (FIG. 3). In some embodiments, a pressurizer 430 may release a pressurized gas that maintains or increases the pressure of the fluid in the enclosure 200 (FIG. 3) to be the same as or greater than the pressure of the fluid outside the enclosure 200 (FIG. 3); i.e., a neutral to a positive pressure differential. It should be understood that other types of propulsion systems may also be used.

Mobile platforms 100 of the present disclosure are not limited to any particular type or number of external drive assemblies. A mobile platform 100 may utilize a single external drive 404 assembly or two or more external drive assemblies 404. Also, the external drive assembly 404 may include gearing 405 for driving one or more impetus members such as wheels 450 as shown in FIG. 7B or tracks 442 as shown in FIG. 5A. Other arrangements may use propellers or impellers for impetus members. Thus, any structure that is capable of using the rotary power to provide the impetus for moving mobile platform 100 may be used. Herein, any structure or body configured for such use may be referred to as an impetus member. In some embodiments, the impetus member(s) may include magnetic elements or other device that enable the mobile platform 100 to climb vertical walls or hang from ceilings.

Mobile platforms 100 of the present disclosure are also not limited to the internal drive and external drive assembly configurations described above. FIG. 7 depicts an impetus member having a dedicated internal rotary power device 402. However, in variants, a propulsion system 400 may include one internal rotary power device 402 that drives two or more external drive assemblies 404. Thus, arrangements for the propulsion system 400 may or may not have a one-to-one correspondence between the internal rotary power devices 402, and the external drive assemblies 404.

Figure 8:
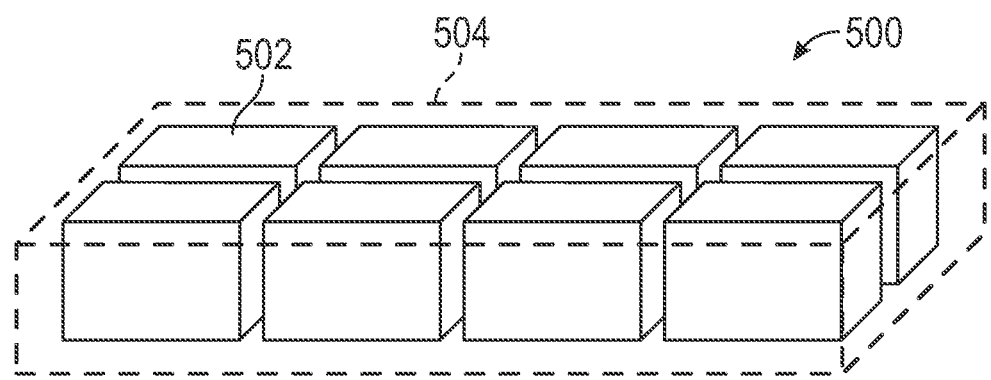
FIG. 8 isometrically illustrates a power supply according to one embodiment of the present disclosure.

Referring to FIG. 8, power for the subsystems of the mobile platform 100 may be supplied by the power supply 500. The power supply 500 may include a battery bank 502 housed within a suitable casing 504. In some embodiments, one power supply 500 energizes all of the subsystems. In other embodiments, two or more separate power supplies 500 may be used. Additionally, electronic and computerimplemented controls for power discharge may be performed by suitable processing circuitry (not shown). Generally, the power supply 500 supplies power at a level to fully energize all subsystems of the mobile platform 100 because the mobile platform 100 does not have an active line supplying power during operations. By "fully" energized, it is meant that that a subsystem is supplied with sufficient energy to execute all intended functions.

Figure 9A:
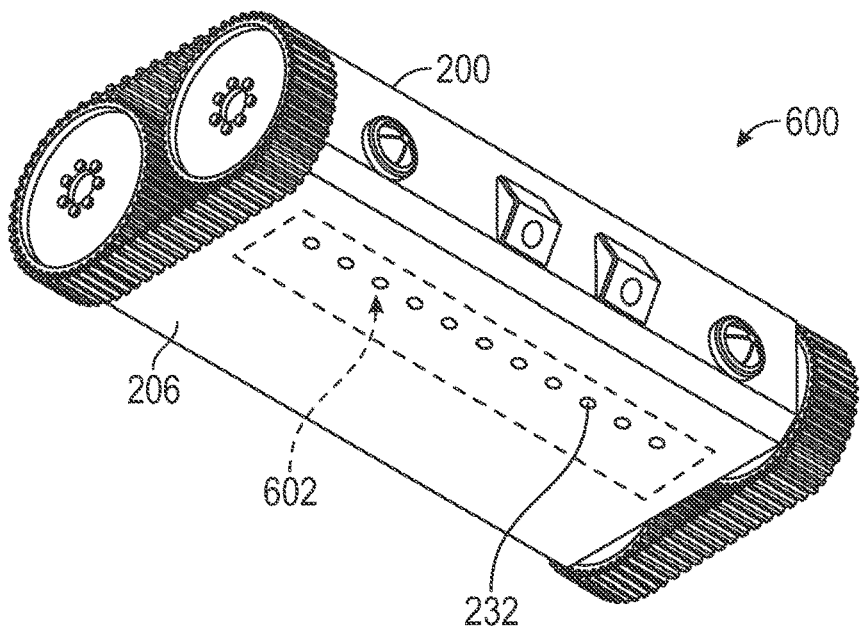
FIGS. 9A-B schematically illustrate a task module adapted with sensors in accordance with one embodiment of the present disclosure.

Referring to FIGS. 9A,B, there is shown one embodiment of a task module 600 that may be carried by the mobile platform 100 to perform inspections of a tank wall 16, 18, 20 (FIG. 1). The task module 600 may include one or more instruments that collect information from which the thicknesses of sections or segments of the walls making up the tank may be determined. In one embodiment, the task module 600 includes a transducer array 602 configured to direct acoustic signals through windows 232 out from the bottom 206 of the enclosure 200. The windows 232 may be sealed with a material (not shown) such as a polymer that is conductive to acoustic energy. Thus, the windows 232 do not impair the liquid-tight nature of the enclosure 200. In one arrangement, the transducer array 602 may include a plurality of sensors that emit signals into the tank wall 16, 18, 20 (FIG. 1) and detect the reflections of these signals. Illustrative sensors include, but are not limited to, sonic sensors, ultrasonic sensors, magnetic field and flux detectors. The detected signals may be digitized using appropriate circuitry and transmitted to the control unit 300 (FIG. 2) via a communication link 604. The control unit 300 (FIG. 2) can store the information in a suitable memory module for later retrieval. It should be noted that the transducer array 602 may also be used to identify discontinuities for navigation/guidance purposes. The task module 600 may be supported by a suitable base 230 (FIG. 3B, C) fixed in the enclosure 200 (FIG. 3B,C).

It should be understood that the task module 600 may also incorporate other devices for estimating the condition or state of one or more features of the tank 10. The features may be one or more structures making up the tank 10 or an ambient condition in the tank 10. Referring to FIGS. 2 and 5A-E, by way of non-limiting examples, the task module 600 may include an orientation sensor such as the inclinometer 328, a signal emitter 330 that emits an energy wave 332, a tactile detector 335 that contacts a surface 322, and/or an optical detector 340 that optically scans a surface 322. These instruments may provide information relating to the condition of the walls or of other structures of the tank 10 such as corrosion, damage, structural integrity, etc. The task module 600 may also incorporate devices for the retrieval of materials from the inside of the tank 10 or for the delivery of materials to the inside of the tank 10.

The mobile platform may optionally include other mechanisms to enable additional functions. Other examples of such devices are described in connection with FIGS. 10 and 11A-D below.

Figure 10:
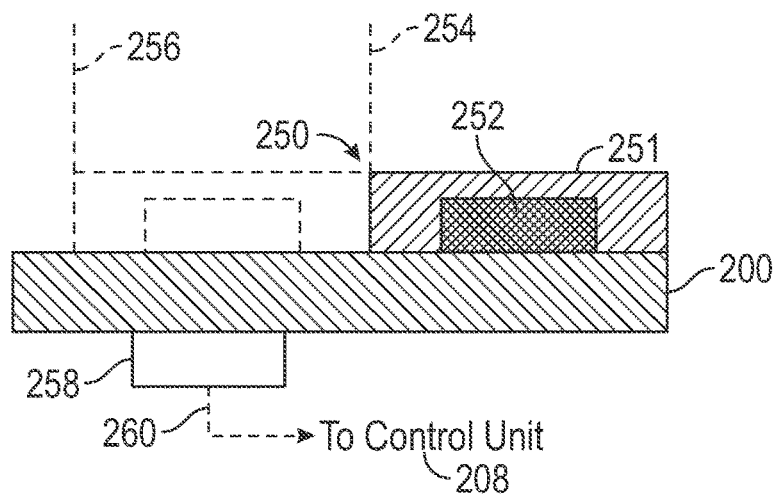
FIG. 10 schematically illustrates a switch assembly in accordance with one embodiment of the present disclosure.

Referring to FIG. 10, there is shown a switch assembly 250 for communicating with the mobile platform 100 (FIG. 2). For example, the switch assembly 250 may be used to shift between power states, activate or de-activate subsystems, initiate pre-programmed instructions, etc. The switch assembly 250 is a non-momentary type that does not require a passage to the interior 208 of the enclosure 200. A "momentary switch" only engages while actuated. A "non-momentary switch" latches and remains in a set position. In one non-limiting embodiment, the switch assembly 250 may have a lever member 251 positioned on or near an outer surface of the enclosure 200. The lever member 251 may have an external magnetic element 252, or a magnetic material such as iron, and that is movable between two positions, e.g., an "off" position 254 and an "on" position 256 (shown in hidden lines). The movement may be a rotation and/or a translation. Sealed inside the enclosure 200 is a sensor 258 that can detect a magnetic field such as a Hall effect type sensor or a reed switch. Shifting the switch assembly 250 from the "off" position 254 to the "on" position 256 causes the sensor 258 to transmit a signal 260 to the control unit 300 (FIG. 2)). Other non-momentary switches may utilize pressure activation or a command signal (e.g., acoustic wave).

Referring to FIGS. 1, 2, and 10, in one non-limiting method of operation, the switch assembly 250 is moved to the "on" position while the mobile platform 100 is outside of the tank 10 (FIG. 1). The signal 260 received by the control unit 300 from the switch assembly 250 commands the control unit 300 to shift from a no-power, low-power or sleep mode to a higher power consuming mode, such as a "start of operation" mode. The "start of operation" mode may begin with a system check, the successful conclusion of which may be indicated by an audio, visual, mechanical (e.g., shock, vibration, impact, pressure, physical movement, etc.), or electromagnetic (EM) signal. Next, the control unit 300 may start a preset duration for a quiet mode of, say thirty minutes. In the quiet mode, the control unit 300 remains functionally dormant while the mobile platform 100 is being positioned in the tank 10. At the end of the quiet mode, the control unit 300 may enter a period where quiescence is monitored. For example, an on-board motion sensor, such as an accelerometer, may be used to detect whether or not the mobile platform 100 is moving. If the mobile platform 100 has been determined to be motionless for a preset duration, e.g., thirty minutes, then the control unit 300 may commence operation, which may be the highest power consuming mode. It is emphasized that the described switch assembly and method for commencing operations is only one of various devices and methods that may be used to bring the mobile platform 100 (FIG. 2) to operational readiness.

Figure 11A:
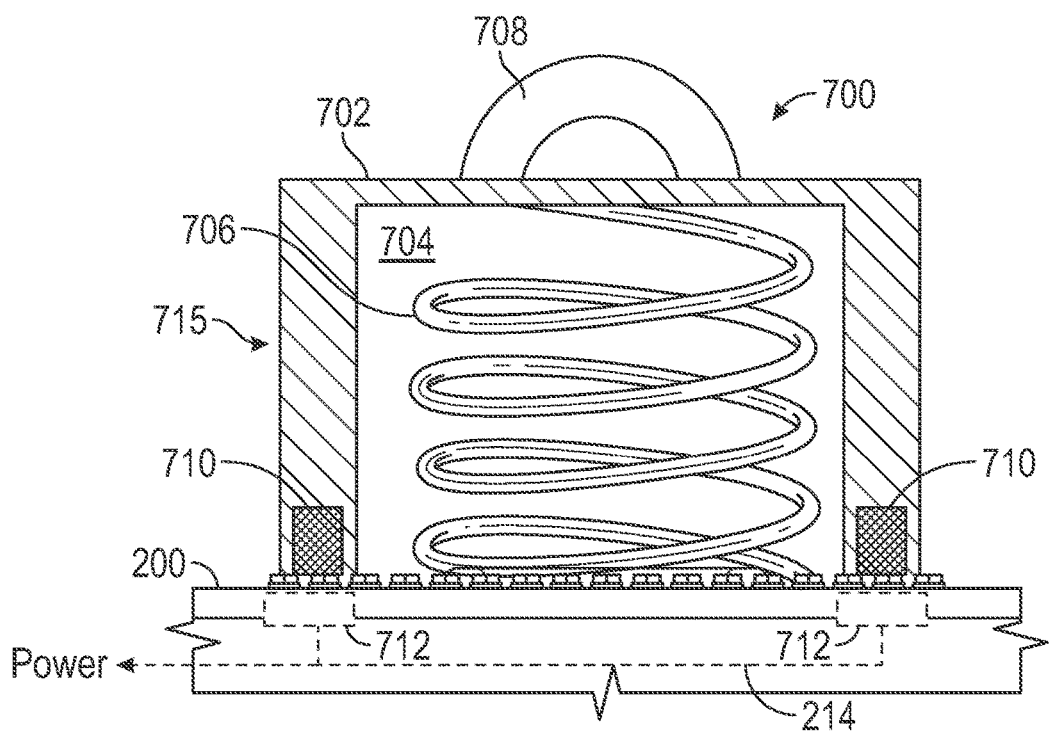
FIGS. 11A-B schematically illustrate retrieval modules in accordance with embodiments of the present disclosure.

Referring now to FIG. 11A, there is shown one non-limiting embodiment of a retrieval module 700 that may be used to retrieve the mobile platform 100 from the tank 10 at the conclusion of operations. As noted previously, the mobile platform 100 may be fully submerged, perhaps by several feet, within a liquid contained in the tank 10 (FIG. 1). The retrieval module 700 may release a buoy that can float at or below the liquid surface to facilitate location and retrieval. In one embodiment, the retrieval module 700 includes a buoyant body 702 having an inner compartment 704 in which a tether 706 is stored. The body 702, while shown as cylindrical, can be of any shape or size. The body 702 may be formed of one or more materials that enable the body 702 to be buoyant in the surrounding liquid. Optionally, the body 702 may be inflatable with a gas. For example, the body 702 may be formed as an expandable bag or bladder that can increase in volume using pressurized gas. A handle 708 or other suitable projection such as an eyelet may be fixed to an outer surface of the body 702. The body 702 may also include one or more magnetic elements 710 disposed on a lower portion and in close proximity to the outer surface of the enclosure 200. In embodiments, a magnetic steel may also be suitable. Sealed inside the enclosure 200 may be one or more electro-magnets 712. The electro-magnets 712 may be electrically connected to the control unit 300 (FIG. 2) and the power supply 500 (FIG. 2) via one or more lines 214. The magnetic elements 710, the electromagnets 712, and the control unit 300 form a latch assembly 715 that uses a magnetic force for selectively releasing the buoyant body 702.

During operation, the latch assembly 715 is in a locked position wherein the electro-magnets 712 are kept energized so that a magnetic connection is maintained with the magnetic elements 710. Thus, the buoyant body 702 is fixed to the enclosure 200. At the appropriate time, the control unit 300 shifts the latch assembly 715 to the released position wherein electro-magnets 712 are de-energized by terminating electrical power, which eliminates the magnetic connection. The buoyant body 702 then floats to or near the surface of the liquid in the tank 10 (FIG. 1). The tether 706 connects the body 702 to the mobile platform 100. Thus, the mobile platform 100 may be retrieved by pulling on the tether 706 or using the tether 706 as a guide to physically locate the submerged mobile platform 100. When the tether 706 is used as a retrieval carrier, then the tether 706 may use materials and construction that provide suitable loading capacity to support the mobile platform 100.

Figure 11B:
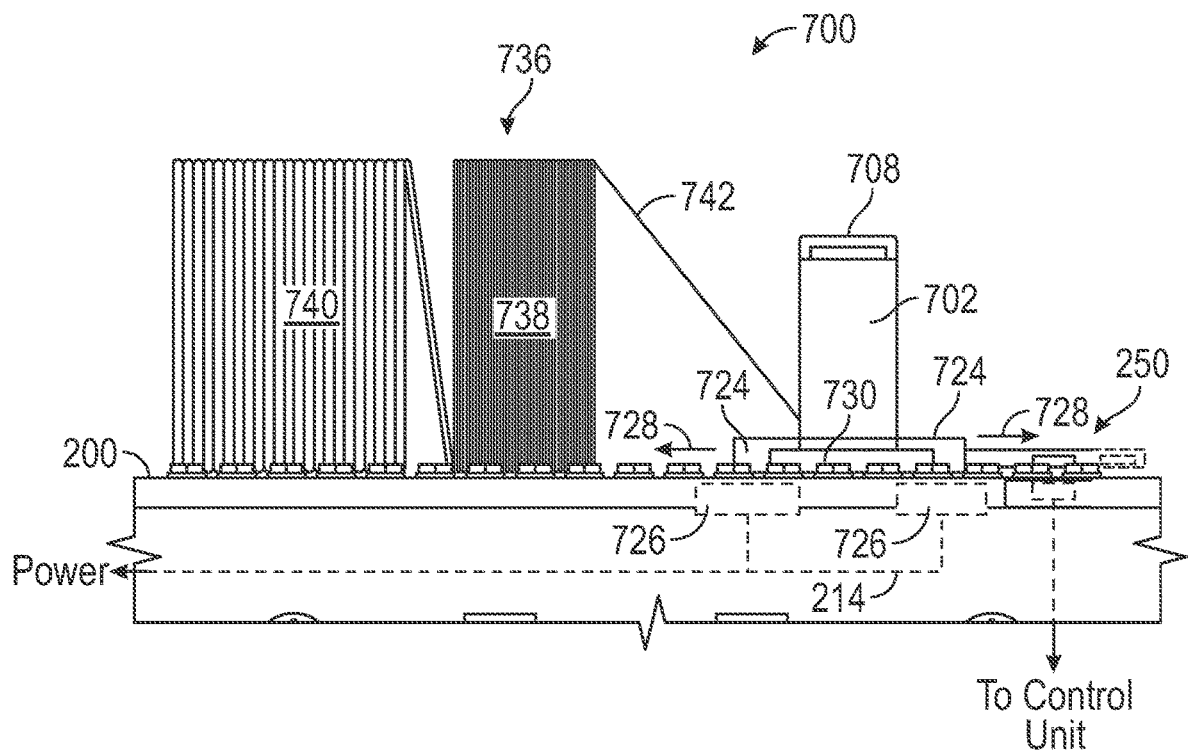

Referring now to FIG. 11B, there is shown in schematic form another non-limiting embodiment of a retrieval module 700 that may be used to retrieve the mobile platform 100 from the tank 10 at the conclusion of operations. In this embodiment, the retrieval module 700 includes a buoyant body 702, a handle or other similar manipulation member 708, and one or more electro-magnetically actuated latches 724. The latches 724 may positively engage a lip 730 of the buoyant body 702 and thereby fix the body 702 against the enclosure 200. The latches 724 may be shifted between a locked and unlocked position using electromagnetic type actuators 726. In the illustrated embodiment, the latches 724 slide away from the lip 730 in the direction shown by arrows 728 when the electromagnetic actuators 726 are energized. Other modes of movement or shifting may be used; e.g., rotational, pivoting, etc. Optionally, a switch assembly 250 may be fixed to one of the latches 724. The switch assembly 250 may be similar to that shown in FIG. 10. In one arrangement, when the latches 724 are in the closed position as shown, the switch assembly 250 is in "on" position. When the latches 724 are slid to the open position to release the buoyant body 702, the switch assembly 250 shifts to the "off" position, shown in hidden lines. It should be noted that a latch assembly having one or more latches and electromagnetic actuators may also be used in the FIG. 11A embodiment.

The retrieval module 700 of FIG. 11B uses a two-stage external tether 736 that includes a relatively light first stage tether 738 and a relatively stronger second stage tether 740. The first stage tether 738 may be connected by a flexible member 742, such as a wire, to the body 702. The material of the first stage tether 738 is selected to be light enough as to not impair the buoyancy of the body 702 but be strong enough to support the weight of the second stage tether 740 as the second stage tether 740 is unwound and retrieved. The material of the second stage tether 740 is selected to be strong enough to support the weight of the mobile platform 100 during retrieval. The second stage tether 740 may also be referred to as a retrieval carrier. Thus, each tether 738, 740 may have different loading capacities (e.g., tension loading). As a consequence, whereas a polymer cable may be suitable the first stage tether 738, a metal cable may be more appropriate for the second stage tether 740. However, any material-type may be used for either stage tether 738, 740 as long as their respective loading requirements are satisfied.

The FIG. 11B also integrates the shutdown of the mobile platform 100 into the operation of the retrieval module 700. Sealed inside the enclosure 200 may be one or more electromagnets 726. The electro-magnets 726 may be electrically connected to the control unit 300 and the power supply 500 via one or more lines 214. While the mobile platform 100 is operating, the electro-magnets 726 maintain the latches 724 in the locked position. Thus, the buoyant body 720 is fixed to the enclosure 200. At the appropriate time, electromagnets 726 may be de-energized by terminating electrical power, which eliminates the magnetic connection. The buoyant body 702 then floats toward the surface of the liquid in the tank 10 (FIG. 1). At the same time, the latches 724 move to the unlocked position, the switch assembly 250 shifts to the "off" position, which shuts down the mobile platform 100. Thereafter, the mobile platform 100 may be retrieved by first pulling on the first stage tether 738 to retrieve the second stage tether 740 and then pulling up the submerged mobile platform 100 using the second stage tether 740. It should be noted that a switch assembly 250 may also be integrated with the retrieval module of the FIG. 11A embodiment.

Figure 11C:
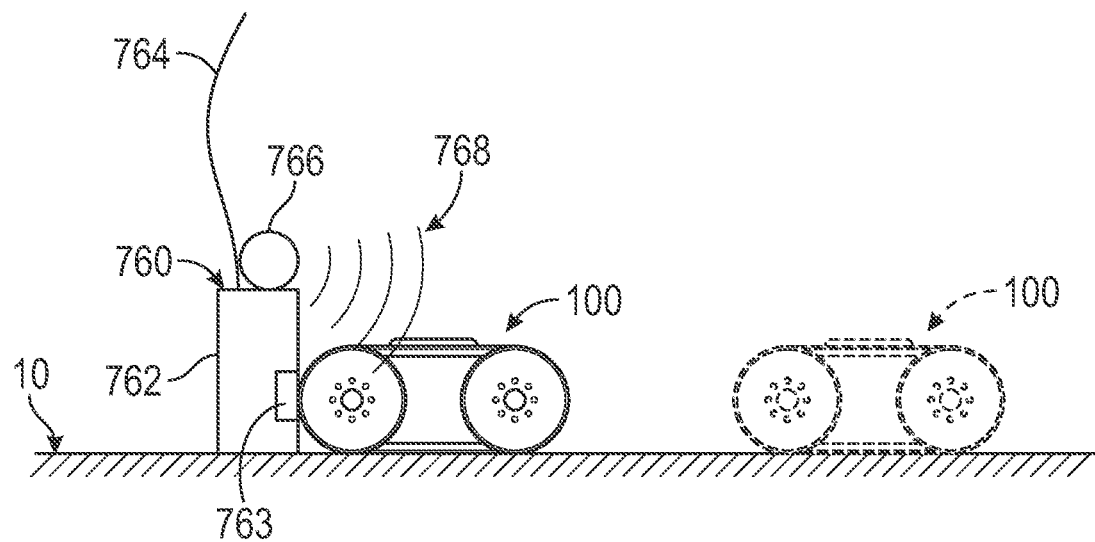
FIGS. 11C-D schematically illustrate devices that may be used to facilitate deployment and/or retrieval of a mobile platform in accordance with embodiments of the present disclosure.
Figure 11D:
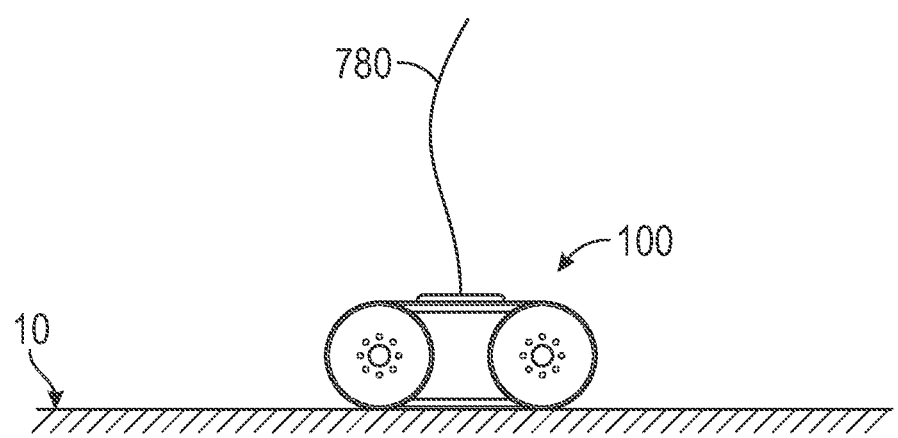

Referring now to FIGS. 11C-D, there are shown devices that may be used to facilitate deployment and/or retrieval of a mobile platform 100. FIG. 11C schematically illustrates a deployment assembly 760 that includes a dock 762 connected to a carrier 764. The mobile platform 100 may connect to the dock 762 using a mechanical and/or magnetic coupling 763. Optionally, the deployment assembly 760 may include a signal emitting beacon 766 that emits a wave 768, such as an electro-magnetic or acoustical wave. The carrier 764 may be a passive physical line, such as a cable, wire or rope. By "passive," it is meant that the carrier 764 does not convey signals, pressurized fluids, or power. The carrier 764 has sufficient tensile strength to convey the deployment assembly 760 and mobile platform 100 into the tank 10. In one mode of use, the deployment assembly 760 and mobile platform 100 may be lowered into a tank 10 together. Thereafter, the mobile platform 100 decouples from the dock 762 and moves freely, as shown in hidden lines. The deployment assembly 760 may be extracted from or remain in the tank 10 during operations. If the deployment assembly 760 remains in the tank 10 during operations, the carrier 764 may provide a physical, passive connection between the dock 762 and an object (not shown) inside or outside of the tank 10. Upon completion of operations, the mobile platform 100 may return and re-connect to the dock 762 for retrieval or be retrieved in another manner. In some embodiments, the carrier 764 may be used without the dock 762 to deploy and/or retrieve the mobile platform 100. That is, the carrier 764 may be configured to function as a deployment carrier and/or a retrieval carrier.

If present, the beacon 766 may emit a signal that the mobile platform 100 may use for navigation or other purposes. It should be understood that the beacon 766 is merely representative of any number of devices that may be carried by the dock 762. For instance, a control unit (not shown) may be carried by the dock 762 and communicate with the mobile platform 100.

FIG. 11D schematically illustrates a passive carrier 780 that remains connected to the mobile platform 100 during operations in the tank 10. The passive carrier 780 may be a rope, wire, cable, or other tension-bearing member that may be used to move or simply locate the mobile platform 100. As noted above, a passive carrier does not communicate any power, signals, or materials (e.g., pressurized gas) to or from the mobile platform 100. Rather, the carrier 780 may provide a physical, passive connection to an object inside or outside of the tank 10. Thus, the carrier 780 may act as a deployment and/or retrieval mechanism or a line that allows the mobile platform 100 to be located.

Figure 12A:
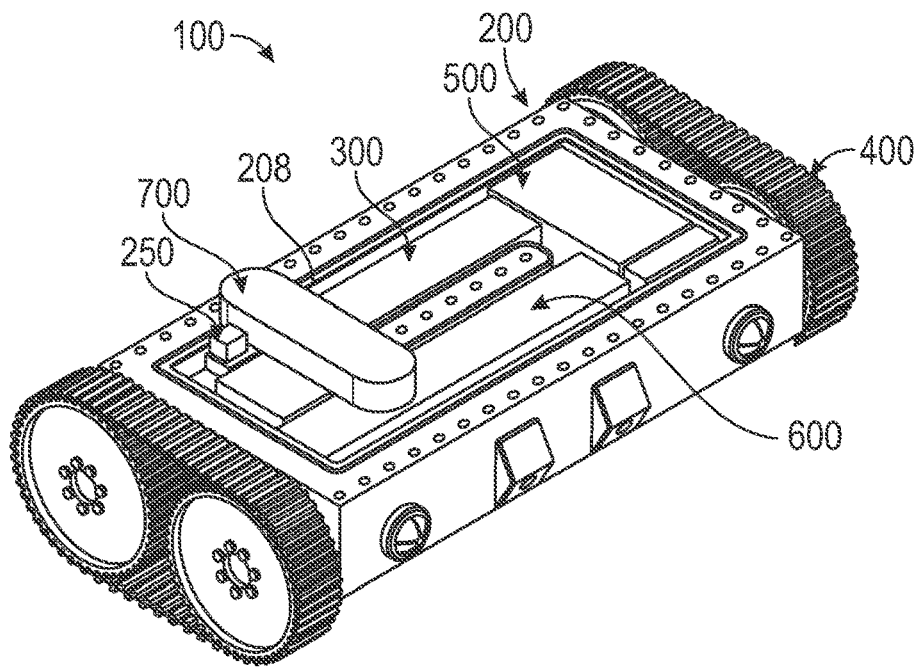
FIG. 12A-B isometrically illustrate another embodiment of a mobile platform in accordance with the present disclosure.
Figure 12B:
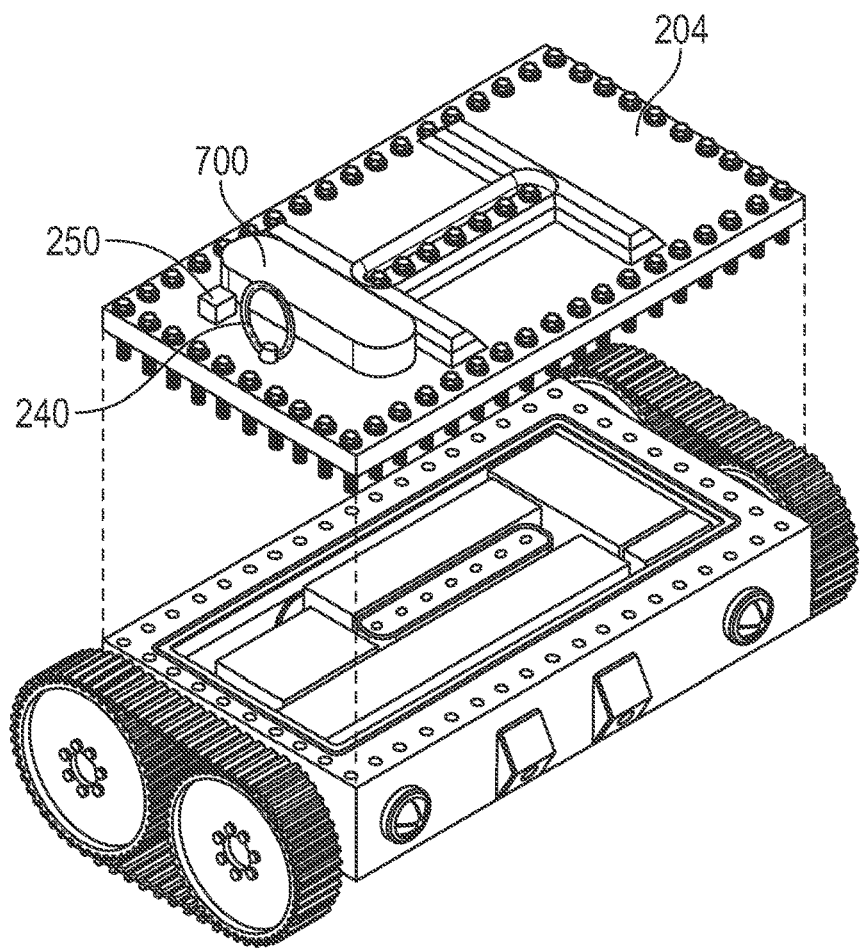

Referring now to FIGS. 12A-B, there is shown another embodiment of an intelligent mobile platform 100 according to the present disclosure. Similar to the embodiment of FIG. 2, the mobile platform 100 includes an enclosure 200, a control unit 300, a propulsion system 400, a power supply 500, and a task module 600. The lid 204 of the enclosure 200 is shown only in FIG. 12B to better illustrate the interior 208 in FIG. 12A. The details and variants of the enclosure 200, propulsion system 400, power supply 500, and the task module 600 have been described in detail above. The FIG. 12A embodiment includes a non-momentary switch 250 as described in connection with FIG. 10 and a retrieval module 700 as described in connection with FIG. 11A-B. An eyelet 240 may be fixed to the lid 204. The eyelet 240 may be any loop, hook, or other body to which a lifting/handling device can be releasably connected. The control unit 300 of the FIGS. 12A-B embodiment is discussed below.

Figure 13:
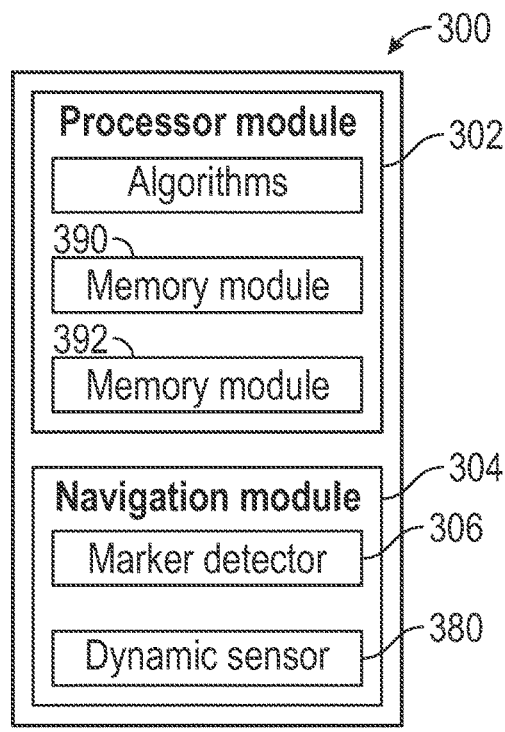
FIG. 13 is a functional block diagram of another control unit for a platform according to one embodiment of the present disclosure.

Referring to FIG. 13, the control unit 300 of the FIGS. 12A-B mobile platform includes a navigation module 304 having two or more distinct types of sensing instruments. The first sensing instrument is a marker detector 306 that detects discontinuities as described previously in connection with FIGS. 4-5E. The second sensing instrument may be a dynamic sensor 380 that estimates one or more navigation parameters. As used herein, a navigation parameter characterizes an absolute and/or a relative position of the mobile platform 100 in a desired coordinate system (e.g., x/y space, polar coordinate defined space) and/or orientation (e.g., direction faced, inclination, etc.). For example, the dynamic sensor 380 may estimate a parameter such as a distance traveled, a degree of rotation, acceleration, tilt, and/or relative changes in the direction of movement. While referred to in the singular, it should be understood that the dynamic sensor 380 may comprise a suite of two or more discrete and different sensors, each of which provide different information. Suitable dynamic sensors include, but are not limited to, odometers, RPM sensors, inclinometers, gyroscopes, and accelerometers. Still other dynamic sensors may sense operating parameters of motors, transmissions, and motor controllers (not shown). The information from a dynamic sensor 380 may be used to steer in a desired direction, reduce errant motion of the mobile platform 100 (FIGS. 12A-B), steer past obstacles, and/or identify locations of interest (e.g., a retrieval point).

Figure 14:
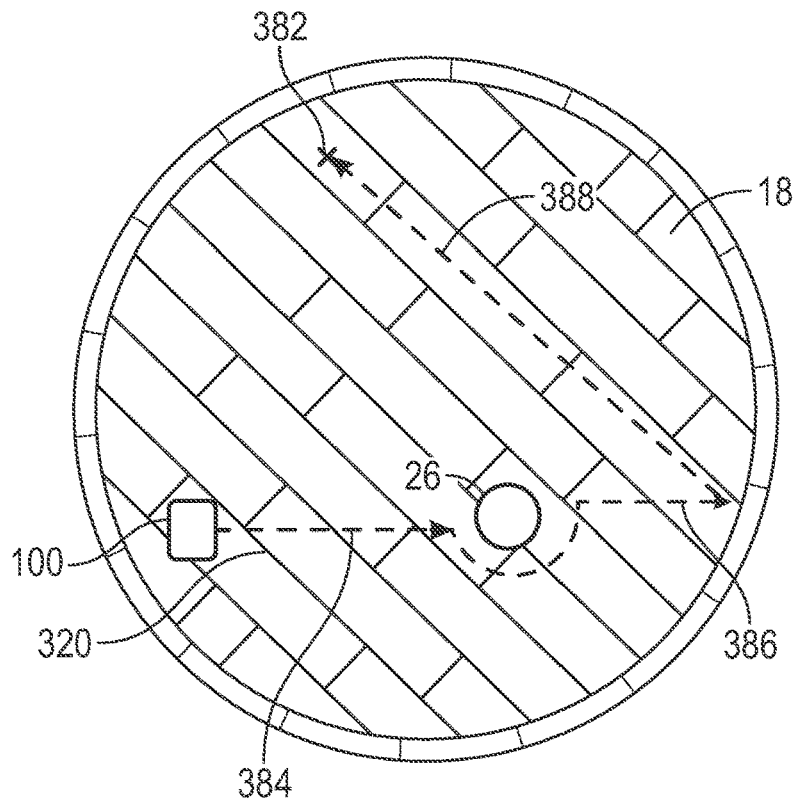
FIG. 14 illustrates a bottom wall of a tank along which the FIG. 13 embodiment steers a mobile platform in accordance with one embodiment of the present disclosure.

Some of the uses for the information provided by the dynamic sensor 380 may be illustrated with reference to FIG. 14, which shows a portion of a tank bottom wall 18 formed of steel plates, an obstacle such as a pillar 26, and a retrieval point 382. Referring to FIGS. 12A-B and 13, during operation, the mobile platform 100 may follow a path having a leg 384. The mobile platform 100 may have started on the leg 384 upon the marker detector 306 detecting a discontinuity 320. Thereafter, the dynamic sensor 380 may provide information that can be used to issue steering instructions to steer the mobile platform 100 along the leg 384. Thus, for instance, the dynamic sensor 380 can detect if the mobile unit 100 has drifted to the left or right from a desired heading and quantify the amount of variance from the desired heading. Corrective steering commands can be issued based on this information.

During operation, the mobile platform 100 may encounter a number of obstacles. One common obstacle is a pillar 26. Other obstacles include sumps, walls, bracing structures, debris, joints, etc. As noted previously, some are known whereas others have entered the tank 10 unintentionally. The mobile platform 100 may be programmed to handle such obstructions using a variety of techniques. For instance, upon encountering the obstacle 26, the steering algorithm may direct the mobile platform 100 to incrementally change direction to maneuver around the obstacle 26 until the mobile platform 100 has returned to a heading of the prior leg 384. Thereafter, the mobile platform 100 begins the next leg 386.

The return to the heading of the prior leg 384 is enabled by the information provided by the dynamic sensor 380. For instance, the dynamic sensor 380 can determine the degree of rotation and the distance traveled during the maneuvering. Additionally, when preset criteria are met, such as the conclusion of the task, the dynamic sensor 380 can provide information for steering the mobile platform 100 to the retrieval point 382. For instance, the dynamic sensor 380 can determine the degree of rotation required to head toward the retrieval point 382 and the distance traveled while heading to the retrieval point 382.

It should be understood that the mobile platform 100 does not necessarily carry all the above-described features and components within a single enclosure. Rather, in some embodiments, the above-described components may be dispersed into two or more separate enclosures that may be physically attached to one another. For instance, in some embodiments, an enclosure having only a power supply 500, a propulsion system 400, and task module 600 are in one mobile enclosure, and the remainder of the components, such as the control unit 300, are in a separate enclosure.

Figure 15:
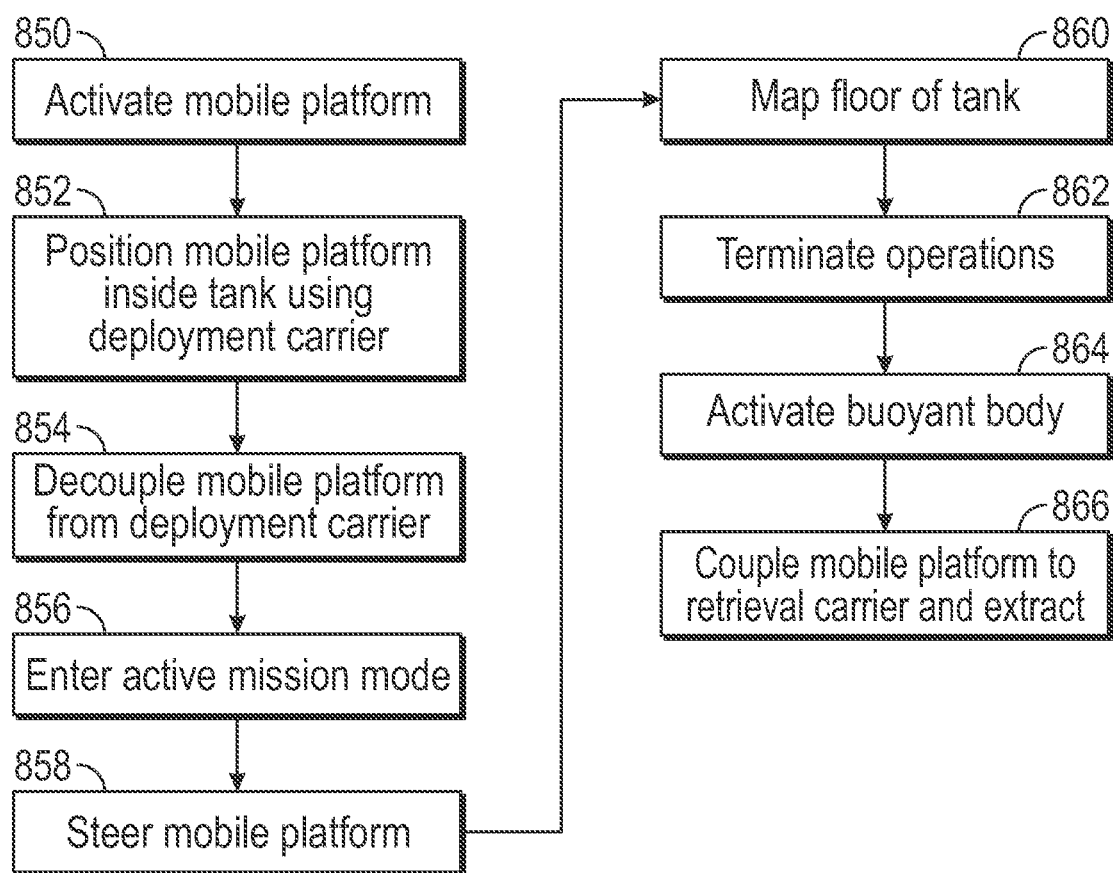
FIG. 15 is a flow chart depicting an illustrative method for using the mobile platform to perform a task according to one embodiment of the present disclosure.
Figure 16A:
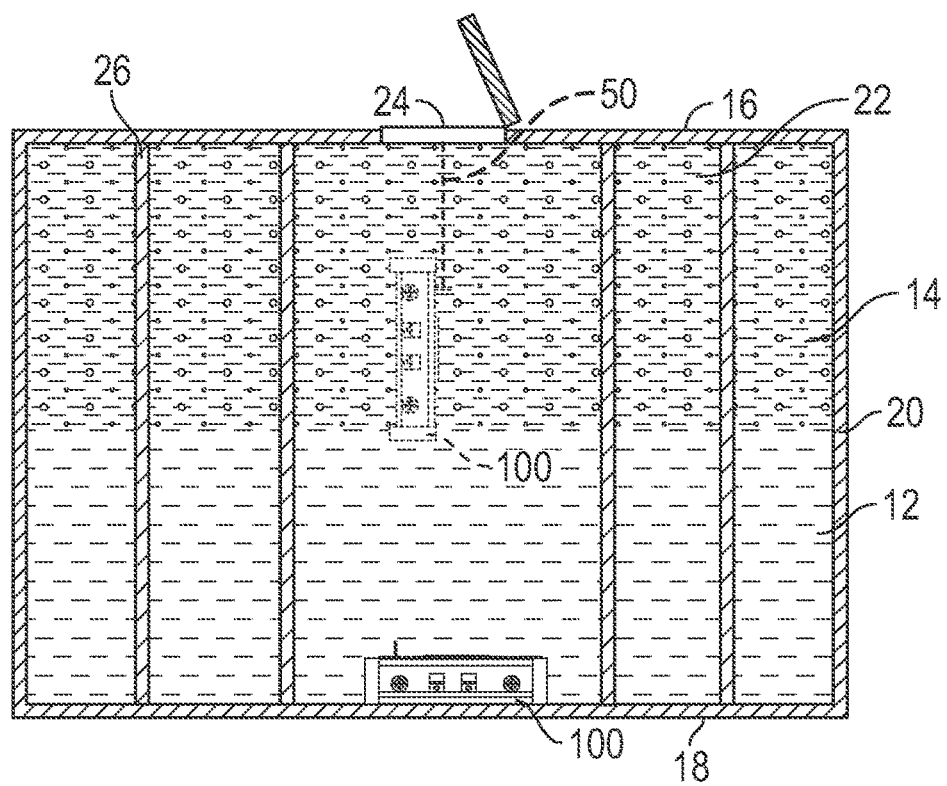
FIGS. 16A-B sectionally illustrate the deployment, release, and retrieval of a mobile platform during the performance of the FIG. 15 method according to embodiments of the present disclosure.
Figure 16B:
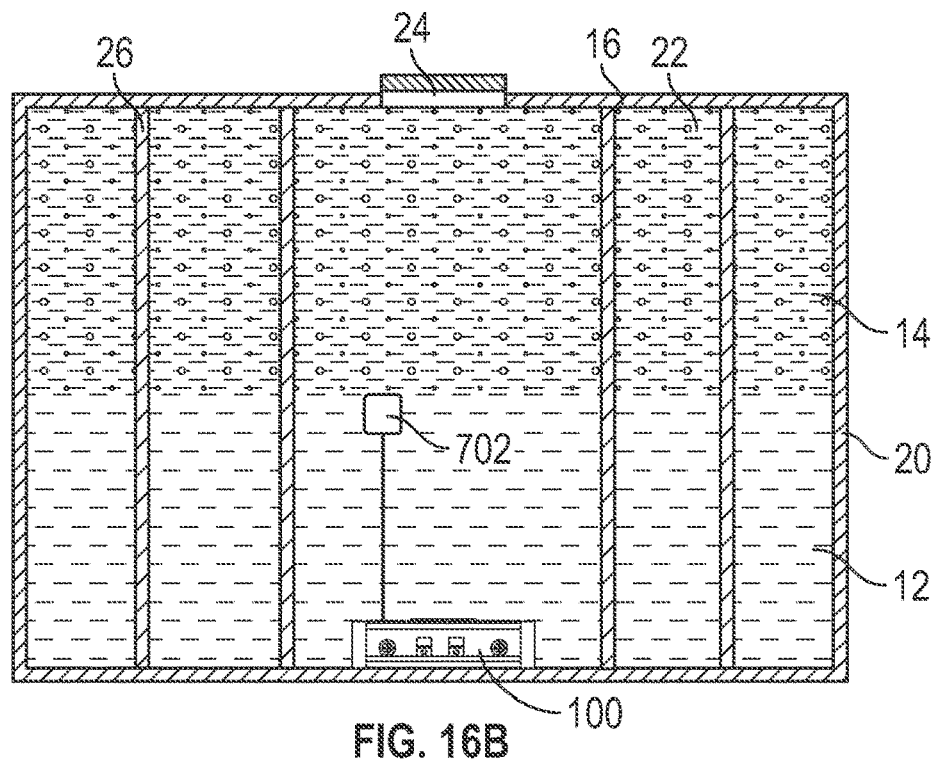

An illustrative mode of use of the mobile platform of FIGS. 12A-B will be discussed with reference to FIGS. 15 and 16A, B. FIG. 15 is a flow chart that identifies the several steps by which the mobile platform 100 is used to perform one or more functions in a tank 10. FIG. 16A schematically illustrates the mobile platform 100 during insertion into a tank 10 and during operation and FIG. 16B schematically illustrates the mobile platform 100 ready for retrieval after operation. While not always the case, the tank 10 is shown filled with liquid 12, such as a hydrocarbon, at a level that fully submerges the mobile platform 100. Above the liquid body 12 is a gaseous body 14, which may also be a hydrocarbon. Other substances, such as dirt and debris, may also be in the tank 10.

At step 850, the mobile platform 100 is activated while outside of the tank 10, such as by using the switch 250, to enter a pre-operation mode. At this time, the control unit 300 may initiate one or more diagnostic sweeps and provide an indication to a work crew that on-board systems are functional. Thereafter, the control unit 300 may enter a quiet mode while the work crew inserts the mobile platform 100 into the tank via the hatch 24 at step 852. The mobile platform 100, shown in hidden lines in FIG. 16A, may be lowered into the tank using a suitable deployment carrier 50 and bracing structure (not shown). The deployment carrier may be a non-rigid carrier such as tether, which may comprise a rope, cable, chain, etc. In other embodiments, the deployment carrier may be rigid, such as a pipe, pole, or tube. At step 854, after the mobile platform 100 rests on the tank bottom wall 18, the deployment carrier 50 is decoupled and retrieved and the hatch 24 may be closed.

At step 856, the mobile platform 100 may execute a "countdown" phase during which the mobile platform 100 monitors one or more inputs, such as time and/or movement, to determine whether to enter a full operational mode.

Upon deciding to enter full operational mode, the control unit 300 may energize the necessary subsystems and begin execution of the pre-assigned task(s). It should be noted that the mobile platform 100 has not required a communication link with operators, human or otherwise, that are outside of the tank 10. Therefore, all decisions to be made during operations may be done by the control unit 300 using pre-programmed instructions and by obtaining relevant information, i.e., intelligently. However, in some variants, human or machines positioned external to the tank may interact with the mobile platform 100. For example, striking the wall of the tank 10 may be used to impart an acoustic command signal to the mobile platform 100 (e.g., "turn on," "turn off," "return to retrieval location," "switch operating modes," "transmit a signal," etc.).

Steering the mobile platform 100, at step 858, may include locating one or more discontinuities using the marker detector 306, as described in reference to FIGS. 4-6A, and estimating one or more navigation parameters using dynamic sensors as described in connection with FIGS. 13-14. The control unit 300 processes this information to traverse the tank interior 22 using a predetermined methodology. It should be noted that the mobile platform 100 has no active physical connection after deployment as shown in FIG. 16A,B. Specifically, no energy (e.g., electricity), data signals, or materials such as pressurized gases are communicated to the mobile platform 100 via a wire, cord, cable, pole, tube, pipe, or any other rigid or non-rigid conveyance carrier from a location external to the tank 10. Thus, as used herein, an "active" line or carrier is one that communicates or transmits power, materials, or data signals while the mobile platform 100 is in the tank 10. As noted above, the mobile platform 100 may have a passive carrier as discussed in connection with FIGS. 11C-D. A "passive" line or carrier is one that does not communicate or transmit power, materials, or data signals while the mobile platform 100 is in the tank 10.

Figure 9B:
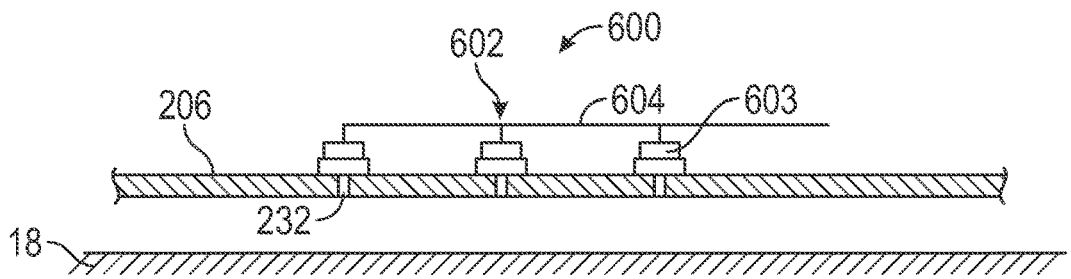

Step 860, which may be implemented for operations involving tank inspections, may be performed concurrently with step 858. Using the sensing device as described in connection with FIG. 13, the mobile platform 100 scans one or more walls of the tank 10 using an inspection module such as the task module 600 shown in FIG. 9A-B. The task module 600 and the control unit 300 can collect, organize, and process the information required to generate a database of the wall thicknesses for the scanned areas of the tank 10. The database may include the thicknesses of all sections of the tank bottom wall 18 or thicknesses of just the locations/sections that are "out of norm" (i.e., different from a specified value or range). The walls inspected typically include the tank bottom wall 18. It should be noted that for inspections, the sensing device used to inspect the walls of the tank 10, such as ultrasonic sensors, may also be used as a marker detector 306.

In one non-limiting method, the mobile platform 100 performs the scanning activity by first locating the edges, or sides, that define a perimeter of a plate. For instance, the mobile platform 100 may first locate a corner of the plate by tracing an edge until another edge is found, which identifies the corner. Tracing may be performed any number of ways including following a reversing path (e.g., zigzag) along a detected edge. Next, the mobile platform 100 may steer parallel to one of the edges of that corner to locate the opposite corner. Locating the other corner then establishes the position of two parallel edges and one perpendicular edge of the plate. The mobile platform 100 may move incrementally along the parallel edges to locate the remaining corners of the plate. Thereafter, the mobile platform 100 may initiate a wall thickness scan of that plate. Once complete, the process can be repeated for another plate. In another non-limiting method, the mobile platform 100 may first identify the edges of all the plates making up the tank bottom wall 18 of the tank 10. Afterwards, the mobile platform 100 can scan each of the plates. It should be noted that the multiple degrees of freedom along which the propulsion system 100 may move the mobile platform 100 enables efficient execution of the above task, as well as other tasks.

At step 862, the mobile platform 100 begins the termination of operations. The termination may be triggered using any number of conditions. These conditions may be related to quality and/or quantity of information obtained during inspections, completion of assigned tasks, remaining power levels, operational considerations such as possible malfunctions, etc. One illustrative termination sequence may include navigating to a predetermined retrieval location. This location may be below the hatch 24. Alternatively, if the mobile platform 100 has magnetic type external drive units, the mobile platform 100 may drive to a location proximate to the hatch 24. The magnetic type external drive units (not shown) will enable the mobile platform 100 hang effectively upside-down from the top wall 16. Still other sequences may include simply remaining in place and transmitting a signal that identifies the location of the mobile platform 100. The mobile platform 100 may be retrieved by hooking or otherwise connecting the mobile platform 100 to a suitable carrier, e.g., the deployment carrier 50. Thus, the deployment carrier 50 may be also be used to retrieve the mobile platform 100. The mobile platform 100 may also be retrieved by using a separate retrieval mobile platform (e.g., deployment assembly 760 of FIG. 11C) that can connect, to the mobile platform 100.

Step 864 may be used for a mobile platform that includes a retrieval module 700, such as that shown in FIGS. 11A-B. After moving to a retrieval location or staying in place, the mobile platform 100 releases the buoyant body 702. The buoyant body 702 floats to the surface of the liquid body or to a depth below the surface. Optionally, the buoyant body 702 may emit a signal, fluoresce, and/or be illuminated. Finally, the mobile platform 100 may power down all subsystems, except any device on the buoyant body 702 that emits a signal. At step 866, the work crew can extract the mobile platform 100 by connecting a retrieval carrier, such as a cable or pole, to the buoyant body 702 or other part of the mobile platform 100. Alternatively, the mobile platform 100 may be retrieved by using a released tether as discussed in connection with FIGS. 11A, B.

The total "power down" or shut down of the mobile platform 100 at step 864 may be initiated by the control unit 300. Alternatively, a retrieval module 700 as shown in FIG. 11B may be used to simultaneously release the retrieval body 702 and shut down the mobile platform 100. By "power down" or "shut down," it is meant that the mobile platform 100 is in a state where no power is communicated to any sub-system and that no sub-system is consuming power or that no sub-system is consuming power at a level that could potentially generate a spark.

In some embodiments, one or more elements or components of the mobile platform 100 may remain in the tank 10 after retrieval. For example, the mobile platform 100 may deposit an object that functions as an active or passive marker to identify a retrieval point. The object left behind may also be a spent task module, a remnant of a deployment or retrieval carrier, or other component that does not require retrieval.

Among the many advantages of the teachings of the present disclosure, at least the following should be noted. One is that human presence was not required either inside or outside the tank 10 in order to operate the mobile platform 100. Another advantage is that the mobile platform 100 performed the inspection while the tank 10 contained liquids. Thus, the tanks themselves can continue to be used as normal without service disruptions. Still another advantage is that the tank 10 is sealed by the hatch 24 during operation, which prevents the energetic substance 14 from escaping into the surrounding environment. Thus, a spark occurring external to the tank 10, e.g., near the hatch 24, cannot ignite the energetic substance 12, 14 inside the tank 10.

Referring to FIGS. 16A and B, it should be appreciated that embodiments of the present disclosure that use ultrasonic sensing devices will operate with better resolution because the mobile platform 100 is submerged such that a liquid body extends between the mobile platform 100 and one or more surfaces of the tank 10. The liquid body between the ultrasonic sensors and a wall of the tank provides a highly efficient wave transmitting medium through which acoustic energy can be transmitted. Notably, such a liquid body or layer is not present when inspections are performed by human personnel in air. Additionally, the ability of the mobile platform 100 to operate while fully submerged can also enable additional activities. For example, the mobile platform 100 may utilize acoustic receivers to detect sounds associated with leaking fluid. For acoustic detection, the mobile platform 100 may enter a semi-quiet mode wherein movement is halted and any subsystems that generate noise are shut down. In this semi-quiet mode, the acoustic receivers monitor the surrounding liquid body for acoustic signals caused by fluid leaking out of the tank 10.

It should be appreciated that embodiments of the present disclosure that use the previously-described combinations of size and weight restrictions may facilitate the handling and deployment of the mobile platform 100 while also reducing the risk of damage to the tank in which a task is performed.

While step 860 of the FIG. 15 method pertained to scanning walls of the tank 10 to determine thicknesses, it should be understood that the FIG. 15 method may also be used to execute tasks related and unrelated to inspections. For example, other inspection methods such as visual scans can be performed. For example, cameras may be used to collect visual images of the tank walls such as the sides 20 and/or bottom 18.

The above-described systems and related methods used discontinuities associated with the tank 10 (FIG. 1) as navigation markers, or simply 'markers,' to control movement. The welds and plate overlaps representing these discontinuities were formed while mating of steel panels and thus may be considered structural elements of the tank 10. Thus, the above-described embodiments may be considered to intelligently traverse an interior of a tank 10 using structural markers. However, other embodiments of the present disclosure may utilize other types of markers.

Figure 17:
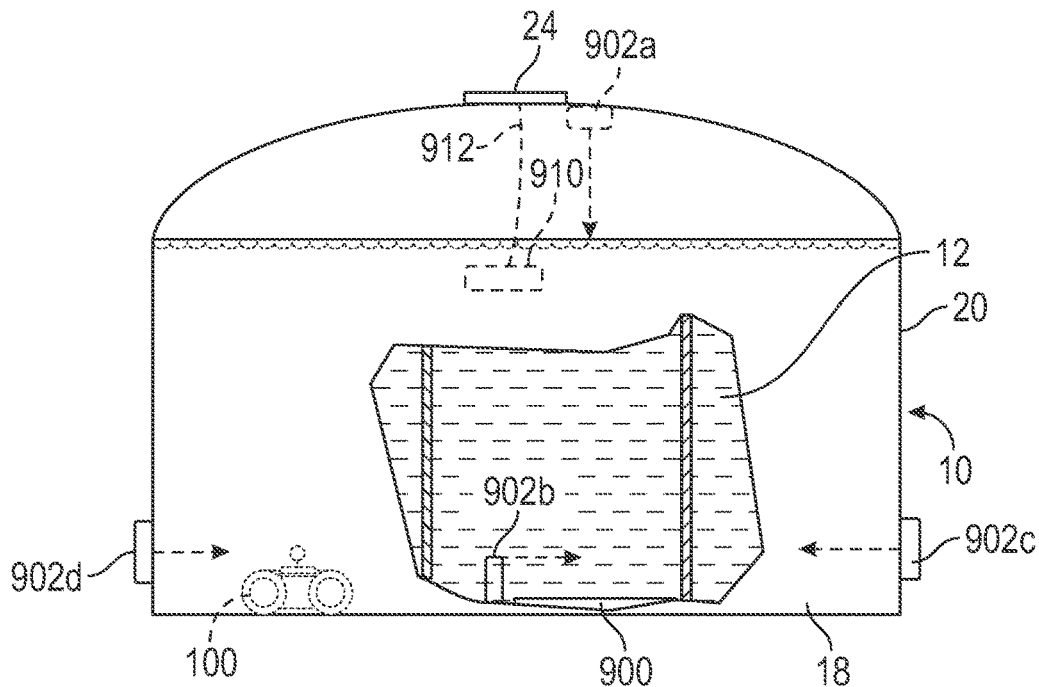
FIG. 17 is a partial sectional view of a tank having active markers according to embodiments of the present disclosure.

Referring now to FIG. 17, there are shown several types of markers that may be used to control the movement of the mobile platform 100 in the tank 10. By interacting with these markers, the control unit 300 (FIG. 2) acquires an awareness of the location and/or orientation of the mobile platform 100 relative to a given location in the tank 10.

A structural marker such as a discontinuity may be considered a passive marker. By passive, it is meant that the marker is inert and does not originate a signal detected by the mobile platform 100. Another type of marker is energy emitting objects 902a,b,c,d or 'active markers,' that emit a magnetic, electromagnetic, acoustic, and/or optical signal. Active markers may be positioned inside and/or outside of the tank 10. For example, FIG. 17 depicts internal active markers 902a,b and external active markers 902c,d. Active markers may be utilized in a variety of methodologies. For example, a central internal active marker can be using by the mobile platform 100 as a homing beacon to identify a particular location in the tank 10. Two or more spaced apart active markers may be used by the mobile platform 100 to locate itself and/or a direction within the tank 10.

In some embodiments, a marker is not rigidly fixed to the tank 10. For example, a marker 910 may float in a liquid body 12. The marker 910 may float at the surface or be submerged at a selected depth below the surface. Optionally, a tether 912 may connect the marker 910 to the tank 10. The marker 910 may be active; e.g., transmit an energy signal such as an acoustic wave. The marker 910 may also be passive; e.g., hang at a depth low enough as to allow contact with the mobile platform 100.

Figure 18A:
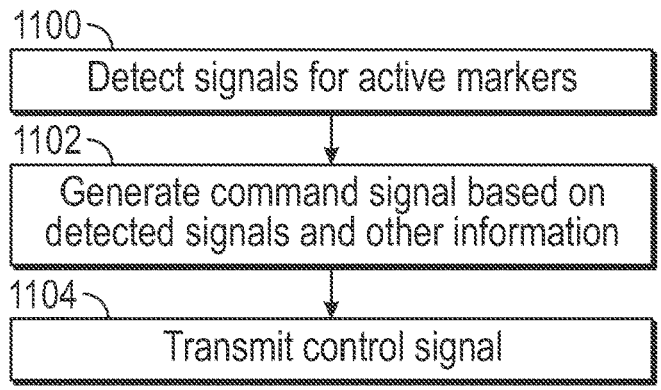
FIGS. 18A-B are flow charts illustrating alternate methods for steering mobile platforms according to the present disclosure.
Figure 18B:
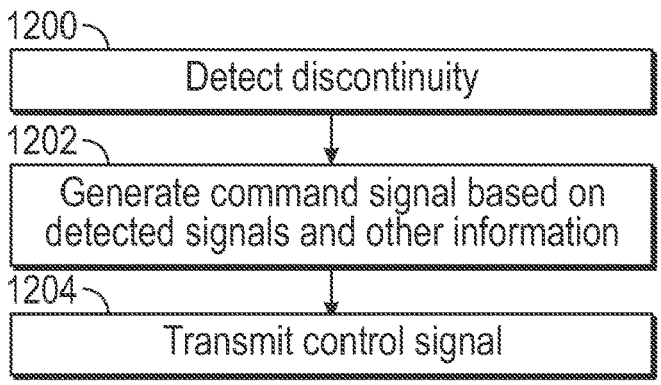

FIGS. 18A-B are flow charts of various guidance and navigation methodologies that may use the above-described markers.

Referring to FIGS. 12A-B, 13, 17 and FIG. 18A, the control unit 300 processes signals from active markers in order to generate command signals to operate the mobile platform 100. For example, at step 1100, the marker detector 306 may detect distinct signals emitted by a plurality of internal and/or external markers 902a-d. At step 1102, the control unit 300 may process the signals to estimate a current position of mobile platform 100. Optionally, the control unit 300 may also use pre-programmed information such as the dimensions of the tank 10, relative locations of the active markers 902a-d, as well as navigation parameters such as real-time information pertaining to orientation and direction of movement obtained by dynamic sensors 380. At step 1104, the control unit 300 issues a command signal to a subsystem such as a propulsion system 400 or the task module 600.

Referring still to FIGS. 12A-B, 13, and 17, in the FIG. 18A and FIG. 18B methods, the control unit 300 may have one or more memory modules 390, 392. The memory module 390 stores information collected during operation. This information may be dynamically updated and include information such as position of markers and current position/heading/orientation of the mobile platform 100. The memory module 390 may also store measured data indicative of the thickness of walls 16, 18, 20 of the tank 10. The memory module 392 may include preprogrammed data that may be accessed while the mobile platform 100 is operating. The preprogrammed data may be a digital representation (or map) of a discontinuity pattern of one or more walls of the tank 10. The discontinuity may be the weld/overlap pattern of one or more walls 26, 18, 20 of the tank 10. This information may have been obtained during a previous operation in the tank. At step 1200, the marker detector 306 may detect the discontinuity and generate responsive signals. At step 1202, the control unit 300 may process the marker detector signals along with the information in the stored map to estimate a current position and/or orientation of mobile platform 100. At step 1204, the control unit 300 issues a command signal to a subsystem such as a propulsion system 400 or a task module 600.

Other navigation and guidance schemes may define a point and a line, such as an edge leading to a tank wall or by any two points. A mobile platform 100 using such a scheme may have a control unit 300 programmed to estimate distances traveled using "dead reckoning" (e.g., by counting wheel revolutions). Suitable sensors in the propulsion system 400 may be used to sense when progress has been impeded by an obstacle (e.g., power variance) and/or travel reasonably straight without external references (e.g., RPM sensors on wheels, drive shaft, rotor, or other rotating element of the propulsion system). Optionally, an internal navigation unit may be used to supplement navigation. The control unit 300 may be programmed to generate a "map" and proceed methodically through the tank 10 by referencing the map and performing the dead reckoning. The map, and any information gathered such as wall thickness data, may be correlated with the actual layout of the tank using common pattern mapping techniques.

Still another navigation method may not use sense/detect markers or use inertial navigation units. Instead, the mobile platform 100 may be programmed to traverse the tank 10 and take pre-assigned actions when encountering obstacles (e.g., turn until travel is unimpeded). Any information gathered, such as wall thickness data, may be correlated with the actual layout of the tank using common pattern mapping techniques.

The methodologies discussed above are not mutually exclusive. That is, portions of each of the described methods may be blended or separate methodologies may be used concurrently. Some navigating methods involve generating a 'map' while performing one or more assigned functions. Other methods involve using a previously generated map in order to navigate to one or more predetermined locations.

From the above, it should be appreciated that what has been disclosed includes, in part, an apparatus for performing a selected task in a tank at least partially filled with an energetic substance. The apparatus may include an inherently safe mobile platform that comprises at least one control unit, at least one marker detector, at least one propulsion system, at least one power supply, and at least one inherently safe enclosure.

The at least one inherently safe enclosure is configured to prevent a spark occurring inside the at least one inherently safe enclosure from passing to an exterior of the at least one inherently safe enclosure, the spark being capable of igniting the energetic substance. All spark-generating components of the mobile platform are positioned inside the at least one inherently safe enclosure.

The at least one marker detector is configured to detect at least one marker associated with the tank. The at least one control unit is configured to generate at least one control signal based on the at least one detected marker. The propulsion system moves the mobile platform in response to the at least one generated control signal. The propulsion system has a rotary power device positioned inside the at least one inherently safe enclosure that supplies power to a drive assembly positioned outside the at least one inherently safe enclosure. The power supply energizes at least the at least one marker detector, the at least one control unit, and the at least one rotary power device. No active physical carrier connects the mobile platform to an object exterior of the tank while the mobile platform is in the tank.

Variants of the mobile platform may include arrangements wherein: the at least one inherently safe enclosure is configured to not exhibit plastic deformation that forms a path allowing a spark occurring inside the at least one inherently safe enclosure from passing to an exterior of the at least one inherently safe enclosure after an interior of the at least one inherently safe enclosure is subjected to at least three and one-half bar for at least ten seconds; the mobile platform is configured to have at least two different degrees of freedom in the tank and to move along the at least two different degrees of freedom using the propulsion system; the mobile platform weighs less than 10,000 pounds (4,536 kg); the at least one control unit is programmed to determine a heading for the mobile platform based on the at least one detected marker, the heading being used to generate the at least one control signal; there are no physical carriers connecting the mobile platform to an object outside the tank; and/or the at least one power supply supplies sufficient power to fully energize at least the at least one control unit, the at least one marker detector, and the at least one propulsion system. Also, in variants, the apparatus may include a passive carrier connected to the mobile platform while the mobile platform moves in the tank.

In certain applications, the energetic substance is a liquid that contacts the mobile platform and an interior surface of the tank to form a wave transmitting medium. In such applications, the mobile platform is configured to transmit a wave and detect a reflection of the transmitted wave. The mobile platform can store information representative of the detected reflection in a memory module.

Further, while the above-described embodiments of the mobile platform 100 do not use a physical umbilical to receive power and/or communicate data, it is within the scope of the present disclosure that a mobile platform 100 may incorporate a carrier. The carrier may be a signal conveying media, e.g., a conducting cable or simply a cable that may effectively "leash" the mobile platform 100 to another object.

Referring to FIG. 1, it should be noted that structures for storing energetic substances (12, 14), such as the tank 10, may be constructed in a manner that can hinder the deployment into and retrieval out of an interior 22 of the tank 10. For example, access to the interior 22 may only be available through the hatch 24, which is positioned on the top wall 16. In many instances, access to objects in the interior 22 is limited to the zone or area in the immediate vicinity of the hatch 24. Limitations in the ability to detect the presence of an object, to identify the object, and/or manually reach and contact the object generally define such a zone or area. For instance, objects located immediately adjacent to the vertical wall 20 may be undetectable to personnel and not physically accessible without expending considerable effort and employing relatively complex lifting and handling equipment. Moreover, the interior 22 may contain energetic substances (12, 14), which may be non-conductive, that may require additional restrictions to the retrieval activity. As noted above, some classes of hydrocarbon liquids and gases are non-conductive. However, the teachings of the present disclosure may be readily applied to environments wherein energetic and/or non-conductive substances are not present. Certain teachings of the present disclosure are directed to facilitating retrieval of mobile platforms deployed in such environments.

Figure 19:
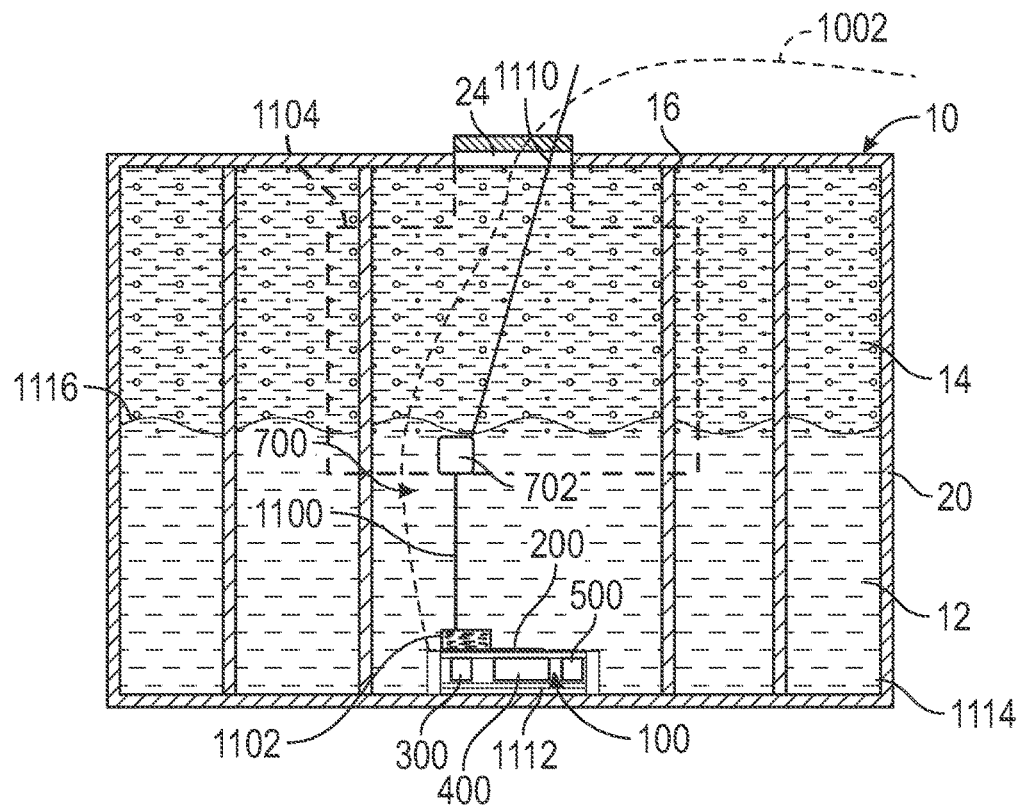
FIG. 19 illustrates a system for retrieving a mobile platform using a primary and a secondary tether according to an embodiment of the present disclosure.

Exemplary retrieval devices and related methods have already been discussed in connection with FIGS. 11A-D, 15, and 16B. Referring now to FIG. 19, there is schematically illustrated another non-limiting embodiment of the retrieval module 700 configured and implemented to simplify locating and retrieving the mobile platform 100 from inside the tank 10.

For simplicity, the mobile platform 100 to be retrieved may be configured to include an enclosure 200, a control unit 300, a propulsion system 400, and a power supply 500. These components and sub-systems have been already discussed above and will not be described in further detail. It is emphasized that the configuration of these components and sub-systems are not limited to any particular previously described embodiment. For example, the enclosure 200 need not be inherently safe. Moreover, two or more enclosures may form the enclosure 200, with each of these separate enclosures acting as housing structures for different components. Further, optionally, the mobile platform 100 may be used in conjunction with a carrier 1002, which may be a passive or active carrier. Such carriers have already been described and will not be described in further detail.

The mobile platform may include a retrieval module 700 disposed at least partially on the enclosure 200. That is, the parts making up the retrieval module 700 may be internal and/or external to the enclosure 200. Also, some parts may be embedded in a wall or body of the enclosure 200. In one arrangement, the retrieval module may include a buoyant body 702, a primary tether 1100, and a secondary tether 1102. The buoyant body 702 is similar to that previously described. The primary tether 1100 may be the same as the tether 738 of FIG. 11B.

In one arrangement, the primary tether 1100 and the secondary tether 1102 are directly connected to one another, the primary tether 1100 directly connects to the buoyant body 702, and the secondary tether 1102 directly connects to the enclosure 200. An example of this configuration is illustrated in FIG. 11B, wherein the primary tether 1100 is formed by the first stage tether 738 and the flexible member 742 and the secondary tether 1102 is formed by the second stage tether 740. It should be noted that in this arrangement while the first stage tether 738 and 742 is shown as attached to the enclosure 200, the attachment is not one through which a force, such as tension, is intended to be transmitted during retrieval of the mobile platform 100. Thus, as used herein, the term "connection" refers to a functional engagement wherein there is a communication of force (e.g., tension) or signals (i.e., power or data) between two or more locations as opposed to merely holding one body stationary relative to another body.

In the FIG. 11B arrangement, the primary tether 1100 is indirectly connected to the enclosure 200 via the secondary tether 1102 and the secondary tether 1102 is indirectly connected to the buoyant body 702 via the primary tether 1100. By "indirect" connection, it is meant that physical engagement occurs through an intervening and functionally distinct device or component.

Figure 20A:
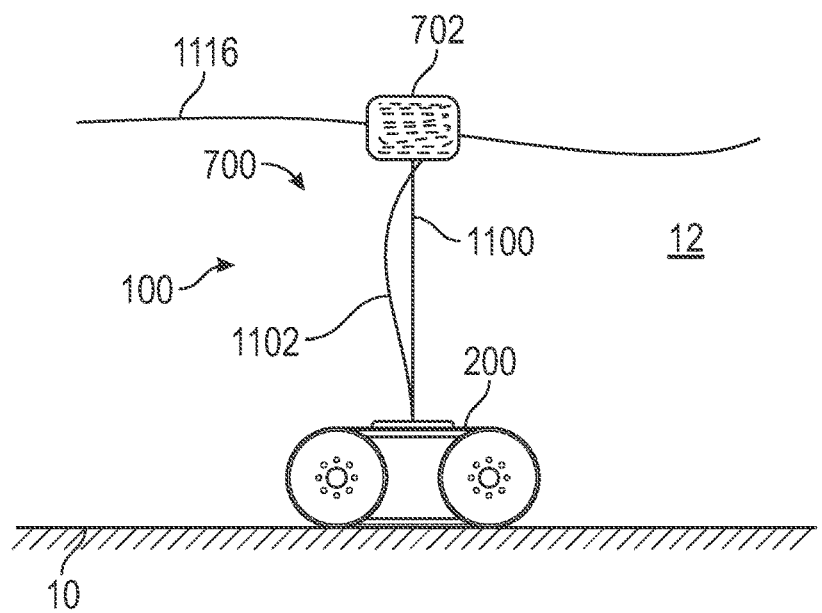
FIGS. 20A-B schematically illustrate an embodiment wherein a primary and a secondary tether are connected to a buoyant body according to the present disclosure.

Referring now to FIG. 20A, in another arrangement, the primary tether 1100 and the secondary tether are both directly connected to the buoyant body 702 and to the enclosure 200. It should be noted that the direct connection may include one or more elements specifically configured to form a connection, such as a chain, cable, or buckle. For instance, a portion of the secondary tether 1102 may be used to connect the primary tether 1100 to the buoyant body 702. A cavity, reel, or spool (not shown) inside or outside the buoyant body 702 may be used to store a length of the secondary tether 1102.

Figure 20B:
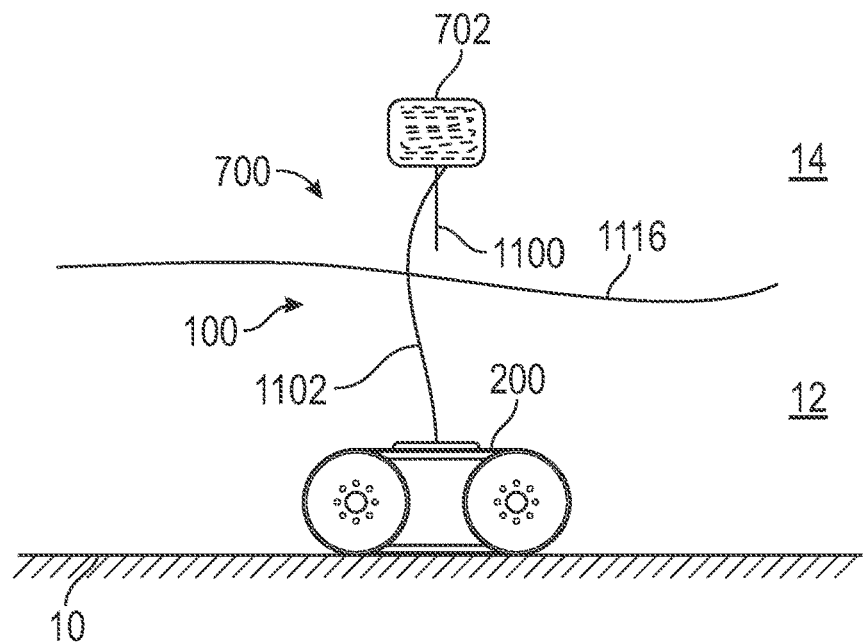

In the FIG. 20A arrangement, the primary tether 1100 is configured to release the secondary tether 1102 by severing in some manner. For instance, the connection between the primary tether 1100 and the enclosure 200 can be broken by using a suitable breaking force or by transmitting a signal. FIG. 20A shows the retrieval module 700 after the buoyant body 702 has been released and rises toward a surface 1116 of the non-conductive, liquid energetic substance 12. The primary tether 1100 connects the buoyant body 702 to the enclosure 200, while the secondary tether 1102 is not under tension at a magnitude occurring during the retrieval of the mobile platform 100. FIG. 20B shows the retrieval module 700 of FIG. 20A after the primary tether 1100 has been disconnected from the enclosure 200 and the buoyant body 702 has been extracted from the non-conductive, liquid energetic substance 12. In alternate embodiments, the primary tether 1100 could decouple from only the buoyant member 702 or decouple from both the enclosure 200 and the buoyant member 702. The primary tether 1100 may also sever at an intermediate location thereby releasing the buoyant member 702 from the enclosure 200 while having a severed portion connected to both. Now, the secondary tether 1102 can act as a load bearing retrieval member for pulling up the mobile platform 200 toward the surface 1116 of the non-conductive, liquid energetic substance 12.

Figure 20C:
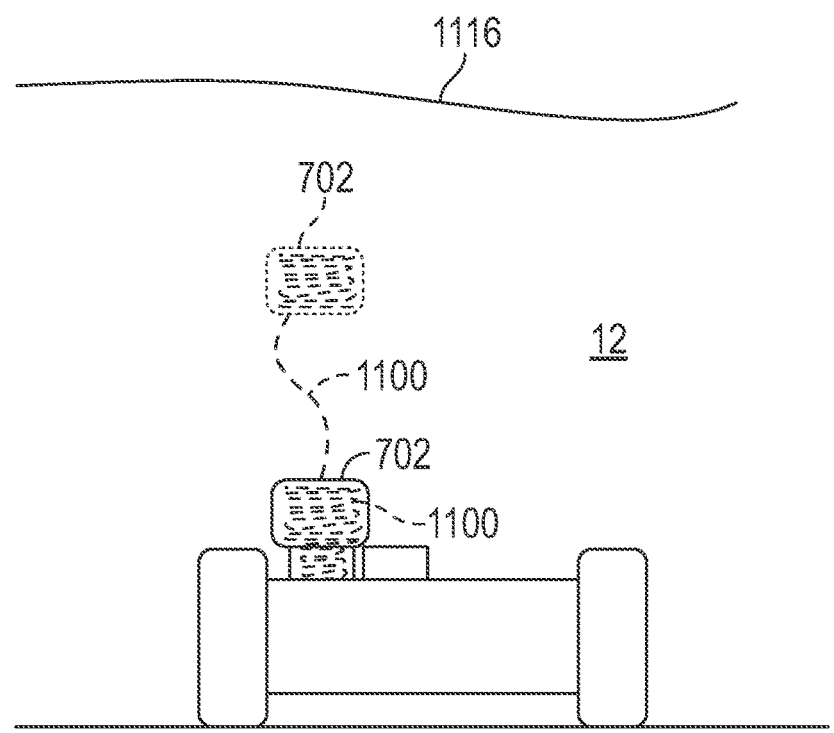
FIG. 20C schematically illustrates an embodiment wherein a tether is stored and released from a buoyant body according to the present disclosure.

Referring to FIG. 20C, there is shown another arrangement wherein the primary tether 1100 is housed within the buoyant body 702. When activated, the buoyant body 702 rises toward a surface 1116 of the non-conductive, liquid energetic substance 12. As the buoyant body 702 rises, the primary tether 1100 unspools, falls, or otherwise exits the buoyant body 702.

While illustrated as single, unitary bodies, it should be understood that the buoyant body 702, the primary tether 1100, and the secondary tether 1102, may be formed of two or more separate portions, sections, or segments.

Figure 21:
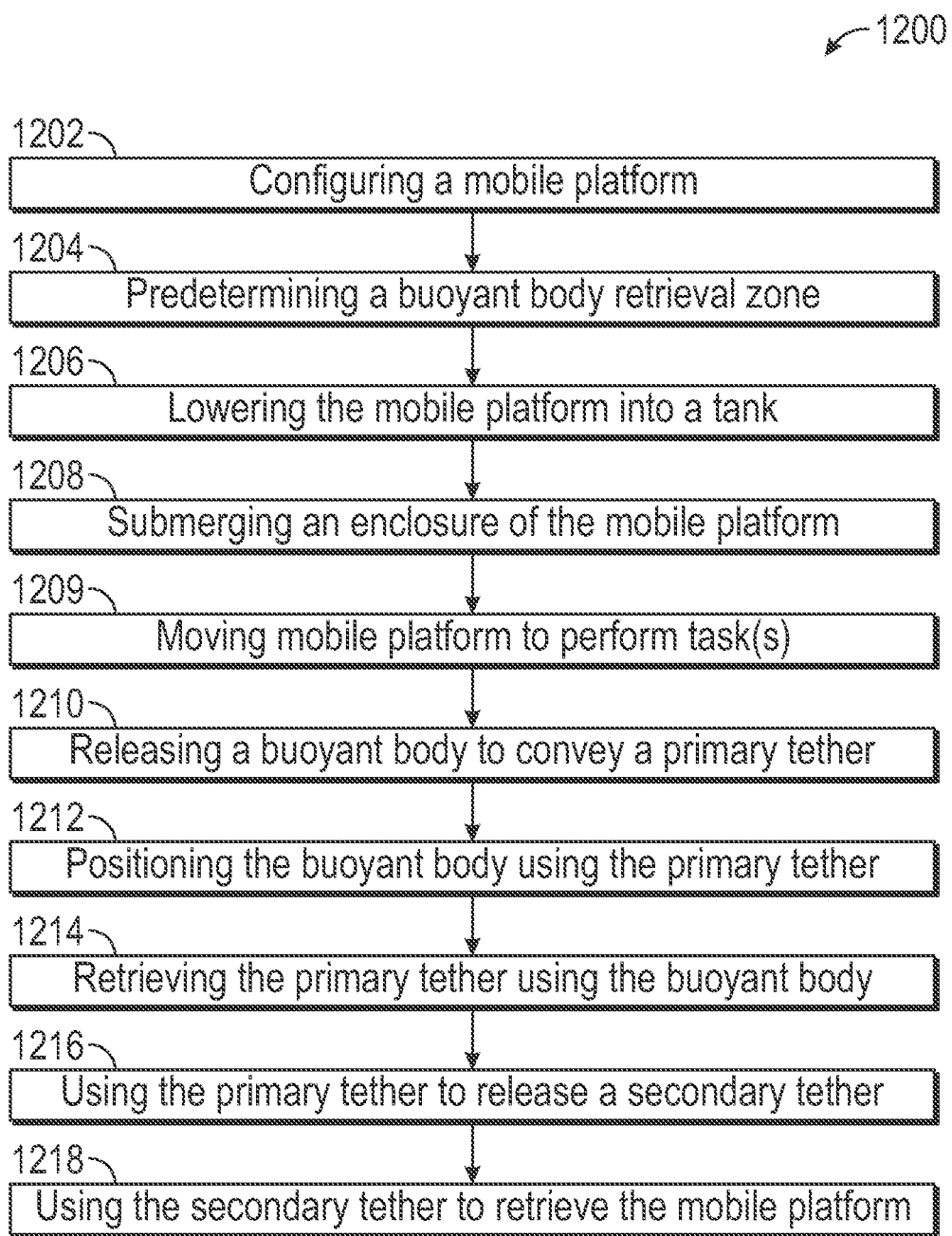
FIG. 21 is a flow chart illustrating an embodiment of a retrieval method according to the present disclosure that uses the systems and devices of FIG. 19 and FIGS. 20A-C.

FIG. 21 illustrates a non-limiting embodiment of a retrieval method 1200 according to the present disclosure. Referring to FIGS. 19 and 20A,B, the method 1200 may be of particular use when the tank 10 is at least partially filled with a non-conductive, energetic substance 12, 14. At step 1202, the mobile platform 100 may be configured as shown in FIG. 19. However, the method 1200 may be used to retrieve other devices not described in the present disclosure. At step 1204, personnel may predetermine the buoyant body retrieval zone 1104 within the tank 10. It should be noted that the hatch 24 permits relatively easy access to certain interior areas of the tank 100 directly below the hatch 24. However, because the hatch 24 is much smaller than the top 20, limits access to areas closer to the vertical wall 20. Thus, the buoyant body retrieval zone 1104 may be based on the limitation in lifting, handling, and access associated with performing retrievals through the hatch 24.

At step 1206, the mobile platform 100 is lowered into the tank 10 using a deployment carrier 50 (FIG. 16A). Other embodiments may use the deployment carriers 764 or 780 (FIGS. 11C, 11D, respectively). At step 1208, the enclosure 200 is submerged in the non-conductive, liquid energetic substance 12. If two or more separate enclosures are present, then only one of those separate enclosure needs be submerged. Moreover, the enclosure 200 does not have be fully submerged; i.e., a partially submerged state may be suitable in certain instances. At step 1209, the mobile platform 100 may be moved by the propulsion system 400 to perform one or more tasks in the tank 10.

At step 1210, which may be at or near the conclusion of operations, the buoyant body 702 is released from the enclosure 200. It should be noted that the buoyant body 702 and the primary tether 1100 are still connected to the enclosure 200 by the secondary tether 1102. The step 1212, positioning of the released buoyant body 702 occurs within the buoyant body retrieval zone—1106 by using the at least one primary tether 1100. At step 1214, retrieving the primary tether 1100 is performed by using the buoyant body 702. For example, a retrieval member 1110 may be inserted into the tank 10 through the hatch 24 to capture the buoyant body 702. The retrieval member 1110 may be a pole, hook, lasso, net, rod or other elongated member. At step 1216, the primary tether 1100 may be used to release the secondary tether 1102. For instance, the primary tether 1100 may be used to transmit a force or signal to the secondary tether 1102. Suitable forces or signals may be tension, torsion, vibration, etc. At step 1218, the secondary tether 1102 is used to retrieve the mobile platform 100 from inside the tank 10 to outside the tank 10. The retrieval member 1110 may be inserted through the hatch 24 to retrieve the buoyant body 702, the primary tether 1100, and/or the secondary tether 1102. It should be noted that other devices such as the primary tether 1100 and/or additional cables, wires, or other retrieval members may be used in conjunction with the secondary tether 1102 to retrieve the mobile platform 100.

In embodiments, the primary tether 1102 may be configured to position the buoyant body 702 in the buoyant body retrieval zone 1104 by estimating a height of the non-conductive, liquid energetic substance 12 above the mobile platform 100 inside the tank 10 and selecting a length of the primary tether 1100 based, at least in part, on the estimated height of the non-conductive, liquid energetic substance 12 above the mobile platform 100 inside the tank 10. In some methods, the length of the primary tether 1100 is also selected using, at least in part, a distance between a retrieval location—1112 of the mobile platform 100 and a wall 20 of the tank 10. In other methods, the length of the primary tether 1110 is less than the square root of the sum of the square of the estimated height of the non-conductive, liquid energetic substance 12 above the mobile platform 100 inside the tank 10 and the square of a distance from the retrieval location 1112 of the mobile platform 100 to a farthest point 1114 on the wall 20 of the tank 10 at a level of the retrieval location 1112.

As discussed previously in connection with FIG. 19, the primary tether 1100 may be used to release the secondary tether 1102. In one arrangement, the primary tether 1100 is configured to release the secondary tether 1102 in response to an applied predetermined releasing force. The releasing force may be selected to actuate a lever, break a frangible element, overcome frictional force, overcome a pre-tension in an object, bend, twist, or otherwise deform an object, overcome stored tension or spring force, or otherwise decouple the secondary tether 1102 from a suitable retaining mechanism. During retrieval, applying a force that is at least as great as the predetermined releasing force to the primary tether 1100 releases the secondary tether 1102. In one non-limiting method, the predetermined releasing force is greater than a net buoyancy of the buoyant body 702 in the non-conductive, liquid energetic substance 12 and less than a net downward force of the mobile platform 100 in the non-conductive, liquid energetic substance 12.

Additional variants of the method 1200 include sizing the secondary tether to be at least long enough to traverse a distance between the mobile platform 100 and a location proximate to a top wall 16 of the tank 100 and selecting a combined length of the primary tether 1100 and the secondary tether 1102 is at least long enough to traverse a distance between the mobile platform 100 and a location proximate to a top wall 16 of the tank 100. One skilled in the art would understand that what is "proximate" will depend on a position of the buoyant body 702 that is close enough for personnel to reach and retrieve the buoyant body 702 or primary tether 1100 from the hatch 24.

In some applications, the secondary tether 1102 is used to pull the mobile platform 100 either partially or fully out of the tank 10. For example, the secondary tether 1102 may be used to pull up and support the mobile platform 100 at a surface 1116 of the non-conductive, liquid energetic substance 12. Alternatively, the secondary tether 1102 may be used to lift the mobile platform 100 out of the non-conductive, liquid energetic substance 12. In situations such as when a floating roof is present, the length of the primary tether 1100 may be selected to maintain a predetermined gap between the buoyant body 702 and a top wall 16 of the tank 10.

Referring to FIGS. 1 and 2, in certain situations, it may be desirable to reduce a voltage differential between the mobile platform 100 and the tank 10 and/or other surrounding electrically conductive structures before completing retrieval of the mobile platform 100. Such a voltage differential may arise from an accumulation of electrical charge on the mobile platform 100 due to relative motion between the mobile platform 100 and contact with an adjacent surface and/or the operation of consumers of electrical energy onboard the mobile platform 100. The adjacent surface may be a surface defining a wall 16, 18, 20 of a tank 10, a pillar 26 of a tank 10, and/or the non-conductive, liquid energetic substance 12. Exemplary electrical power consumers include, but are not limited to, the control unit 300, the marker detector 306 (FIG. 4), the dynamic sensor 380 (FIG. 13), the propulsion system 400, and the task module 600 (FIG. 2). The type and number of electrical power consumers will depend on the particular configuration of the mobile platform 100. For simplicity, the term "on" will be used herein to describe an electrical charge accumulation "on" and "in" the mobile platform 100.

Further, while partially or completely submerged in the non-conductive, liquid energetic substance 12, the mobile platform 100 may be electrically isolated from the tank 10 by the non-conductive, liquid energetic substance 12 and possibly other non-conductive material. Such other non-conductive material may include paint, coatings, rust, and/or sludge. Electrical isolation may also occur if the mobile platform 100 is partially or completely immersed in a non-conductive, gaseous energetic substance 14 inside the tank 10. When encountering such electrical isolation, the rate of electrical charge dissipation from the mobile platform 100 may be lower than the rate of electrical charge accumulation, which may cause a relevant amount of electrical charge accumulation on the mobile platform 100.

Figure 22:
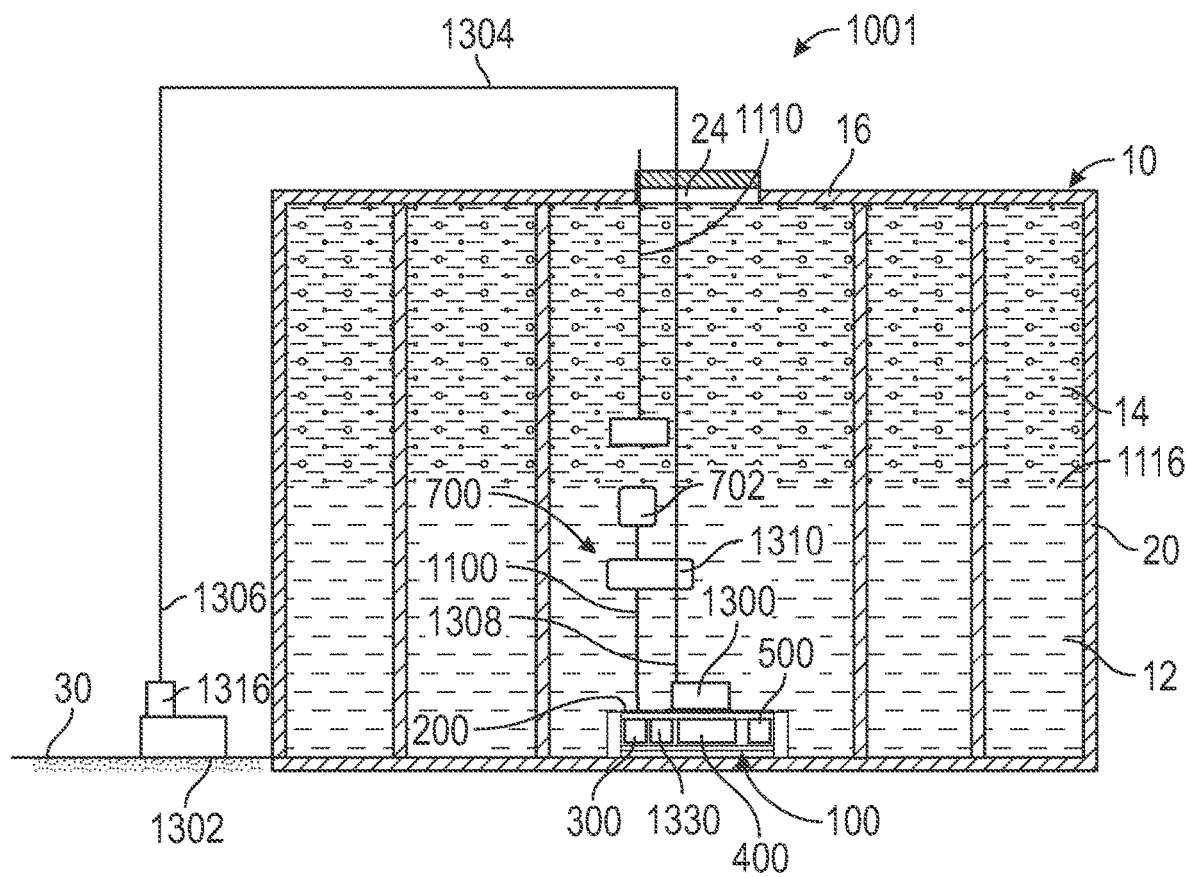
FIG. 22 illustrates a system for retrieving a mobile platform that reduces an electrical charge on the mobile platform according to an embodiment of the present disclosure.

Referring now to FIG. 22, there is shown a non-limiting embodiment of a retrieval system 1001 for retrieving a mobile platform 100 from a tank 10 at least partially filled with a non-conductive, energetic substance 12, 14. As described below, the retrieval system 1001 may be used to reduce and/or minimize this charge accumulation before or during the retrieval of the mobile platform 100 from inside the tank (10) to outside the tank (10).

The mobile platform 100 to be retrieved may be configured to include an enclosure 200, a control unit 300, a propulsion system 400, and a power supply 500. These components and sub-systems have been already discussed above and will not be described in further detail. A generic electrical power consumer is shown with numeral 1330, which is representative of any device that consumes electrical power, including but not limited to, the control unit 300, the marker detector 306 (FIG. 4), the dynamic sensor 380 (FIG. 13), the propulsion system 400, the task module 600 (FIG. 2), and/or any device not described in the present specification that consumes electrical power. As noted previously, the configuration of these components and sub-systems are not limited to any previously described embodiment, e.g., the enclosure 200 need not be inherently safe and the mobile platform 100 may be used in conjunction with a carrier (not shown), which may be a passive or active carrier. Also, two or more enclosures may form the enclosure 200, with each of these separate enclosures acting as housing structures for different components. Moreover, other mobile platforms may include additional components or fewer components.

The mobile platform 100 also includes a retrieval module 700 disposed at least partially on the enclosure 200. That is, the parts making up the retrieval module 700 may be internal and/or external to the enclosure 200. Also, some parts may be embedded in a wall or body of the enclosure 200. In one arrangement, the retrieval module 700 may include a buoyant body 702, a tether 1100, and an electrically conductive member 1300. The retrieval system 1001 further includes a voltage differential neutralizing body 1302 and an electrically conductive cable 1304.

In one embodiment, the tether 1100 connects the buoyant body 702 to the enclosure 200, the tether having at least a portion that is not conductive. Because the tether 1100 electrically isolates the buoyant body 702 from the enclosure 200, proximity or contact with the buoyant body 702, or the tether 1100 near the buoyant body 702, will not form an electrical connection between the buoyant body 702 and the enclosure 200. That is, at least a portion or section of the tether 1100 is sufficiently not conductive to prevent a transmission of electrical energy between the buoyant body 702 and the enclosure 200. The buoyant body 702 is similar to that previously described. In configurations where the tether 1100 is fully submerged in the non-conductive, liquid energetic substance 12, the tether 1100 may not need to have a portion that is not conductive.

The electrically conductive member 1300 may be an object, body, plate, coating, or structure that is electrically connected to one or more regions on the enclosure 200. The electrical connection is sufficient to transfer some, substantially all, or all of the electrical charge accumulated in and/or on the enclosure 200 to any electrically conductive object in electrical communication with the electrically conductive member 1300, assuming the appropriate voltage differential exists. The voltage differential neutralizing body 1302 may be an object, device, body, plate, coating, or structure into which an electrical charge can be discharged. In some arrangements, the tank 10 or ground 30 can act as the voltage differential neutralizing body 1302. The electrically conductive cable 1304 may be a conventional cable configured to transmit electrical energy between a neutralizing body end 1306 and a mobile platform end 1308. In embodiments, the electrically conductive cable 1304 may include an insulating outer sheath (not shown).

Figure 23:
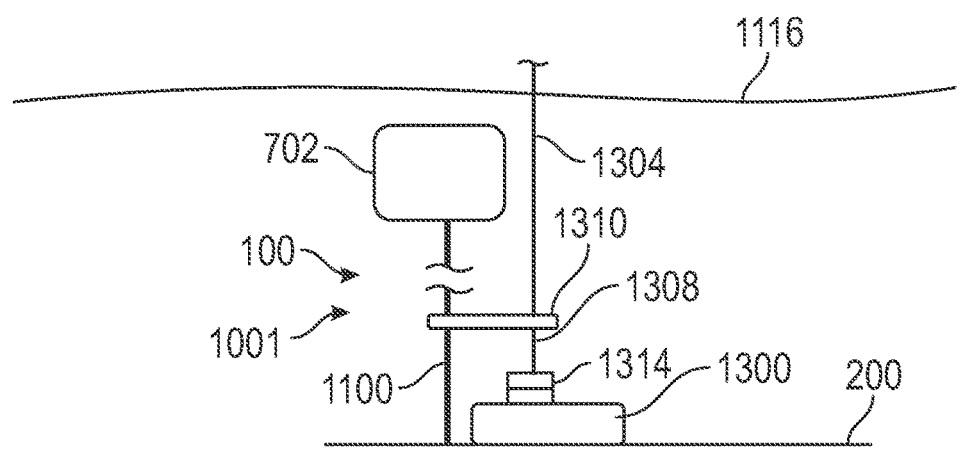
FIG. 23 illustrates an electrical connection between an electrically conductive cable and an electrically conductive member on an enclosure of a mobile platform according to embodiments of the present disclosure.

Referring now to FIG. 23, there is shown a conveyance device 1310 for conveying the mobile platform end 1308 of the electrically conductive cable 1304 to the electrically conductive member 1300 on the enclosure 200 of the mobile platform 100. The conveyance device 1310 may be a harness, ring, sleeve or other suitable sliding member that can slide along the tether 1100. The conveyance device 1310 has sufficient mass to pull the mobile platform end 1308 downward to the electrically conductive member 1300. The mobile platform end 1308 may include a suitable connector 1314 that electrically connects to the electrically conductive member 1300. There may be a direct physical connection between the connector 1314 and the electrically conductive member 1300 or an indirect connection that allows electrical communication. The electrically conductive member 1300 is shown as electrically connected to one localized region of the enclosure 200. However, in embodiments, the electrically conductive member 1300 may be in electrical communication with two or more discrete regions of the enclosure 200 at which electrical charges may accumulate. Referring to FIG. 22, the neutralizing body end 1306 of the electrically conductive cable 1304 may include a suitable connector 1316 that electrically connects to the voltage differential neutralizing body 1302. Likewise, the connection may be a direct physical connection or an indirect connection.

While illustrated as single, unitary bodies, it should be understood that the described devices, including, but not limited to the buoyant body 702, and the tether 1100, the electrically conductive member 1300, may be formed of two or more separate portions, sections, or segments. Further, as discussed previously, components of the mobile platform 100, such as the enclosure 200, may be formed of two or more separate enclosures.

Additionally, some variants of the retrieval module 700 of FIGS. 11A, B and 19 include a primary tether 1100 that is constructed to be buoyant in the liquid energetic material 12. For example, the primary tether 1100 may include one or more materials that make the primary tether 1100 positively buoyant in the liquid energetic material 12. Alternatively or additionally, the primary tether 1100 may include buoyant bodies distributed along the length of the primary tether 1100. In such variants, the buoyant body 702 is considered integral with the primary tether 1100.

Figure 24:
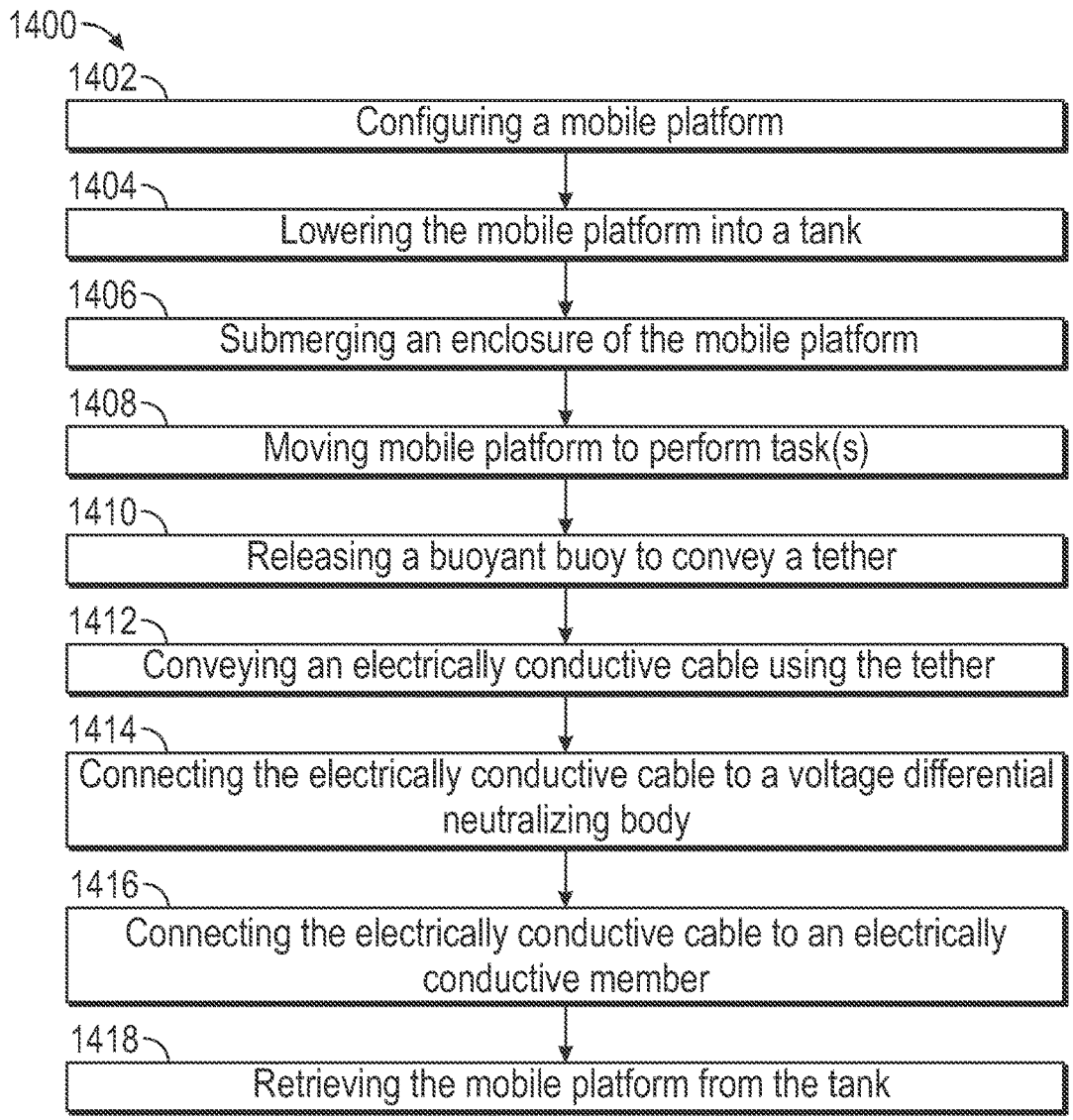
FIG. 24 is a flow chart illustrating a retrieval method according to one embodiment of the present disclosure that uses the FIG. 22 system.

FIG. 24 illustrates a non-limiting embodiment of a retrieval method 1400 according to the present disclosure that employs the retrieval system 1001 of FIGS. 22 and 23. The method 1400 may be of particular use when the tank 10 is at least partially filled with a non-conductive, energetic substance 12, 14. At step 1402, the mobile platform 100 to be retrieved may be configured as shown in FIG. 22. However, the method 1400 may be used to retrieve other mobile devices not described in the present disclosure.

At step 1404, the mobile platform 100 is lowered into the tank 10 using a deployment carrier 50 (FIG. 16A). Other embodiments may use the deployment carriers 764 or 780 (FIGS. 11C, 11D, respectively) or other suitable systems for lowering the mobile platform 100 into the tank 10. At step 1406, the enclosure 200 is submerged in the non-conductive, liquid energetic substance 12. If two or more separate enclosures are present, then only one of those separate enclosure needs be submerged. Moreover, the enclosure 200 does not have to be fully submerged; i.e., a partially submerged state may be suitable in certain instances. It should be noted after step 1406, some components used in conjunction with the mobile platform 100, such as an active or passive carrier (not shown) may not be submerged. At step 1408, the mobile platform 100 is moved using the propulsion system 400. The movement may be in connection with performing an assigned task or some other function. At step 1410, which may be at or near the conclusion of completing the assigned task(s) and/or function(s), the buoyant body 702 is released to convey the tether 1100 toward a surface 1116 of the non-conductive, liquid energetic substance 12.

At step 1412, the electrically conductive cable 1304 is conveyed to the electrically conductive member 1300 of the mobile platform 100 using the tether 1100. At step 1414, the neutralizing body end 1306 of the electrically conductive cable 1304 is connected to the voltage differential neutralizing body 1302 in a "spark inhibiting ambient condition." As used herein, a spark inhibiting condition is a condition wherein ambient conditions in which the connection is being made are sufficiently deficient in oxygen and/or an energetic substance to preclude a spark from igniting an energetic substance, if such an energetic substance is present.

At step 1416, the mobile platform end 1308 of the electrically conductive cable 1304 is connected electrically to the electrically conductive member 1300 of the mobile platform 100 while the electrically conductive member 1300 is below the surface 1116 of the non-conductive, liquid energetic substance 12. A fully submerged condition is considered a "spark inhibiting ambient condition" due to a suitable deficiency of oxygen.

In conjunction with the execution of steps 1412, 1414, and 1416, the connector 1314 may be conveyed to the mobile platform 100 using the tether 1100 and connected electrically to the electrically conductive member 1300. Depending on the system used, an exemplary method may involve retrieving the buoyant body 702 with a retrieval member 1110, attaching an electrically conductive mobile platform end 1308 of the electrically conductive cable 1304 to the tether 1100, and sliding the electrically conductive mobile platform end 1308 along the tether 1100 to the mobile platform 100. Thereafter, the electrically conductive mobile platform end 1308 is connected electrically to the electrically conductive member 1300.

At step 1418, the mobile platform 100 is retrieved from inside to outside of the tank 10.

In variants, personnel may first estimate when a voltage differential between the mobile platform 100 and the tank 10 is below a predetermined value and thereafter retrieve the mobile platform 100 from inside to outside of the tank 10. The predetermined value may be a voltage differential that cannot generate a spark capable of igniting one or more energetic substances in or around the tank 10. The estimation may be based on measurements, theoretical calculations or modeling, and/or historical information.

Figure 25A:
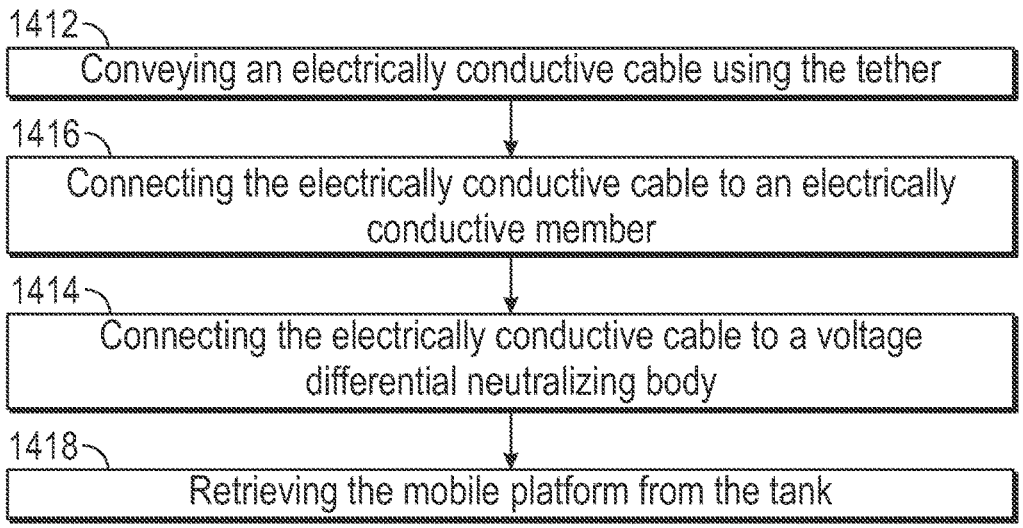
FIGS. 25A-B are flow charts illustrating alternate steps for making electrical connections when using the FIG. 24 method.

FIGS. 25A,B are flow charts depicting other sequences for electrical connection of the electrically conductive cable 1304 to the voltage differential neutralizing body 1302 and the electrically conductive member 1200.

In FIG. 25A, the steps 1414 and 1416 are be performed in reverse order. That is, step 1416, wherein the mobile platform end 1308 of the electrically conductive cable 1304 is connected electrically to the electrically conductive member 1300, can be performed before step 1414, wherein the neutralizing body end 1306 of the electrically conductive cable 1304 is connected to the voltage differential neutralizing body 1302.

Figure 25B:
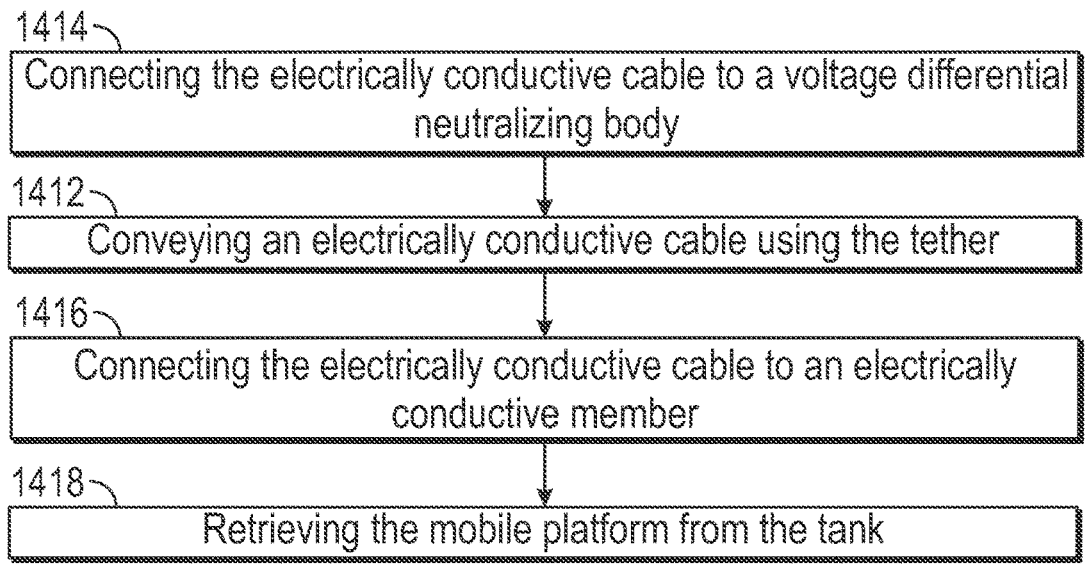

In the FIG. 25B method, the initial step is step 1414, wherein the neutralizing body end 1306 of the electrically conductive cable 1304 is connected to the voltage differential neutralizing body 1302. Next, step 1412 is taken, in which the electrically conductive cable 1304 is conveyed to the electrically conductive member 1300 of the mobile platform 100 using the tether 1100. Thereafter, step 1416 is taken, in which the mobile platform end 1308 of the electrically conductive cable 1304 is connected electrically to the electrically conductive member 1300. Finally, at step 1418, the mobile platform 100 is retrieved from inside to outside of the tank 10.

Figure 26:
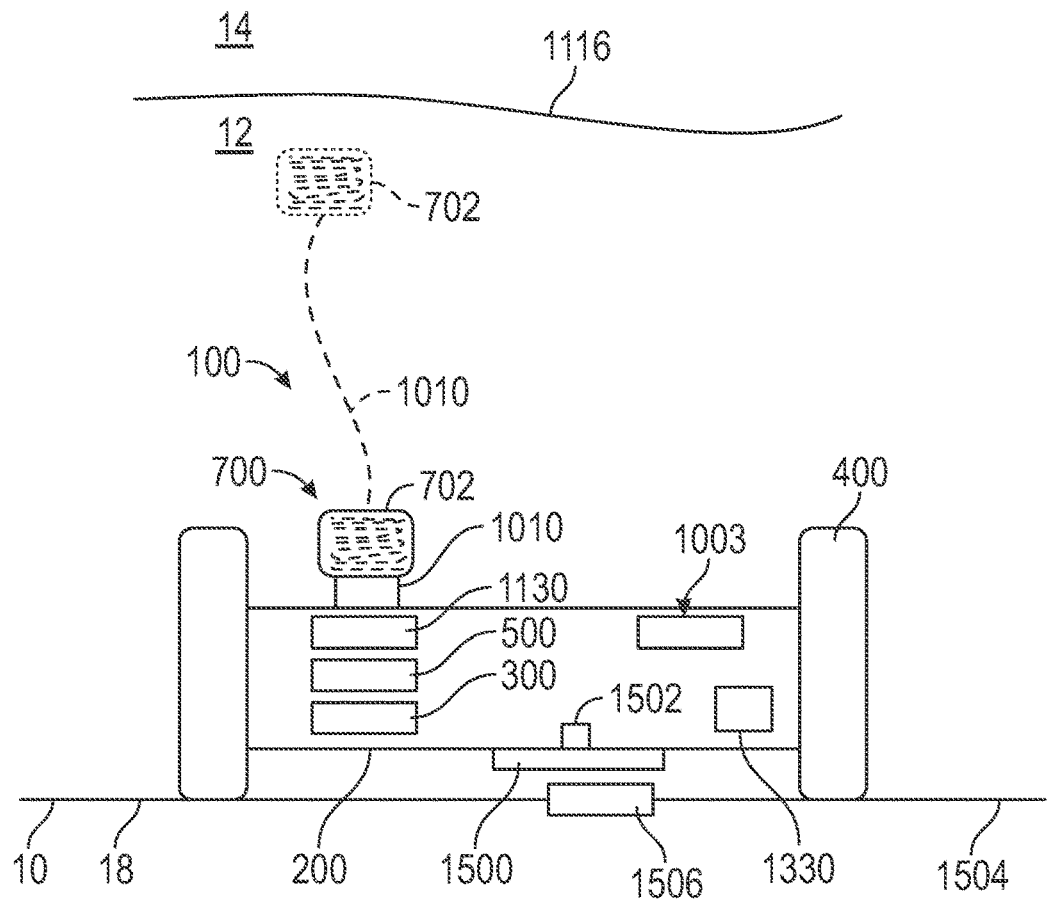
FIG. 26 illustrates a charge accumulation control system for a mobile platform according to an embodiment of the present disclosure.

As discussed previously in connection with the embodiment of FIG. 22, when the mobile platform 100 is operated in an environment that creates electrical isolation, the rate of electrical charge dissipation from the mobile platform 100 may be lower than the rate of electrical charge accumulation, which may cause a relevant amount of electrical charge accumulation on the mobile platform 100. FIGS. 10 and 26 illustrate non-limiting embodiments of a mobile platform 100 that uses a charge accumulation control system (CACS) to reduce and/or minimize this charge accumulation or the rate of increase of this charge accumulation prior to and during retrieval of the mobile platform 100.

In the FIG. 10 embodiment, a switch assembly 250 for communicating with the mobile platform 100 is described as configured to shift between power states, activate or deactivate sub-systems, initiate pre-programmed instructions, etc. Near or at the end of operations, the switch assembly 250 shifts to the "off" position, which shuts down the mobile platform 100. The shutdown of the mobile platform 100 effectively stops the relative motion between the non-conductive, liquid energetic substance 12 and the at least a portion of the mobile platform 100 contacting the non-conductive, liquid energetic substance 12 while the mobile platform 100 is inside the tank 10 and prevents any such relative motion later while the mobile platform 100 is inside the tank 10 and also terminates the supplied power and prevents a reengagement of the supplied power later while the mobile platform 100 is inside the tank 10.

FIG. 26 illustrates another CACS 1003 for controlling a charge accumulation between a mobile platform 100 and a tank 10 at least partially filled with a non-conductive, energetic substance 12, 14. The mobile platform 100 may be configured to include an enclosure 200, a control unit 300, a propulsion system 400, and a power supply 500. These components and sub-systems have been already discussed above and will not be described in further detail. A generic electrical power consumer is shown with numeral 1330, which is representative of any device that consumes electrical power, including but not limited to, the control unit 300, the marker detector 306 (FIG. 4), the dynamic sensor 380 (FIG. 13), the propulsion system 400, the task module 600 (FIG. 2), and/or any device not described in the present specification that consumes electrical power.

The mobile platform 100 also includes a retrieval module 700 that has a tether 1010 connected to a buoyant body 702. The tether 1010 may be any of the tethers described in this disclosure or any other connecting cable, line, rope, or wire. The configuration of these components and sub-systems are not limited to any previously described embodiment, e.g., the enclosure 200 need not be inherently safe and the mobile platform 100 may be used in conjunction with a carrier (not shown), which may be a passive or active carrier. Also, two or more enclosures may form the enclosure 200, with each of these separate enclosures acting as housing structures for different components. Moreover, other mobile platforms may include additional components or fewer components. As discussed previously, components of the mobile platform 100 may be formed of two or more separate structures. Thus, while illustrated as single, discrete components, it should be understood that the enclosure 200, control unit 300, and power supply 500, buoyant body 702 may be formed of two or more separate portions, structures, sections, modules, or segments.

To control charge accumulation, the mobile platform 100 may include the CACS 1003, which may be operationally integrated into the mobile platform 100. By operationally integrated, it is meant that the CACS 1003 can, either cooperatively with the control unit 300 or independently, control the operation of sub-systems that initiate movement of the mobile platform 100, such as the propulsion system 400, and/or the delivery or the utilization of electrical power by sub-systems, such as the power supply 500 and control unit 300, respectively. The CACS 1003 may be a component or module of the control unit 300 or a structurally and functionally separate device.

In an embodiment, the CACS 1003 may be configured to control an accumulation of electrical charge on the mobile platform 100. Control may be exerted to reduce a rate of increase in the charge accumulation or reduce a total amount of accumulated charge. The CACS 1003 may include a microprocessor programmed with suitable algorithms, application, or programs and circuitry to transmit control signals based on processed data, which may be pre-programmed and/or acquired during operation. The data may relate to operational data such the time duration of operation, amount of power consumed, time spent moving, data acquired, estimated time to completion of a task, etc. The data may also be acquired using sensors such as voltmeters. Based on pre-programmed criteria, the CACS 1003 transmits control signals to the sub-systems controlling movement of the mobile platform 100 and/or one or more electrical power consumers onboard the mobile platform 100. As used herein, the term "control signals" includes energy waves (e.g., electrical signals, magnetic signals, optical waves, etc.) as well as physical movement (e.g., translation, rotation, etc.)

In response to the control signals from the CACS 1003, the sub-system that receives the control signal(s), or "receiving sub-system," shifts to an operating state that uses less power. By operating at a lower energy state, the rate of increase of charge accumulation on the mobile platform 100 may be either arrested, reduced, or reversed. The control signals may also cause the receiving sub-system to not return to an operating state that requires a higher power consumption. For example, the control signals may instruct the receiving sub-system to not return to the prior operating state or to an operating state that requires electrical power exceeding a predetermined limit. As noted in connection with the embodiment of FIG. 10, the control signal may physically reconfigure an electrical circuit to prevent signal/power transfer while the mobile platform 100 is in the tank 10.

The CACS 1003 may also be configured to provide an indication that charge accumulation control is occurring or will occur after a predetermined time period; i.e., provide an indication of an activation state of the CACS 1003. In one arrangement, the CACS 1003 releases the buoyant body 702 to provide an indication of the activation state. Personnel and/or machinery can detect the presence of the buoyant body 702 visually or by another method such as monitoring for audio signals, light signals, vibrations, etc. In the embodiment of FIG. 10, actuation of the switch assembly 250 shifts the entire mobile platform 100 to a non-operating state while simultaneously releasing the buoyant body 702. Thus, the presence of the buoyant body 702 at or toward a surface 1116 of the non-conductive, liquid energetic substance 12 indicates to personnel and/or machinery that the mobile platform 100 is in a non-operating state. The position at or toward the surface 1116 of the buoyant body 702 and attached tether 1010 is shown in hidden lines. In variants, the buoyant body 702 may be released before charge accumulation control occurs. In such instances, presence of the buoyant body 702 indicates that charge accumulation control will occur after expiration of a predetermined time delay (e.g., ten minutes, thirty minutes, an hour, etc.) or other measurable parameter (e.g., quiescence). In other variants, the buoyant body 702 may be released after charge accumulation control has been initiated. In these instances, presence of the buoyant body 702 indicates that charge accumulation control is presently occurring.

Thus, by detecting the presence of the released buoyant body 702 inside the tank 10, personnel may estimate a magnitude of the electrical charge accumulation on the mobile platform 100 and retrieve the mobile platform after the estimated magnitude of the electrical charge accumulation is below a predetermined value. Depending on the situation, the presence of the released buoyant body 702 may indicate that the magnitude of the electrical charge accumulation is below the predetermined value or that the magnitude of the electrical charge accumulation will be below the predetermined value after expiration of a predetermined time duration after the presence of the released buoyant body 702 has been detected. The predetermined value may be a voltage differential that cannot generate a spark capable of igniting one or more energetic substances in or around the tank 10. The estimation may be based on measurements, laboratory testing, field tests, theoretical calculations or modeling, and/or historical information.

Referring to FIG. 26, in some embodiments, the CACS 1003 may also include an electrical charge dissipater 1500 and an actuator 1502. The electrical charge dissipater 1500 is configured to discharge an electrical charge accumulated on the mobile platform 100 to a voltage differential neutralizing body 1504. The electrical charge dissipater 1500 is shown as electrically connected to one localized region of the enclosure 200. However, in embodiments, the electrical charge dissipater 1500 may be in electrical communication with two or more discrete regions of the enclosure 200 at which electrical charges may accumulate. The voltage differential neutralizing body 1504 may be the tank 10, the non-conductive, liquid energetic substance 12, and/or an object 1506 positioned inside the tank 10. When activated by the CACS 1003, the actuator 1502 extends, drops, exposes or otherwise electrically engages the electrical charge dissipater 1500 with the voltage differential neutralizing body 1504. This electrical connection may reduce the electrical charge accumulation on the mobile platform 100 and thereby reduce a voltage differential between the mobile platform 100 and the voltage differential neutralizing body 1504.

Figure 27:
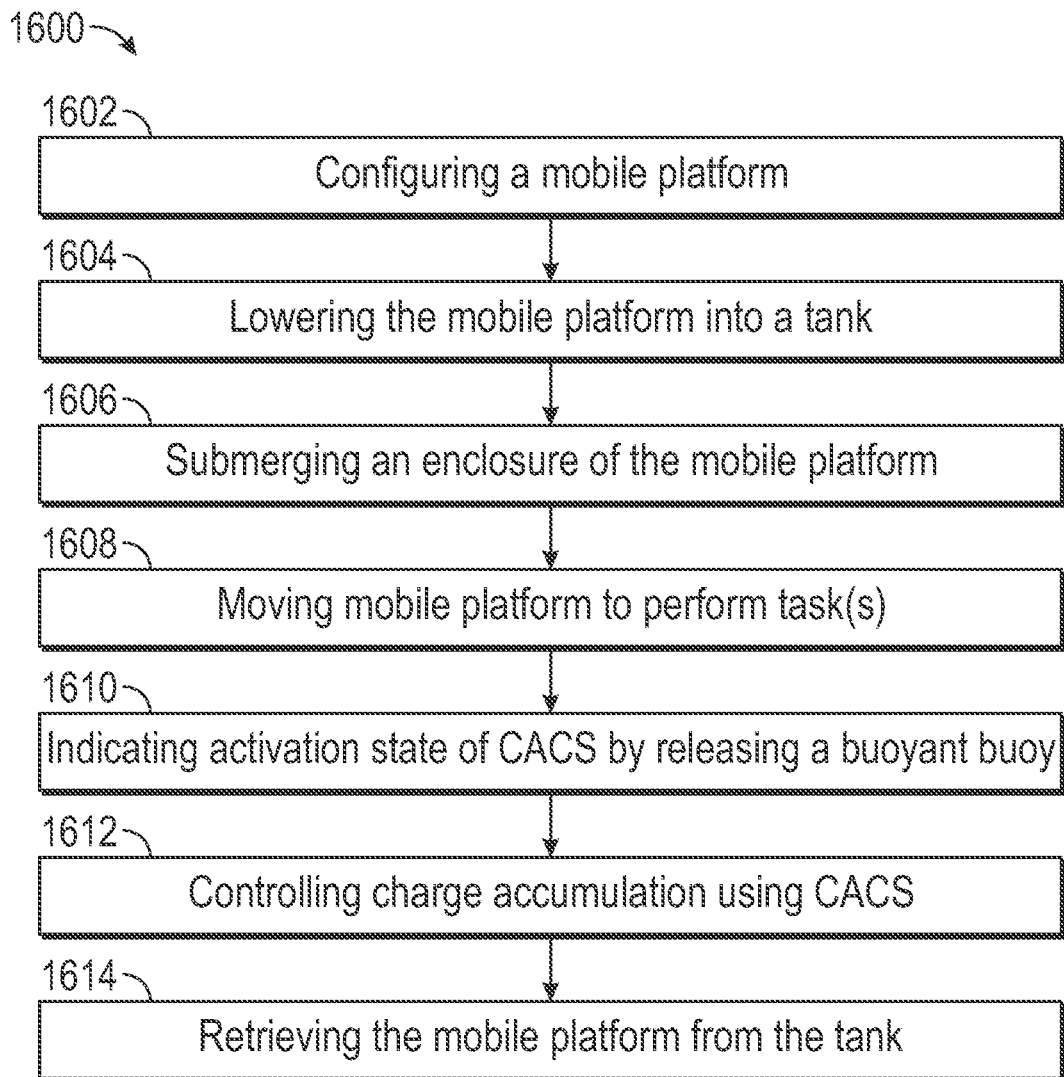
FIG. 27 is a flow chart illustrating a retrieval method according to one embodiment of the present disclosure that uses the system of FIG. 26.

FIG. 27 illustrates a flow chart of one non-limiting embodiment of a retrieval method 1600 according to the present disclosure that employs the CACS 1003. At step 1602, the mobile platform 100 to be retrieved may be configured as shown in FIG. 27. However, the method 1600 may be used to retrieve other mobile devices not described in the present disclosure.

At step 1604, the mobile platform 100 is lowered into the tank 10 using a deployment carrier 50 (FIG. 16A). Other embodiments may use the deployment carriers 764 or 780 (FIGS. 11C, 11D, respectively) or other suitable system for lowering the mobile platform 100 into the tank 10. At step 1606, the enclosure 200 is submerged in the non-conductive, liquid energetic substance 12. If two or more separate enclosures are present, then only one of those separate enclosure needs be submerged. Moreover, the enclosure 200 does not have be fully submerged; i.e., a partially submerged state may be suitable in certain instances. It should be understood that the enclosure 200 need not be completely submerged in the non-conductive, liquid energetic substance 12; i.e., "submerged" does not mean that the entire enclosure 200 is immersed in the non-conductive, liquid energetic substance 12. It should be noted after step 1606, some components used in conjunction with the mobile platform 100, such as an active or passive carrier (not shown) may not be submerged. At step 1608, the mobile platform 100 is used to perform one or more tasks in the tank 10. At step 1610, an activation state of the CACS 1003 is indicated by releasing the buoyant body 702 toward a surface 1116 of the non-conductive, liquid energetic substance 12. At step 1612, the CACS 1003 controls the accumulation of electrical charges on the mobile platform. At step 1614, the mobile platform 100 is retrieved from inside to outside of the tank 10.

Figure 28:
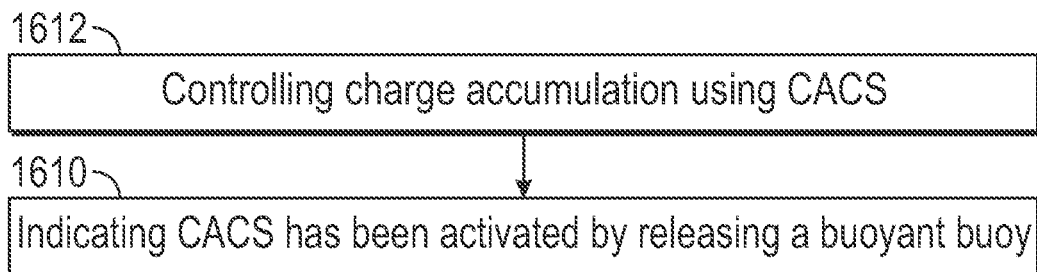
FIG. 28 is a flow chart illustrating alternate steps for activating the charge accumulation control system according an embodiment of the present disclosure.

FIG. 28 depicts a method that reverses the steps of charge accumulation control and indication of such control activity. Specifically, the charge accumulation control step 1612 occurs before the step 1610 of releasing the buoyant body 702. As noted previously, the two steps can also occur simultaneously.

Figure 29:
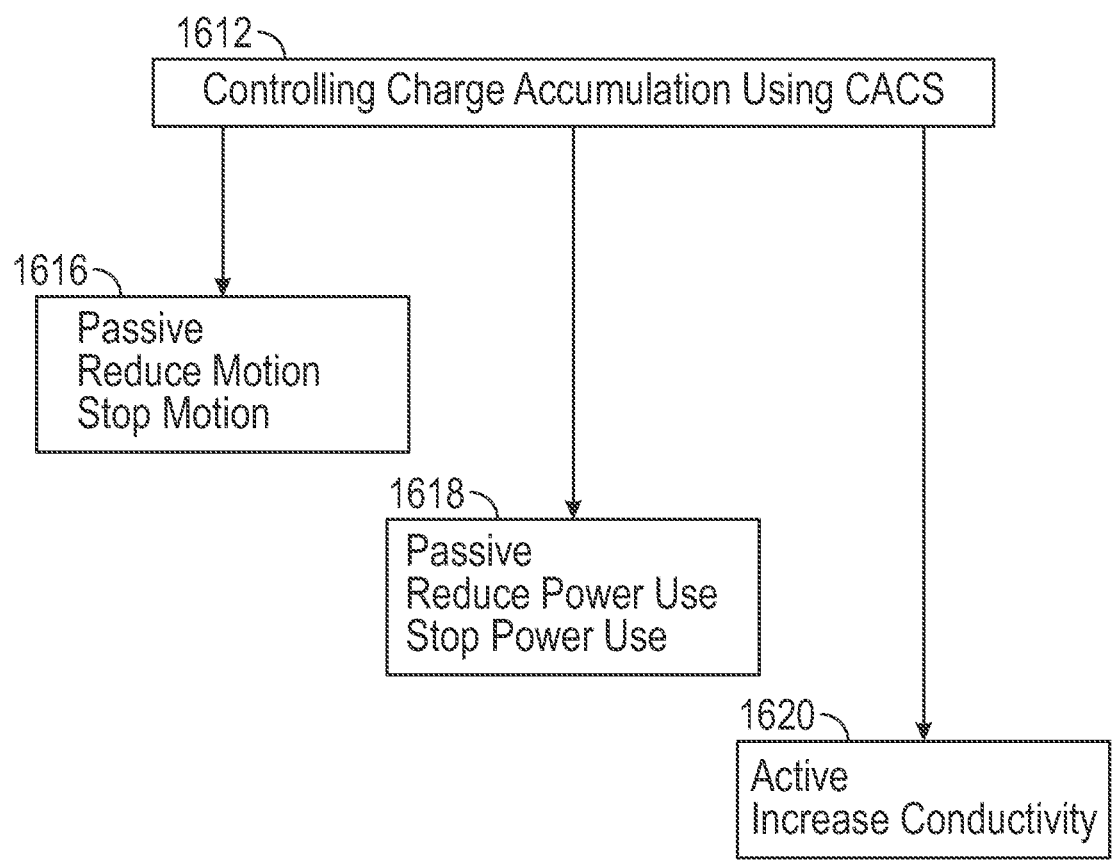
FIG. 29 is a flow chart illustrating exemplary steps for controlling a charge accumulation on a mobile platform according an embodiment of the present disclosure.

FIG. 29 is a flow chart depicting details of steps that may be performed during the charge accumulation control step 1612. The steps 1616, 1618, 1620 are intended to reduce a rate of increase of electrical charge accumulation, maintain a level of accumulated electrical charges, or reduce the amount of accumulated electrical charges. Steps 1616 and 1618 may be considered "passive" in that performance of these steps controls sources contributing to electrical charge accumulation, but not the electrical charge accumulated on the mobile platform 100. Step 1620 may be considered "active" in that performance of this step changes the magnitude of the accumulated electrical charge on the mobile platform 100. These steps may be taken independently or together in any combination. At step 1616, control signals or some form of actuation reduce or stop motion that contributes to electrical charge accumulation. At step 1618, control signals or some form of actuation reduce or stop power usage that contributes to electrical charge accumulation. For both of steps 1616 and 1618, a return to the prior magnitude of motion or power usage is prevented unless acted upon by an input that is external to the mobile platform 100. That is, an actor, whether human or machine, that is external to the mobile platform 100 must take an action, e.g., transmission of a signal or manipulation of some form of switch or other actuator, to allow a return to the prior magnitude of motion or power usage. At step 1620, the electrical charge dissipater 1500 is actuated to discharge some or all of the accumulated electrical charge on the mobile platform 100 into a voltage differential neutralizing body 1504.

It is emphasized that the above described embodiments and related methods are only illustrative of some embodiments of the present disclosure. Other systems and related methods may use an active carrier in conjunction with a mobile platform and may not use an inherently safe enclosure and incorporate one or more features described in connection with FIGS. 2-29.

By "conductive" or "electrically conductive," it is meant an electrical conductivity greater than 100 microsiemens per meter.

By "electrically isolating" two objects, it is meant that the electrical resistance between the two objects exceeds 1 mega ohm.

By "charge accumulation" or "electrical charge accumulation," it is meant the exchange of electrons between two objects resulting in either a positive or negative voltage differential increasing between the two objects.

By "charge dissipation," it is meant the exchange of electrons between two objects resulting in either a positive or negative voltage differential decreasing between the two objects.

By "not conductive" or "not electrically," it is meant an electrical conductivity less than or equal to 100 microsiemens per meter.

An "energetic substance" is any material that is considered to be at risk of igniting or burning. In certain applications, an energetic substance has one or more of the following properties: (i) an Autoignition Temperature (AIT) of 700° C. or less, (ii) a flashpoint of 150° C. or less, (iii) a Minimum Ignition Energy (MIE) of 1.5 mJ or less, and/or (iv) a Minimum Ignition Current Ratio (MICR) of 1.5 or less.

An AIT is the minimum temperature required to initiate or cause self-sustained combustion of a material independently of the heating or heated element. A flashpoint is the minimum temperature at which a liquid gives off vapor in sufficient concentration to form an ignitable mixture with air near the surface of the liquid at standard atmospheric conditions. A MIE is the minimum energy required from a capacitive spark discharge to ignite the most easily ignitable mixture of a gas or vapor. A MICR is the ratio of the minimum current required from an inductive spark discharge to ignite the most easily ignitable mixture of a gas or vapor, divided by the minimum current required from an inductive spark discharge to ignite methane under the same test conditions. A MESG is the maximum gap of the joint between the two parts of the interior chamber of a test apparatus that, when the internal gas mixture is ignited and under standard atmospheric conditions, prevents ignition of the external gas mixture by flame propagating through a 25 mm (984 mils) long joint, for all concentrations of the tested gas or vapor in air.

Energetic substances can be dust, particulates, slurries, solids, liquids, vapors, gases, and combinations thereof. Examples of energetic substances include, but are not limited to, coal dust, hydrocarbon liquids, fuel oils, and gasoline.

"Burning" is the chemical reaction that takes place when an energetic substance is ignited. Burning encompasses combustions, explosions, detonations, and deflagrations. "Ignite," "ignited," and "igniting" mean applying energy of a sufficient quantity to an energetic substance to start the chemical reaction. A "spark" is a thermal event having at least enough energy to ignite an energetic substance. The term "thermal event" includes sparks and sparks caused by explosions. A "combustible" material is a material that undergoes a chemical change that produces heat and light when ignited. A "flammable" material is a gas, liquid or solid that ignites and continues to burn in air if ignited.

It is emphasized that the present teachings can be readily applied to a variety of industries and uses beyond tank inspections, whether above ground or underground. Thus, the described systems and methods are only illustrative of how the advancements of the present disclosure may be implemented. For example, mobile platforms according to the present disclosure may be used in connection with storage units and containers carried by barges, tankers, railroad cars, or ships.

The foregoing description is directed to particular embodiments of the present disclosure for the purpose of illustration and explanation. It will be apparent, however, to one skilled in the art that many modifications and changes to the embodiment set forth above are possible without departing from the scope of the disclosure. Thus, it is intended that the following claims be interpreted to embrace all such modifications and changes.

We claim:

1. A method of retrieving a mobile platform from a tank at least partially filled with a non-conductive, energetic substance, the method comprising:

configuring the mobile platform to include at least:
  an enclosure,
    at least one control unit positioned inside the enclosure,
    at least one propulsion system positioned at least partially inside the enclosure,
    at least one power supply positioned inside the enclosure,
    at least one retrieval system disposed at least partially on the enclosure, the at least one retrieval system including at least one buoyant body, an electrically conductive member, and at least one tether, the at least one tether having at least a portion that is not conductive, the at least one tether electrically isolating the at least one buoyant body from the enclosure;
  lowering the mobile platform into the tank using a deployment carrier;
  submerging the enclosure in the non-conductive, liquid energetic substance;
  moving the mobile platform using the at least one propulsion system to perform at least one task in the tank,
  releasing the buoyant body to convey the at least one tether toward a surface of the non-conductive, liquid energetic substance;
  conveying an electrically conductive cable to the electrically conductive member of the mobile platform using the at least one tether;
  electrically connecting a voltage neutralizing end of the electrically conductive cable to a voltage differential neutralizing body in a spark inhibiting ambient condition;
  electrically connecting a mobile platform end of the electrically conductive cable to the electrically conductive member of the mobile platform while the electrically conductive member is below the surface of the non-conductive, liquid energetic substance; and
  retrieving the mobile platform from inside to outside of the tank.

2. The method of claim 1, wherein the spark inhibiting ambient condition is at least one of: (i) energetic substance deficient, (ii) and oxygen deficient.

3. The method of claim 1, wherein the voltage differential neutralizing body is the tank.

4. The method of claim 1, wherein the electrically conductive cable has an electrical connector disposed at the mobile platform end, and further comprising:
  conveying the electrical connector to the mobile platform using the at least one tether and electrically connecting the electrical connector to the electrically conductive member.

5. The method of claim 1, further comprising estimating when a voltage differential between the mobile platform and the tank is below a predetermined value and retrieving the mobile platform from inside to outside of the tank only after the estimated voltage differential is below the predetermined value.

6. The method of claim 1, further comprising:
  retrieving the buoyant body with a retrieval member;
  attaching a mobile platform end of the electrically conductive cable to the at least one tether; and
  sliding the mobile platform end along the at least one tether to the mobile platform, wherein the mobile platform end is electrically connected to the electrically conductive member.

7. The method of claim 1, wherein the mobile platform end of the electrically conductive cable is connected electrically to the electrically conductive member before the neutralizing body end of the electrically conductive cable is connected electrically to the voltage differential neutralizing body.

8. The method of claim 1, wherein the mobile platform end of the electrically conductive cable is connected electrically to the electrically conductive member after the neutralizing body end of the electrically conductive cable is connected electrically to the voltage differential neutralizing body.

9. The method of claim 8, wherein the electrically conductive cable is conveyed using the at least one tether before the neutralizing body end of the electrically conductive cable is connected electrically to the voltage differential neutralizing body.

10. The method of claim 1, wherein the enclosure includes a plurality of separate enclosures, and at least one enclosure of the plurality of separate enclosures is submerged in the non-conductive, liquid energetic substance.

* * * * *